US008148508B2

(12) United States Patent
Wagner et al.

(10) Patent No.: US 8,148,508 B2
(45) Date of Patent: Apr. 3, 2012

(54) METHOD FOR ENZYMATIC PRODUCTION OF GLP-2(1-33) AND GLP-2(1-34) PEPTIDES

(75) Inventors: Fred W. Wagner, Walton, NE (US); Peng Luan, Omaha, NE (US); Yuannan Xia, Lincoln, NE (US); Daniel Strydom, Lincoln, NE (US); Jin Seog Seo, Brampton (CA)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 12/861,714

(22) Filed: Aug. 23, 2010

(65) Prior Publication Data
US 2011/0130556 A1    Jun. 2, 2011

Related U.S. Application Data

(60) Division of application No. 10/997,065, filed on Nov. 24, 2004, now Pat. No. 7,781,567, which is a continuation of application No. PCT/US03/16649, filed on May 23, 2003.

(60) Provisional application No. 60/383,359, filed on May 24, 2002, provisional application No. 60/383,468, filed on May 24, 2002.

(51) Int. Cl.
C07H 21/04    (2006.01)

(52) U.S. Cl. .................................... 536/23.51

(58) Field of Classification Search .......... None
See application file for complete search history.

(56) References Cited

U.S. PATENT DOCUMENTS

| | | |
|---|---|---|
| 4,336,336 A | 6/1982 | Silhavy et al. |
| 4,551,433 A | 11/1985 | DeBoer |
| 4,588,684 A | 5/1986 | Brake |
| 4,689,406 A | 8/1987 | Banks et al. |
| 4,738,921 A | 4/1988 | Belagaje et al. |
| 4,745,056 A | 5/1988 | Guterman et al. |
| 4,837,148 A | 6/1989 | Cregg |
| 4,870,023 A | 9/1989 | Fraser et al. |
| 4,873,192 A | 10/1989 | Kunkel |
| 4,876,197 A | 10/1989 | Burke et al. |
| 4,880,734 A | 11/1989 | Burke et al. |
| 4,929,555 A | 5/1990 | Cregg et al. |
| 5,110,729 A | 5/1992 | Maeda et al. |
| 5,352,771 A | 10/1994 | Kostic et al. |
| 5,393,924 A | 2/1995 | Tafesh et al. |
| 5,416,007 A | 5/1995 | Charette et al. |
| 5,420,242 A | 5/1995 | Gautvik et al. |
| 5,457,066 A | 10/1995 | Frank et al. |
| 5,580,751 A | 12/1996 | Buchardt et al. |
| 5,595,887 A | 1/1997 | Coolidge et al. |
| 5,602,034 A | 2/1997 | Tekamp-Olson |
| 5,629,205 A | 5/1997 | Lagosky |
| 5,707,826 A | 1/1998 | Wagner et al. |
| 5,728,543 A | 3/1998 | Dorschug et al. |
| 5,789,379 A | 8/1998 | Drucker et al. |
| 5,814,603 A | 9/1998 | Oldenburg et al. |
| 5,851,810 A | 12/1998 | Blanchard |
| 5,853,976 A | 12/1998 | Hesse et al. |
| 5,912,229 A | 6/1999 | Thim et al. |
| 6,110,707 A * | 8/2000 | Newgard et al. ............. 435/69.4 |
| 6,130,063 A | 10/2000 | Lawlis |
| 6,171,823 B1 | 1/2001 | Woldike et al. |
| 6,184,201 B1 | 2/2001 | Drucker et al. |
| 6,313,092 B1 | 11/2001 | Holladay et al. |
| 6,316,224 B1 | 11/2001 | Xia |
| 6,461,834 B1 | 10/2002 | Dormady et al. |
| 6,660,758 B1 | 12/2003 | Nicolaou et al. |
| 6,660,763 B2 | 12/2003 | Tang et al. |
| 6,703,484 B2 | 3/2004 | Chatterjee et al. |
| 7,335,486 B2 | 2/2008 | Wagner et al. |
| 2005/0221444 A1 | 10/2005 | Williams et al. |
| 2005/0227313 A1 | 10/2005 | Seo et al. |
| 2005/0260701 A1 | 11/2005 | Wagner et al. |
| 2005/0287632 A1 | 12/2005 | Holmquist et al. |
| 2006/0008870 A1 | 1/2006 | Wagner et al. |
| 2006/0024778 A1 | 2/2006 | Wagner et al. |

FOREIGN PATENT DOCUMENTS

| | | |
|---|---|---|
| EP | 0164556 A2 | 12/1958 |
| EP | 0036259 A2 | 9/1981 |
| EP | 0036776 A2 | 9/1981 |
| EP | 0060057 A1 | 9/1982 |
| EP | 0063953 | 11/1982 |
| EP | 0121775 A1 | 10/1984 |
| EP | 0127839 | 12/1984 |
| EP | 0136829 | 4/1985 |
| EP | 0136907 | 4/1985 |
| EP | 0155476 | 9/1985 |
| EP | 0267851 A2 | 5/1988 |
| EP | 0284044 A1 | 9/1988 |
| EP | 0329203 A1 | 8/1989 |
| EP | 0473128 A | 3/1992 |

(Continued)

OTHER PUBLICATIONS

Advisory Action issued in U.S. Appl. No. 10/997,697 dated Oct. 1, 2008.
Advisory Action issued in U.S. Appl. No. 10/997,762 dated Jul. 15, 2008.
Aubin, et al. "Highly effective delivery of foreign DNA to adherent cells via polybrene/DMSO-assisted gene transfer", Methods Mol. Biol., 62 (1997), 319-42.
Beach, et al. "Functionally homologous cell cycle control genes in budding and fission yeast", Nature, 300(5894), Dec. 23, 1982, 706-9.
Birnstiel, et al., "Transcription termination and 3' procession: the end is in site!", Cell, 41(2), Jun. 1985, 349-59.
Buhl, et al., J. Biol. Chem. 263(18):8621, 1988.
Catsimpoolas, et al., "Specific cleavage of cystine peptides by cyanide", J. of Biol. Chem., 241(8), Apr. 25, 1996, 1790-6.
Chang, J., Eur. K. Biochem. 151, 1985, 217-224.

(Continued)

Primary Examiner — Christina Bradley
(74) Attorney, Agent, or Firm — Stoel Rives LLP

(57) ABSTRACT

The invention provides methods for making peptides from a polypeptide containing at least one copy of the peptide using clostripain to excise the peptide from the polypeptide. The methods enable the use of a single, highly efficient enzymatic cleavage to produce any desired peptide sequence.

19 Claims, 17 Drawing Sheets

FOREIGN PATENT DOCUMENTS

| EP | 0978565 A1 | 2/2000 |
|---|---|---|
| WO | WO 9317110 | 9/1993 |
| WO | WO 9517510 | 6/1995 |
| WO | WO 9617941 A3 | 6/1996 |
| WO | WO 9803664 A1 | 1/1998 |
| WO | WO 9964611 A | 12/1999 |
| WO | WO 0006763 A1 | 2/2000 |
| WO | WO 0026418 A1 | 5/2000 |
| WO | WO 0028067 | 5/2000 |
| WO | WO 0149314 A2 | 7/2001 |
| WO | WO 02061105 A2 | 8/2002 |
| WO | WO 03099848 A | 12/2003 |
| WO | WO 03099854 | 12/2003 |
| WO | WO 03100022 A2 | 12/2003 |
| WO | WO 2004011599 A2 | 2/2004 |

OTHER PUBLICATIONS

Coombs, et al. "Substrate specificity of prostate-specific antigen (PSA)", Chem Biol. 5(9), Sep. 1998, 475-88.

Dargatz, et al., "The heterodimeric protease clostripain from *Clostridium histolyticum* is encoded by a single gene", Molecular and General Genetics, vol. 240, No. 1, Jul. 1, 1993, 140-145.

Davies, et al., "Plasmid-determined resistance to antimicrobial agents", Anuu. Rev. Microbiol. 32, 1978, 469-518.

Database EMBL (online), Jul. 12, 2001, "Glucagon [*Homo sapiens*]", XP002501257 retrieved from NCBI Apr. 21, 2009, database accession No. AAH05278, the whole document.

Dijkema, et al., "Cloning and expression of the chromosomal immune interferon gene of the rat", EMBO J. 4(3), Mar. 1985, 761-7.

Djuran, et al., "Hydrolysis of amide bond in histidine-containing peptides promoted by chelated amino acid palladium(II) complexes: dependence of hydrolytic pathway on the coordination modes of the peptides", Polyhedron 18(27), Sep. 14, 1999, 3611-3616.

Dou, et al., "Preliminary study on the cleavage of chimeric protein GST-CMIV with palladate(II) complex", Pre. Biochem. & Biotechnol. 2000, vol. 30, No. 1, 69-78.

Drexler, et al., "Palladium (II) and platinum (II) complexes with 1,5-dithiacyclooctane(dtco)—structures of Pd(dtco)C12 and Pd(dtco2)(NO3)2 and kinetics of ligand substitution in [Pd(dtco2)]2plus by bidenate ligands", Inorganic Chemistry, 30c, 1991, 1297-1302.

Dykes, et al., "Expression of atrial natriuretic factor as a cleavable fusion protein with chloramphenicol acetltransferase in *Escherichia coli*", Eur. J. Biochem., 174(2), Jun. 1, 1988, 411-6.

Felgner, et al., "Enhanced gene delivery and mechanism studies with a novel series of cationic lipid formulations", J. Biol. Chem. 269(4), Jan. 28, 1994, 2550-61.

Forsberg, et al., "An evaluation of different enxymatic cleavage methods for recombinant fusion proteins, applied on des(1-3)insulin-like growth factor I", J. Protein Chem., 11(2), Apr. 1992, 201-11.

Forsberg, et al., "Comparison of two chemical cleavage methods for preparation of a truncated form of recombinant human insulin-like growth factor I from a secreted fusion protein", Biofactors, 2(2), Dec. 1989, 105-12.

Gluzman, "SV40-Transformed cells support the replication of early sv40 mutants", Cell, 23(1), Jan. 1981, 175-182.

Gram, et al., "A novel approach for high level production of a recombinant human prathyroid hormone fragment in *Escherichia coli*", Biotechnology (NY), 12(10), Oct. 1994, 1017-23.

Greger, et al., "Poly(A) signals control both transcriptional termination and initiation between the tandem GAL 10 and GAL7 genes of *Saccharomyces cerevisiae*", EMBO J. 17(16), Aug. 17, 1998, 4771-9.

Guo, et al., "Protein tolerance to random amino acid change", 2004, Proc. Natl. Acad. Sci. 101: 9205-9210.

Hill, "Functional analysis of conserved histidines in ADP-Glucose pyrophophorylase from *Escherichia coli*", 1998, Biochem. Biophys. Res. Comm. 244:573-577.

Hohman, et al., "Rate and equilibrium data for substitution reactions of diaqua(ethylenediamine)palladium(II) with chloride in aqueous solution", Inorganic Chemistry Acta, 174(1), 1990, 87-92.

International Preliminary Examination Report issued in International Application No. PCT/US2003/16645 mailed Nov. 12, 2004.

International Search Report issued in International Application No. PCT/US2003/16645 mailed May 24, 2004.

International Preliminary Examination Report issued in International Application No. PCT/US2003/16469 mailed Feb. 9, 2005.

International Search Report issued in International Application No. PCT/US2003/16469 mailed Oct. 28, 2004.

International Preliminary Examination Report issued in International Application No. PCT/US2003/16470 mailed Jul. 6, 2005.

International Search Report issued in International Application No. PCT/US2003/16470 mailed Jul. 21, 2004.

International Preliminary Examination Report issued in International Application No. PCT/US2003/16649 dated May 15, 2007.

International Search Report issued in International Application No. PCT/US2003/16649 dated Dec. 11, 2006.

International Search Report issued in International Application No. PCT/US2003/016647 dated Jul. 2, 2004.

International Preliminary Examination Report issued in International Application No. PCT/US2003/16647 dated Aug. 23, 2004.

International Search Report issued in International Application No. PCT/US2003/16642 dated Sep. 3, 2004.

International Preliminary Examination Report issued in International Application No. PCT/US2003/16642 dated Mar. 6, 2006.

International Search Report issued in International Application No. PCT/US2003/16643 dated Jul. 20, 2004.

International Prelminary Examination Report issued in International Application No. PCT/US2003/16643 dated Aug. 21, 2004.

International Preliminary Examination Report issued in International Application No. PCT/US2003/16468 dated Dec. 16, 2004.

International Search Report issued in International Application No. PCT/US2003/16468 dated Jan. 15, 2004

International Preliminary Examination Report issued in International Application No. PCT/IB2004/004439 dated May 22, 2006.

International Search Report issued in International Application No. PCT/IB2004/004439 dated Sep. 23, 2005.

Ito, et al., "Transformation of intact yeast cells treated with alkali cations", J. Bacteriol, 153(1), Jan. 1983, 163-8.

Kaufman et al., "The phosphorylation state of eucaryotic initiation factor 2 alters translational efficiency of specific mRNAs", Mol. Cell Biol., 9(3), Mar. 1989, 946-58.

Knott, et al., "The isolation and characterisation of human atrial natriuretic factor produced as a fusion protein in *Escherichia coli*", Eur. J. Biochem., 174(2), Jun. 1, 1988, 405-10.

Kohrer, et al., "Import of amber and ochre suppressor tRNAs into mammalian cells: a general approach to site-specific insertion of amino acid analogues into proteins", Proc. Natl. Acad. Sci. USA, 98(25), Dec. 4, 2001, 14310-5.

Kowal, et al., "Twenty-first aminoacyl-tRNA synthetase-suppressor tRNA pairs for possible use in site-specific incorporation of amino acid analogues into proteins in eukaryotes and in eubacteria", Proc. Natl. Acad. Sci. USA 98(5), Feb. 27, 2001, 2268-73.

Kunkel, T.A., "Rapid and efficient site-specific mutagenesis without phenotypic selection", Proc. Natl. Acad. Sci. USA, 82, 1985 488-492.

Kurtz, et al., "Integrative transformation of *Candida albicans*, using a cloned Candida ADE2 gene", Mol. Cell Biol., 6(1), Jan. 1986, 142-9.

Labouesses, B., "L'Ydrolyse du glucogon par la clostripaine", Bull. Soc. Chim. Biol., 42, 1960, 1293-1304.

Labouesse, B., "La Clostripaine, Protease De Clostridium Histolyticum II.—Specificite", Bull. Soc. Chim. Biol., 42, 1960, 559-568.

Lazar, et al., "Transforming growth factor alpha: mutation of aspartic acid 47 and leucine 48 results in different biological activities", 1988, Mol. Cell Biol. 8:1247-1252.

Lebacq-Verheyden, et al., "Posttranslational proccessing of endogenous and of baculovirus-expressed human gastrin-releasing peptide precursor", Mol. Cell Biol. 8(8), Aug. 1988 3129-35.

Lee et al., "Enhanced expression of tandem multimers of the antimicrobial peptide buforin II in *Escherichia coli* by the DEAD-box protein and trxB mutant", Appl. Microbiol. Biotechnol. 58(6), May 2002, 790-6.

Lidell, et al., "An autocatalytic cleavage in the C terminus of the human MUC2 mucin occurs at the low pH of the late ceretory pathway", J. Biol. Chem., vol. 278, No. 16, Apr. 18, 2003, 13944-13951.
Maniatis, et al., "Regulation of inducible and tissue-specific gene expression", Science, 236(4806), Jun. 5, 1987, 1237-45.
Marcus, F., "Preferential cleavage at aspartyl-prolyl peptide bonds in dilute acid", Int. J. Pept. Protein Res., 25(5), May 1985, 542-6.
Marczinovits et al., "An alternative purification protocol for producing hepatitis B virus X antigen on a preparative scale in *Escherichia coli*", J. Biotechnology, 1997, vol. 56, 81-88.
Marumoto, et al., "Hyperproduction of polyhedrin-IGF II infusion protein in silkworm larvae infected with recombinant Bombyx mori nuclear polyhedrosis virus", J. Gen. Virol., 68 (pt10), 1987, 2599-2606.
Masson, et al., "Transformation of *Bacillus thuringiensis* vegetative cells by electroporation", FEMS Microbiol. Lett., 51(3), Aug. 1989, 273-7.
McCarroll, et al "Stable insect cell cultures for recombinant protein production", Curr Opin Biotechnol. 8(5), Oct. 1997, 590-4.
Meiwes, et al., "Clostripain: production and use for peptide synthesis", Biomedica Biochimica Acta, 1991, vol. 50, No. 10-11, S80-S83.
Milovic, et al. "Interplay of terminal amino group and coordinating side chains in directing regioselective cleavage of natural peptides and proteins with palladium (II) complexes", Inorganic Chemistry, Dec. 2002, vol. 41, No. 26.
Milovic, et al., "Palladium(II) and platinum(II) complexes as synthetic peptidases", Metlons Biol. Syst., 38, 2001, 145-186.
Milovic,e t al., "Palladium(II) complexes, as synthetic peptidases, regioselectively cleave the second peptide bond 'upstream' from methionine and histidine side chains", J. Amer. Chem. Soc. 124(17), May 1, 2002, 4759-4769.
Mitchell, et al., "Purification and properties of enz clostridio peptidase B clostripain clostridium-histolyticum", J. Biol. Chem., vol. 243, No. 18, 1968, 4683-4682.
Mitchell, et al., "Cleavage at arginine residues by clostripain", Methods in Enzymology, Academic Press Inc., vol. 47, Jan. 11977, 165-170.
Miyanohara, et al., "Expression of hepatitis B surface antigen gene in yeast", Proc. Natl. Acad. Sci. USA, 801(1), Jan. 1983, 1-5.
Moks, et al., "Expression of human insulin-like growth factor I in bacteria: use of optimized gene fusion vectors to facilitate protein purification", Biochemistry, 26(17), Aug. 25, 1987, 5239-44.
Nilsson, et al., "Multiple affinity domains for the detection, purification and immobilization of recombinant proteins", J. of Molecular Recognition, 9(5/6), 1996, John Wiley & Sons, Dec. 9, 1996, 585-594.
Notice of Allowance issued in U.S. Appl. No. 10/997,822 dated May 14, 2009.
Notice of Allowance issued in U.S. Appl. No. 10/997,078 dated Oct. 23, 2008.
Notice of Allowance issued in U.S. Appl. No. 11/944,165 dated Oct. 15, 2008.
Notice of Allowance issued in U.S. Appl. No. 10/997,074 dated Sep. 21, 2007.
Office Action (non-final) issued in U.S. Appl. No. 10/997,078 dated Jun. 25, 2007.
Office Action (non-final) issued in U.S. Appl. No. 10/997,074 dated Dec. 15, 2006.
Office Action (non-final) issued in U.S. Appl. No. 10/997,065 dated Jan. 18, 2008.
Office Action (non-final) issued in U.S. Appl. No. 10/997,065 dated Oct. 21, 2008.
Office Action (non-final) issued in U.S. Appl. No. 10/997,700 dated Oct. 4, 2007.
Office Action (non-final) issued in U.S. Appl. No. 10/997,700 dated Apr. 7, 2008.
Office Action (non-final) issued in U.S. Appl. No. 10/997,697 dated Sep. 11, 2007.
Office Action (final) issued in U.S. Appl. No. 10/997,697 dated Jul. 7, 2008.
Office Action (non-final) issued in U.S. Appl. No. 10/997,697 dated Mar. 2, 2009.
Office Action (non-final) issued in U.S. Appl. No. 10/997,078 dated Jan. 9, 2008.
Office Action (final) issued in U.S. Appl. No. 10/997,078 dated Jul. 23, 2008.
Office Action (non-final) issued in U.S. Appl. No. 10/997,822 dated Oct. 4, 2007.
Office Action (non-final) issued in U.S. Appl. No. 10/997,822 dated Apr. 30, 2008.
Office Action (non-final) issued in U.S. Appl. No. 10/997,822 dated Nov. 14, 2008.
Office Action (non-final) issued in U.S. Appl. No. 10/997,762 dated Oct. 9, 2007.
Office Action (non-final) issued in U.S. Appl. No. 11/944,165 dated May 30, 2008.
Office Action (final) issued in U.S. Appl. No. 10/997,762 dated Apr. 17, 2008.
Office Action (non-final) issued in U.S. Appl. No. 11/997,762 dated Jan. 7, 2009.
Office Action (non-final) issued in U.S. Appl. No. 11/997,762 dated Apr. 2, 2009.
Office Action (non-final) issued in U.S. Appl. No. 10/993,127 dated Jun. 2, 2006.
Office Action (final) issued in U.S. Appl. No. 10/993,127 dated Dec. 22, 2006.
Office Action (non-final) issued in U.S. Appl. No. 10/993,127 dated May 2, 2007.
Office Action (non-compliant amendment) issued in U.S. Appl. No. 10/993,127 dated Mar. 5, 2008.
Office Action (final) issued in U.S. Appl. No. 10/993,127 dated Oct. 1, 2008.
Office Action (non-final) issued in U.S. Appl. No. 10/993,127 dated May 12, 2009.
Office Action (non-final) issued in U.S. Appl. No. 10/993,127 dated Mar. 3, 2010.
Okamoto, et al., "Structural characterization of argingipain, a novel arginine-specific cysteine proteinase as a major periodontal pathogenic factor from *Porphyromonas gingivilis*", Archives of Biochemistry and Biophysics, 316(2), Feb. 1, 1995, 917-925.
Orksov, et al., "Biological effects and metabolic rates of glucagolike peptide-1 7-36 amide and glucagonlike peptide-1 7-37 in healthy subjects are indistinguishable", Diabetes, 42(5), May 1993, 658-661.
Parac, et al., "New regioselectivity in the cleavage of histidine-containing peptides by palladium(ii) complexes studied by kinetic experiments and molecular dynamics simulations", J. Am. Chem. Soc., 1999, 121:3127-3135.
Parks, et al., "Role of proline, cysteine and a disulphide bridge in the structure and activity of the anti-microbial peptide gaegurin 5", Biochem. J. 368(Pt 1), 2002, 171-182.
Pearson, et al., "Searching protein sequence libraries: comparison of the sensitivity and selectivity of the Smith-Waterman and FASTA alogorithms", Genomics, 11(3), Nov. 1991, 635-50.
Piers, et al., "Recominant DNA procedures for producing small antimicrobial cationic peptides in bacteria", Gene, 134(1), Nov. 30, 1993, 7-13.
Pilon, et al., "Ubiquitin fusion technology: bioprocessing of peptides", Biotechnol. Prog., 13(4), Jul.-Aug. 1997, 374-9.
Pop, et al., "The twin-arginine signal peptide of phoD and the TatAd/Cd proteins *Bacillus subtillis* from an autonomous tat translocation system", J. Biological Chem., 277(5), American Society of Biolochemical Biologists, Birmingham, Feb. 1, 2002, 3268-3273.
Preliminary Amendment filed in U.S. Appl. No. 10/993,127, filed Apr. 11, 2005.
Raibud, et al., "Positive control of transcription initiation in bacteria", Annu. Rev. Genet., 18, 1984, 173-206.
Rau, et al., "Complex formation and ligand substitution reactions of (2-picolylamine)palladium(II) with various biologically relevant ligands. Characterization of (2-picolyamine)(1,1-cyclobutanedicarboxylato)palladium(II)", Inorganic Chemistry, 36, 1997, 1454-1463.
Ray, et al., "Production of recombinant salmon calcitonin by in vitro amidation of *Escherichia coli* produced precursor peptide", Biotechnology (NY) 11(1), Jan. 1993, 64-70.

Response to Office Action filed in U.S. Appl. No. 10/997,697, filed Mar. 5, 2008.
Response after final Office Action filed in U.S. Appl. No. 10/997,697, filed Sep. 8, 2008.
Request for Continued Examination filed in U.S. Appl. No. 10/997,697, filed Nov. 7, 2008.
Response to Restriction Requirement filed in U.S. Appl. No. 10/997,697, filed Apr. 5, 2007.
Restriction Requirement issued in U.S. Appl. No. 10/997,697 dated Feb. 27, 2007.
Response to Office Action filed in U.S. Appl. No. 10/997,078, filed Oct. 25, 2007.
Response to Office Action filed in U.S. Appl. No. 10/997,078, filed Apr. 8, 2008.
Response after final Office Action filed in U.S. Appl. No. 10/997,078, filed Sep. 23, 2008.
Response to Restriction Requirement filed in U.S. Appl. No. 10/997,078, filed May 2, 2007.
Restriction Requirement issued in U.S. Appl. No. 10/997,078 dated Apr. 2, 2007.
Response to Office Action filed in U.S. Appl. No. 10/997,822, filed Jan. 3, 2008.
Response to Office Action filed in U.S. Appl. No. 10/997,822, filed Jul. 30, 2008.
Response to Office Action filed in U.S. Appl. No. 10/997,822, filed Feb. 17, 2009.
Response to Restriction Requirement filed in U.S. Appl. No. 10/997,822, filed Jul. 25, 2007.
Restriction Requirement issued in U.S. Appl. No. 10/997,822 dated Jun. 25, 2007.
Response to Office Action filed in U.S. Appl. No. 11/944,165, filed Aug. 29, 2008.
Response to Office Action filed in U.S. Appl. No. 10/997,074, filed Feb. 22, 2007.
Response to Restriction Requirement filed in U.S. Appl. No. 10/997,074, filed Nov. 27, 2006.
Restriction Requirement issued in U.S. Appl. No. 10/997,074 dated Oct. 26, 2006.
Response to Office Action filed in U.S. Appl. No. 10/997,762, filed Jan. 9, 2008.
Response after final Office Action filed in U.S. Appl. No. 10/997,762, filed Jun. 17, 2008.
Response to Office Action filed in U.S. Appl. No. 10/997,762, filed Jan. 21, 2009.
Request for Continued Examination filed in U.S. Appl. No. 10/997,762, filed Oct. 17, 2008.
Response to Restriction Requirement filed in U.S. Appl. No. 10/997,762, filed Jul. 17, 2007.
Restriction Requirement issued in U.S. Appl. No. 10/997,762 dated Jun. 18, 2007.
Restriction Requirement issued in U.S. Appl. No. 10/997,065 dated Apr. 10, 2007.
Response to Restriction Requirement filed in U.S. Appl. No. 10/997,065, filed Aug. 8, 2007.
Response to Office Action filed in U.S. Appl. No. 10/997,065, filed Jul. 18, 2008.
Response to Office Action filed in U.S. Appl. No. 10/997,065, filed Apr. 21, 2009.
Response to Office Action filed in U.S. Appl. No. 10/997,700, filed Jan. 4, 2008.
Response to Office Action filed in U.S. Appl. No. 10/997,700, filed Jan. 12, 2009.
Restriction Requirement issued in U.S. Appl. No. 10/997,700 dated Jul. 3, 2007.
Response to Restriction Requirement filed in U.S. Appl. No. 10/997,700, filed Jul. 30, 2007.
Response to Office Action filed in U.S. Appl. No. 10/993,127, filed Oct. 2, 2006.
Request for Continued Examination filed in U.S. Appl. No. 10/993,127, filed Mar. 21, 2007.
Response to Office Action filed in U.S. Appl. No. 10/993,127, filed Aug. 9, 2007.
Response to Office Action filed in U.S. Appl. No. 10/993,127, filed Jun. 5, 2008.
Response to Office Action filed in U.S. Appl. No. 10/993,127, filed Nov. 16, 2009.
Request for Continued Examination filed in U.S. Appl. No. 10/993,127, filed Apr. 1, 2009.
Restriction Requirement issued in U.S. Appl. No. 10/993,127 dated Mar. 22, 2008.
Response to Restriction Requirement filed in U.S. Appl. No. 10/993,127, filed Apr. 21, 2006.
Schellenberger, et al., "Peptide production by a combination of gene expression, chemical synthesis, and protease-catalyzed conversion", Int. J. Pept. Protein Res., 41(4), Apr. 1993, 326-32.
Shen, S.H., "Multiple joined genes prevent product degratation in *Escherichia coli*", Proc. Natl. Acad. Sci. USA, 81(15), Aug. 1984, 4627-31.
Shimatake, et al., "Purified lambda regulatory protein cll positively activates promoters for lysogenic development", Nature, 292(5819), Jul. 9, 1981, 128-32.
Shimizu, et al., "Transfer of cloned human class I major histocompatibility complex genes into HLA mutant human lymphoblastoid cells", Mol. Cell Biol. 6(4), Apr. 1986, 1074-87.
Shine, et al., "Determinant of cistron specificity in bacterial ribosomes", Nature 254(5495), Mar. 6, 1975, 34-8.
Simmonds, et al., "Molecular interatcions between vestigial and scalloped promote wing formation in drosophila", Genes Dev. 12(24), Dec. 15, 1998, 3815-20.
Smith, et al. "Surface point mutations that significantly alter the structure and stability of a protein's denatured state", Protein Science, 1996, vol. 5, 2009-2019.
Sprengart, et al., "The downstream box: an efficient and independent translation initiation signal in *Escherichia coli*", EMBO J., 15(3), Feb. 1, 1996, 665-74.
Supplementary European Search Report issued in EP Application No. 03755506 dated Nov. 7, 2008.
Supplementary European Search Report issued in EP Application No. 03734200 dated Feb. 27, 2006.
Supplementary European Search Report issued in EP Application No. 03755504 dated Mar. 14, 2006.
Supplementary European Search Report issued in EP Application No. 03734201 dated Jul. 4, 2006.
Supplementary European Search Report issued in EP Application No,. 03771535 dated Oct. 1, 2008.
Supplementary European Search Report issued in EP Application No. 03734173 dated Nov. 12, 2008.
Supplementary European Search Report issued in EP Application No. 03734172 dated Apr. 17, 2007.
Supplementary European Search Report issued in EP Application No. 03736710 dated Jun. 26, 2007.
Supplementary Partial European Search Report issued in EP Application No. 04821092.6 dated Jun. 28, 2007.
Supplementary European Search Report issued in EP Application No. 04821092.6 dated Jun. 28, 2007.
Taketo, "DNA transfection of *Escherichia coli* by electroporation" Biochim. Biophys. Acta. 949(3), Mar. 31, 1988, 318-24.
"Tertiary Structure", Tertiary Structure Biological Pages, hhtp://users.rcn.com/jkimball.ma.ultranet/biologicalpages/t/tertiarystructure.html (downloaded Oct. 14, 2005) 3 pgs.
Van Iddekinge, et al., "Nucleotide sequence of the polyhedrin gene of autographa californica nuclear polyhedrosis virus", Virology, 131, 1983, 561-564.
Wang, et al., "Natural transformation in campylobacter species", J. Bacteriol, 171(2), Feb. 1990, 949-55.
Waterman, et al., "Pattern recognition in several sequences: consensus and alignment", Bull Math Biol., 46(4), 1984, 515-27.
Williams, et al., "Control of drosophila wing and haltere development by the nuclear vestigial gene product", Genes Dev., 5(12b), Dec. 1991, 2481-2495.
Witte, et al., "Clostripain linker deletion variants yield active enzyme in *Escherichia coli*: a possible function of the linker peptide as intramolecular inhibitor of clostripain automaturation", Current Microbiology, vol. 22, No. 5, Nov. 1996, 281-286.

Witte, et al. "Heterologous expression of the clostripain gene from *Slostridium histolyticum* in *Escherichia coli* and *Bacillus subtillis*: maturation of the clostripain precursor is coupled with self-activation", Microbiology, 140, 1994, 1175-1182.
Written Opinion issued in International Application No. PCT/IB2004/004439 mailed Sep. 23, 2005.
Zhan, et al., "Structural analysis of regulatory protein domains using GST-fusion proteins", GENE: An International Journal on Genes and Genomes, 281(1-2), 2001 Elsevier Science B.V., Dec. 27, 2001, 1-9.
Zhao, et al., "Formation of mRNA 3' ends in eukaryotes: mechanism, regulation, and interrelationships with other steps in mRNA synthesis", Microbiol. Mol. Biol. Rev., 63(2), Jun. 1999, 405-45.
Zhu, et al. "Site-specific hydrolytic cleavage of cytochrome c and of its heme undecapeptide, promoted by coordinated complexes of palladium(II)", J. Am. Chem. Soc., 116, 1994, 5218-5224.

* cited by examiner

SEQUENCE LISTING

<160> NUMBER OF SEQ ID NOS: 55

<210> SEQ ID NO 1
<211> LENGTH: 34
<212> TYPE: PRT
<213> ORGANISM: Artificial Sequence
<220> FEATURE:
<223> OTHER INFORMATION: A synthetic peptide

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg

<210> SEQ ID NO 2
<211> LENGTH: 33
<212> TYPE: PRT
<213> ORGANISM: Artificial Sequence
<220> FEATURE:
<223> OTHER INFORMATION: A synthetic peptide

<400> SEQUENCE: 2

Ala Asp Gly Ser Phe Ser Asp Glu Met Asn Thr Ile Leu Asp Asn Leu
1               5                   10                  15

Ala Ala Arg Asp Phe Ile Asn Trp Leu Ile Gln Thr Lys Ile Thr Asp
            20                  25                  30

Arg

<210> SEQ ID NO 3
<211> LENGTH: 32
<212> TYPE: PRT
<213> ORGANISM: Artificial Sequence
<220> FEATURE:
<223> OTHER INFORMATION: A synthetic peptide

<400> SEQUENCE: 3

Asp Gly Ser Phe Ser Asp Glu Met Asn Thr Ile Leu Asp Asn Leu Ala
1               5                   10                  15

Ala Arg Asp Phe Ile Asn Trp Leu Ile Gln Thr Lys Ile Thr Asp Arg
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: A synthetic peptide

<400> SEQUENCE: 4

Gly Ser Phe Ser Asp Glu Met Asn Thr Ile Leu Asp Asn Leu Ala Ala
1               5                   10                  15

Arg Asp Phe Ile Asn Trp Leu Ile Gln Thr Lys Ile Thr Asp Arg
            20                  25                  30

<210> SEQ ID NO 5
<211> LENGTH: 29
<212> TYPE: PRT
<213> ORGANISM: Artificial Sequence
<220> FEATURE:
<223> OTHER INFORMATION: A synthetic peptide -continued

```
<400> SEQUENCE: 5

Phe Ser Asp Glu Met Asn Thr Ile Leu Asp Asn Leu Ala Ala Arg Asp
1               5                   10                  15

Phe Ile Asn Trp Leu Ile Gln Thr Lys Ile Thr Asp Arg
            20                  25

<210> SEQ ID NO 6
<211> LENGTH: 28
<212> TYPE: PRT
<213> ORGANISM: Artificial Sequence
<220> FEATURE:
<223> OTHER INFORMATION: A synthetic peptide

<400> SEQUENCE: 6

Ser Asp Glu Met Asn Thr Ile Leu Asp Asn Leu Ala Ala Arg Asp Phe
1               5                   10                  15

Ile Asn Trp Leu Ile Gln Thr Lys Ile Thr Asp Arg
            20                  25

<210> SEQ ID NO 7
<211> LENGTH: 32
<212> TYPE: PRT
<213> ORGANISM: Artificial Sequence
<220> FEATURE:
<223> OTHER INFORMATION: A synthetic peptide

<400> SEQUENCE: 7

Asp Gly Ser Phe Ser Asp Glu Met Asn Thr Ile Leu Asp Asn Leu Ala
1               5                   10                  15

Ala Arg Asp Phe Ile Asn Trp Leu Ile Gln Thr Lys Ile Thr Asp Arg
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: A synthetic peptide

<400> SEQUENCE: 8

Gly Ser Phe Ser Asp Glu Met Asn Thr Ile Leu Asp Asn Leu Ala Ala
1               5                   10                  15

Arg Asp Phe Ile Asn Trp Leu Ile Gln Thr Lys Ile Thr Asp Arg
            20                  25                  30

<210> SEQ ID NO 9
<211> LENGTH: 34
<212> TYPE: PRT
<213> ORGANISM: Artificial Sequence
<220> FEATURE:
<223> OTHER INFORMATION: A synthetic peptide

<400> SEQUENCE: 9

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg

<210> SEQ ID NO 10
<211> LENGTH: 34
<212> TYPE: PRT
<213> ORGANISM: Artificial Sequence
<220> FEATURE:
```

-continued

```
<223> OTHER INFORMATION: A synthetic peptide
<220> FEATURE:
<221> NAME/KEY: MISC_FEATURE
<222> LOCATION: (34)..(34)
<223> OTHER INFORMATION: Xaa is Arg-NH2

<400> SEQUENCE: 10

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Xaa

<210> SEQ ID NO 11
<211> LENGTH: 33
<212> TYPE: PRT
<213> ORGANISM: Artificial Sequence
<220> FEATURE:
<223> OTHER INFORMATION: A synthetic peptide

<400> SEQUENCE: 11

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 12
<211> LENGTH: 33
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (33)..(33)
<223> OTHER INFORMATION: Xaa is Asp-NH2

<400> SEQUENCE: 12

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Xaa

<210> SEQ ID NO 13
<211> LENGTH: 33
<212> TYPE: PRT
<213> ORGANISM: Artificial Sequence
<220> FEATURE:
<223> OTHER INFORMATION: A synthetic peptide

<400> SEQUENCE: 13

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 14
<211> LENGTH: 33
<212> TYPE: PRT
<213> ORGANISM: Artificial Sequence
<220> FEATURE:
```

```
<223> OTHER INFORMATION: A synthetic peptide
<220> FEATURE:
<221> NAME/KEY: MISC_FEATURE
<222> LOCATION: (33)..(33)
<223> OTHER INFORMATION: Xaa is ASP-NH2

<400> SEQUENCE: 14

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Xaa

<210> SEQ ID NO 15
<211> LENGTH: 34
<212> TYPE: PRT
<213> ORGANISM: Artificial Sequence
<220> FEATURE:
<223> OTHER INFORMATION: A synthetic peptide

<400> SEQUENCE: 15

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg

<210> SEQ ID NO 16
<211> LENGTH: 34
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (34)..(34)
<223> OTHER INFORMATION: Xaa is Arg-NH2

<400> SEQUENCE: 16

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Xaa

<210> SEQ ID NO 17
<211> LENGTH: 11
<212> TYPE: PRT
<213> ORGANISM: Artificial Sequence
<220> FEATURE:
<223> OTHER INFORMATION: A synthetic T7 tag

<400> SEQUENCE: 17

Ala Ser Met Thr Gly Gly Gln Gln Met Gly Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: A synthetic T7 tag

<400> SEQUENCE: 18

Met Ala Ser Met Thr Gly Gly Gln Gln Met Gly Arg
```

```
                 1               5                   10
```

<210> SEQ ID NO 19
<211> LENGTH: 29
<212> TYPE: PRT
<213> ORGANISM: Artificial Sequence
<220> FEATURE:
<223> OTHER INFORMATION: A synthetic inclusion body leader partner

<400> SEQUENCE: 19

```
Gly Ser Gly Gln Gly Gln Ala Gln Tyr Leu Ser Ala Ser Cys Val Val
1               5                   10                  15

Phe Thr Asn Tyr Ser Gly Asp Thr Ala Ser Gln Val Asp
            20                  25
```

<210> SEQ ID NO 20
<211> LENGTH: 38
<212> TYPE: PRT
<213> ORGANISM: Artificial Sequence
<220> FEATURE:
<223> OTHER INFORMATION: A synthetic inclusion body leader partner that
      is part of the Drosophila vestigial polypeptide (Vg)

<400> SEQUENCE: 20

```
Gly Ser Gly Gln Gly Gln Ala Gln Tyr Leu Ala Ala Ser Leu Val Val
1               5                   10                  15

Phe Thr Asn Tyr Ser Gly Asp Thr Ala Ser Gln Val Asp Val Asn Gly
            20                  25                  30

Pro Arg Ala Met Val Asp
        35
```

<210> SEQ ID NO 21
<211> LENGTH: 35
<212> TYPE: PRT
<213> ORGANISM: Artificial Sequence
<220> FEATURE:
<223> OTHER INFORMATION: A synthetic inclusion body leader partner that
      is part of polyhedrin polypeptide (Ph)

<400> SEQUENCE: 21

```
Gly Ser Ala Glu Glu Glu Glu Ile Leu Leu Glu Val Ser Leu Val Phe
1               5                   10                  15

Lys Val Lys Glu Phe Ala Pro Asp Ala Pro Leu Phe Thr Gly Pro Ala
            20                  25                  30

Tyr Val Asp
        35
```

<210> SEQ ID NO 22
<211> LENGTH: 22
<212> TYPE: PRT
<213> ORGANISM: Artificial Sequence
<220> FEATURE:
<223> OTHER INFORMATION: A synthetic inclusion body leader partner that
      includes part of the lactamase polypeptide

<400> SEQUENCE: 22

```
Ser Ile Gln His Phe Arg Val Ala Leu Ile Pro Phe Phe Ala Ala Phe
1               5                   10                  15

Ser Leu Pro Val Phe Ala
            20
```

<210> SEQ ID NO 23
<211> LENGTH: 8
<212> TYPE: PRT
<213> ORGANISM: Artificial Sequence

```
<220> FEATURE:
<223> OTHER INFORMATION: A synthetic cleavable peptide linker sequence

<400> SEQUENCE: 23

Ala Phe Leu Gly Pro Gly Asp Arg
1               5

<210> SEQ ID NO 24
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 24

Val Asp Asp Arg
1

<210> SEQ ID NO 25
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 25

Gly Ser Asp Arg
1

<210> SEQ ID NO 26
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 26

Ile Thr Asp Arg
1

<210> SEQ ID NO 27
<211> LENGTH: 4
<212> TYPE: PRT
<213> ORGANISM: Artificial Sequence
<220> FEATURE:
<223> OTHER INFORMATION: A synthetic cleavable peptide linker sequence

<400> SEQUENCE: 27

Pro Gly Asp Arg
1

<210> SEQ ID NO 28
<211> LENGTH: 49
<212> TYPE: PRT
<213> ORGANISM: Artificial Sequence
<220> FEATURE:
<223> OTHER INFORMATION: A synthetic peptide

<400> SEQUENCE: 28

Met Ala Ser Met Thr Gly Gly Gln Gln Met Gly Arg Gly Ser Asp Arg
1               5                   10                  15

His Ala Asp Gly Ser Phe Ser Asp Glu Met Asn Thr Ile Leu Asp Asn
                20                  25                  30

Leu Ala Ala Arg Asp Phe Ile Asn Trp Leu Ile Gln Thr Lys Ile Thr
            35                  40                  45

Asp
```

<210> SEQ ID NO 29
<211> LENGTH: 220
<212> TYPE: PRT
<213> ORGANISM: Artificial Sequence
<220> FEATURE:
<223> OTHER INFORMATION: A synthetic peptide

<400> SEQUENCE: 29

Met Ala Ser Met Thr Gly Gly Gln Gln Met Gly Arg Gly Ser Asp Arg
1               5                   10                  15

His Ala Asp Gly Ser Phe Ser Asp Glu Met Asn Thr Ile Leu Asp Asn
            20                  25                  30

Leu Ala Ala Arg Asp Phe Ile Asn Trp Leu Ile Gln Thr Lys Ile Thr
        35                  40                  45

Asp Arg His Ala Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp Arg His Ala Asp Gly Ser Phe Ser Asp Glu Met Asn Thr
                85                  90                  95

Ile Leu Asp Asn Leu Ala Ala Arg Asp Phe Ile Asn Trp Leu Ile Gln
            100                 105                 110

Thr Lys Ile Thr Asp Arg His Ala Asp Gly Ser Phe Ser Asp Glu Met
        115                 120                 125

Asn Thr Ile Leu Asp Asn Leu Ala Ala Arg Asp Phe Ile Asn Trp Leu
    130                 135                 140

Ile Gln Thr Lys Ile Thr Asp Arg His Ala Asp Gly Ser Phe Ser Asp
145                 150                 155                 160

Glu Met Asn Thr Ile Leu Asp Asn Leu Ala Ala Arg Asp Phe Ile Asn
                165                 170                 175

Trp Leu Ile Gln Thr Lys Ile Thr Asp Arg His Ala Asp Gly Ser Phe
            180                 185                 190

Ser Asp Glu Met Asn Thr Ile Leu Asp Asn Leu Ala Ala Arg Asp Phe
        195                 200                 205

Ile Asn Trp Leu Ile Gln Thr Lys Ile Thr Asp Arg
    210                 215                 220

<210> SEQ ID NO 30
<211> LENGTH: 28
<212> TYPE: PRT
<213> ORGANISM: Artificial Sequence
<220> FEATURE:
<223> OTHER INFORMATION: A synthetic peptide

<400> SEQUENCE: 30

Ser Asp Glu Met Asn Thr Ile Leu Asp Asn Leu Ala Ala Arg Asp Phe
1               5                   10                  15

Ile Asn Trp Leu Ile Gln Thr Lys Ile Thr Asp Arg
            20                  25

<210> SEQ ID NO 31
<211> LENGTH: 26
<212> TYPE: PRT
<213> ORGANISM: Artificial Sequence
<220> FEATURE:
<223> OTHER INFORMATION: A synthetic peptide

<400> SEQUENCE: 31

Glu Met Asn Thr Ile Leu Asp Asn Leu Ala Ala Arg Asp Phe Ile Asn

```
1               5                  10                 15

Trp Leu Ile Gln Thr Lys Ile Thr Asp Arg
            20                  25

<210> SEQ ID NO 32
<211> LENGTH: 22
<212> TYPE: PRT
<213> ORGANISM: Artificial Sequence
<220> FEATURE:
<223> OTHER INFORMATION: A synthetic peptide

<400> SEQUENCE: 32

Ile Leu Asp Asn Leu Ala Ala Arg Asp Phe Ile Asn Trp Leu Ile Gln
1               5                   10                  15

Thr Lys Ile Thr Asp Arg
            20

<210> SEQ ID NO 33
<211> LENGTH: 19
<212> TYPE: PRT
<213> ORGANISM: Artificial Sequence
<220> FEATURE:
<223> OTHER INFORMATION: A synthetic peptide

<400> SEQUENCE: 33

Asn Leu Ala Ala Arg Asp Phe Ile Asn Trp Leu Ile Gln Thr Lys Ile
1               5                   10                  15

Thr Asp Arg

<210> SEQ ID NO 34
<211> LENGTH: 4
<212> TYPE: PRT
<213> ORGANISM: Artificial Sequence
<220> FEATURE:
<223> OTHER INFORMATION: A synthetic peptide

<400> SEQUENCE: 34

Cys His Asp Arg
1

<210> SEQ ID NO 35
<211> LENGTH: 4
<212> TYPE: PRT
<213> ORGANISM: Artificial Sequence
<220> FEATURE:
<223> OTHER INFORMATION: A synthetic peptide

<400> SEQUENCE: 35

Gly Ser Glu Arg
1

<210> SEQ ID NO 36
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (3)..(4)
<223> OTHER INFORMATION: Xaa = any amino acid

<400> SEQUENCE: 36

Cys His Xaa Xaa Asp Arg
1               5
```

```
<210> SEQ ID NO 37
<211> LENGTH: 219
<212> TYPE: PRT
<213> ORGANISM: Artificial Sequence
<220> FEATURE:
<223> OTHER INFORMATION: A synthetic peptide

<400> SEQUENCE: 37

Ala Ser Met Thr Gly Gly Gln Gln Met Gly Arg Gly Ser Asp Arg His
1               5                   10                  15

Ala Asp Gly Ser Phe Ser Asp Glu Met Asn Thr Ile Leu Asp Asn Leu
            20                  25                  30

Ala Ala Arg Asp Phe Ile Asn Trp Leu Ile Gln Thr Lys Ile Thr Asp
        35                  40                  45

Arg His Ala Asp Gly Ser Phe Ser Asp Glu Met Asn Thr Ile Leu Asp
    50                  55                  60

Asn Leu Ala Ala Arg Asp Phe Ile Asn Trp Leu Ile Gln Thr Lys Ile
65                  70                  75                  80

Thr Asp Arg His Ala Asp Gly Ser Phe Ser Asp Glu Met Asn Thr Ile
                85                  90                  95

Leu Asp Asn Leu Ala Ala Arg Asp Phe Ile Asn Trp Leu Ile Gln Thr
            100                 105                 110

Lys Ile Thr Asp Arg His Ala Asp Gly Ser Phe Ser Asp Glu Met Asn
        115                 120                 125

Thr Ile Leu Asp Asn Leu Ala Ala Arg Asp Phe Ile Asn Trp Leu Ile
    130                 135                 140

Gln Thr Lys Ile Thr Asp Arg His Ala Asp Gly Ser Phe Ser Asp Glu
145                 150                 155                 160

Met Asn Thr Ile Leu Asp Asn Leu Ala Ala Arg Asp Phe Ile Asn Trp
                165                 170                 175

Leu Ile Gln Thr Lys Ile Thr Asp Arg His Ala Asp Gly Ser Phe Ser
            180                 185                 190

Asp Glu Met Asn Thr Ile Leu Asp Asn Leu Ala Ala Arg Asp Phe Ile
        195                 200                 205

Asn Trp Leu Ile Gln Thr Lys Ile Thr Asp Arg
    210                 215

<210> SEQ ID NO 38
<211> LENGTH: 89
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (89)..(89)
<223> OTHER INFORMATION: Xaa = any amino acid

<400> SEQUENCE: 38

Ala Ser Met Thr Gly Gly Gln Gln Met Gly Arg Gly Ser Gly Gln Gly
1               5                   10                  15

Gln Ala Gln Tyr Leu Ala Ala Ser Leu Val Val Phe Thr Asn Tyr Ser
            20                  25                  30

Gly Asp Thr Ala Ser Gln Val Asp Val Asn Gly Pro Arg Ala Met Val
        35                  40                  45

Asp Val Asp Asp Arg His Gly Asp Gly Ser Phe Ser Asp Glu Met Asn
    50                  55                  60

Thr Ile Leu Asp Asn Leu Ala Ala Arg Asp Phe Ile Asn Trp Leu Ile
65                  70                  75                  80
```

Gln Thr Lys Ile Thr Asp Pro Tyr Xaa
                85

<210> SEQ ID NO 39
<211> LENGTH: 85
<212> TYPE: PRT
<213> ORGANISM: Artificial Sequence
<220> FEATURE:
<223> OTHER INFORMATION: A synthetic peptide

<400> SEQUENCE: 39

Ala Ser Met Thr Gly Gly Gln Gln Met Gly Arg Gly Ser Asp Arg His
1               5                   10                  15

Gly Asp Gly Ser Phe Ser Asp Gly Met Asn Thr Ile Leu Asp Asn Leu
            20                  25                  30

Ala Ala Arg Asp Phe Ile Asn Trp Leu Ile Gln Thr Lys Ile Thr Asp
        35                  40                  45

Pro Gly Asp Arg His Gly Asp Gly Ser Phe Ser Asp Glu Met Asn Thr
    50                  55                  60

Ile Leu Asp Asn Leu Ala Ala Arg Asp Phe Ile Asn Trp Leu Ile Gln
65                  70                  75                  80

Thr Lys Ile Thr Asp
                85

<210> SEQ ID NO 40
<211> LENGTH: 86
<212> TYPE: PRT
<213> ORGANISM: Artificial Sequence
<220> FEATURE:
<223> OTHER INFORMATION: A synthetic peptide

<400> SEQUENCE: 40

Ala Ser Met Thr Gly Gly Gln Gln Met Gly Arg Gly Ser Gly Gln Gly
1               5                   10                  15

Gln Ala Gln Tyr Leu Ala Ala Ser Leu Val Val Phe Thr Asn Tyr Ser
            20                  25                  30

Gly Asp Thr Ala Ser Gln Val Asp Val Asn Gly Pro Arg Ala Met Val
        35                  40                  45

Asp Val Asp Asp Arg His Gly Asp Gly Ser Phe Ser Asp Glu Met Asn
    50                  55                  60

Thr Ile Leu Asp Asn Leu Ala Ala Arg Asp Phe Ile Asn Trp Leu Ile
65                  70                  75                  80

Gln Thr Lys Ile Thr Asp
                85

<210> SEQ ID NO 41
<211> LENGTH: 37
<212> TYPE: PRT
<213> ORGANISM: Artificial Sequence
<220> FEATURE:
<223> OTHER INFORMATION: A synthetic peptide

<400> SEQUENCE: 41

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Pro Gly Asp Arg
            35

<210> SEQ ID NO 42

```
<211> LENGTH: 39
<212> TYPE: PRT
<213> ORGANISM: Artificial Sequence
<220> FEATURE:
<223> OTHER INFORMATION: A synthetic peptide

<400> SEQUENCE: 42

Ala Met Val Asp Asp Arg His Gly Asp Gly Ser Phe Ser Asp Glu Met
1               5                   10                  15

Asn Thr Ile Leu Asp Asn Leu Ala Ala Arg Asp Phe Ile Asn Trp Leu
            20                  25                  30

Ile Gln Thr Lys Ile Thr Asp
        35

<210> SEQ ID NO 43
<211> LENGTH: 73
<212> TYPE: PRT
<213> ORGANISM: Artificial Sequence
<220> FEATURE:
<223> OTHER INFORMATION: A synthetic peptide

<400> SEQUENCE: 43

Gly Ser Gly Gln Gly Gln Ala Gln Tyr Leu Ala Ser Leu Val Val
1               5                   10                  15

Phe Thr Asn Tyr Ser Gly Asp Thr Ala Ser Gln Val Asp Val Val Gly
            20                  25                  30

Pro Arg Ala Met Val Asp Asp Arg His Gly Asp Gly Ser Phe Ser Asp
        35                  40                  45

Glu Met Asn Thr Ile Leu Asp Asn Leu Ala Ala Arg Asp Phe Ile Asn
    50                  55                  60

Trp Leu Ile Gln Thr Lys Ile Thr Asp
65                  70

<210> SEQ ID NO 44
<211> LENGTH: 49
<212> TYPE: PRT
<213> ORGANISM: Artificial Sequence
<220> FEATURE:
<223> OTHER INFORMATION: A synthetic peptide

<400> SEQUENCE: 44

Ala Ser Met Thr Gly Gly Gln Gln Met Gly Arg Gly Ser Asp Arg Gly
1               5                   10                  15

His Gly Asp Gly Ser Phe Ser Asp Glu Met Asn Thr Ile Leu Asp Asn
            20                  25                  30

Leu Ala Ala Arg Asp Phe Ile Asn Trp Leu Ile Gln Thr Lys Ile Thr
        35                  40                  45

Asp

<210> SEQ ID NO 45
<211> LENGTH: 219
<212> TYPE: PRT
<213> ORGANISM: Artificial Sequence
<220> FEATURE:
<223> OTHER INFORMATION: A synthetic peptide

<400> SEQUENCE: 45

Ala Ser Met Thr Gly Gly Gln Gln Met Gly Arg Gly Ser Asp Arg His
1               5                   10                  15

Ala Asp Gly Ser Phe Ser Asp Glu Leu Asn Thr Ile Leu Asp Asn Leu
            20                  25                  30

Ala Ala Arg Asp Phe Ile Asn Trp Leu Ile Gln Thr Lys Ile Thr Asp
```

```
                    35                  40                  45
Arg His Ala Asp Gly Ser Phe Ser Asp Glu Leu Asn Thr Ile Leu Asp
 50                  55                  60
Asn Leu Ala Ala Arg Asp Phe Ile Asn Trp Leu Ile Gln Thr Lys Ile
 65                  70                  75                  80
Thr Asp Arg His Ala Asp Gly Ser Phe Ser Asp Glu Leu Asn Thr Ile
                     85                  90                  95
Leu Asp Asn Leu Ala Ala Arg Asp Phe Ile Asn Trp Leu Ile Gln Thr
                100                 105                 110
Lys Ile Thr Asp Arg His Ala Asp Gly Ser Phe Ser Asp Glu Leu Asn
            115                 120                 125
Thr Ile Leu Asp Asn Leu Ala Ala Arg Asp Phe Ile Asn Trp Leu Ile
        130                 135                 140
Gln Thr Lys Ile Thr Asp Arg His Ala Asp Gly Ser Phe Ser Asp Glu
145                 150                 155                 160
Leu Asn Thr Ile Leu Asp Asn Leu Ala Ala Arg Asp Phe Ile Asn Trp
                165                 170                 175
Leu Ile Gln Thr Lys Ile Thr Asp Arg His Ala Asp Gly Ser Phe Ser
            180                 185                 190
Asp Glu Leu Asn Thr Ile Leu Asp Asn Leu Ala Ala Arg Asp Phe Ile
        195                 200                 205
Asn Trp Leu Ile Gln Thr Lys Ile Thr Asp Arg
    210                 215

<210> SEQ ID NO 46
<211> LENGTH: 219
<212> TYPE: PRT
<213> ORGANISM: Artificial Sequence
<220> FEATURE:
<223> OTHER INFORMATION: A synthetic peptide

<400> SEQUENCE: 46

Ala Ser Met Thr Gly Gly Gln Gln Met Gly Arg Gly Ser Asp Arg His
  1               5                  10                  15
Gly Asp Gly Ser Phe Ser Asp Glu Met Asn Thr Ile Leu Asp Asn Leu
                 20                  25                  30
Ala Ala Arg Asp Phe Ile Asn Trp Leu Ile Gln Thr Lys Ile Thr Asp
             35                  40                  45
Arg His Gly Asp Gly Ser Phe Ser Asp Glu Met Asn Thr Ile Leu Asp
 50                  55                  60
Asn Leu Ala Ala Arg Asp Phe Ile Asn Trp Leu Ile Gln Thr Lys Ile
 65                  70                  75                  80
Thr Asp Arg His Gly Asp Gly Ser Phe Ser Asp Glu Met Asn Thr Ile
                     85                  90                  95
Leu Asp Asn Leu Ala Ala Arg Asp Phe Ile Asn Trp Leu Ile Gln Thr
                100                 105                 110
Lys Ile Thr Asp Arg His Gly Asp Gly Ser Phe Ser Asp Glu Met Asn
            115                 120                 125
Thr Ile Leu Asp Asn Leu Ala Ala Arg Asp Phe Ile Asn Trp Leu Ile
        130                 135                 140
Gln Thr Lys Ile Thr Asp Arg His Gly Asp Gly Ser Phe Ser Asp Glu
145                 150                 155                 160
Met Asn Thr Ile Leu Asp Asn Leu Ala Ala Arg Asp Phe Ile Asn Trp
                165                 170                 175
Leu Ile Gln Thr Lys Ile Thr Asp Arg His Gly Asp Gly Ser Phe Ser
            180                 185                 190
```

Asp Glu Met Asn Thr Ile Leu Asp Asn Leu Ala Ala Arg Asp Phe Ile
        195                 200                 205

Asn Trp Leu Ile Gln Thr Lys Ile Thr Asp Arg
        210                 215

<210> SEQ ID NO 47
<211> LENGTH: 81
<212> TYPE: PRT
<213> ORGANISM: Artificial Sequence
<220> FEATURE:
<223> OTHER INFORMATION: A synthetic peptide

<400> SEQUENCE: 47

Ala Ser Met Thr Gly Gly Gln Gln Met Gly Arg His Gly Asp Gly Ser
1               5                   10                  15

Phe Ser Asp Glu Met Asn Thr Ile Leu Asp Asn Leu Ala Ala Arg Asp
                20                  25                  30

Phe Ile Asn Trp Leu Ile Gln Thr Lys Ile Thr Asp Gly Pro Asp Arg
            35                  40                  45

His Ala Asp Gly Ser Phe Ser Asp Glu Leu Asn Thr Ile Leu Asp Asn
        50                  55                  60

Leu Ala Ala Arg Asp Phe Ile Asn Trp Leu Ile Gln Thr Lys Ile Thr
65                  70                  75                  80

Asp

<210> SEQ ID NO 48
<211> LENGTH: 220
<212> TYPE: PRT
<213> ORGANISM: Artificial Sequence
<220> FEATURE:
<223> OTHER INFORMATION: A synthetic peptide

<400> SEQUENCE: 48

Met Ala Ser Met Thr Gly Gly Gln Gln Met Gly Arg Gly Ser Asp Arg
1               5                   10                  15

His Ala Asp Gly Ser Phe Ser Asp Glu Met Asn Thr Ile Leu Asp Asn
                20                  25                  30

Leu Ala Ala Arg Asp Phe Ile Asn Trp Leu Ile Gln Thr Lys Ile Thr
            35                  40                  45

Asp Arg His Ala Asp Gly Ser Phe Ser Asp Glu Met Asn Thr Ile Leu
        50                  55                  60

Asp Asn Leu Ala Ala Arg Asp Phe Ile Asn Trp Leu Ile Gln Thr Lys
65                  70                  75                  80

Ile Thr Asp Arg His Ala Asp Gly Ser Phe Ser Asp Glu Met Asn Thr
                85                  90                  95

Ile Leu Asp Asn Leu Ala Ala Arg Asp Phe Ile Asn Trp Leu Ile Gln
            100                 105                 110

Thr Lys Ile Thr Asp Arg His Ala Asp Gly Ser Phe Ser Asp Glu Met
        115                 120                 125

Asn Thr Ile Leu Asp Asn Leu Ala Ala Arg Asp Phe Ile Asn Trp Leu
    130                 135                 140

Ile Gln Thr Lys Ile Thr Asp Arg His Ala Asp Gly Ser Phe Ser Asp
145                 150                 155                 160

Glu Met Asn Thr Ile Leu Asp Asn Leu Ala Ala Arg Asp Phe Ile Asn
                165                 170                 175

Trp Leu Ile Gln Thr Lys Ile Thr Asp Arg His Ala Asp Gly Ser Phe
            180                 185                 190

```
Ser Asp Glu Met Asn Thr Ile Leu Asp Asn Leu Ala Ala Arg Asp Phe
        195                 200                 205

Ile Asn Trp Leu Ile Gln Thr Lys Ile Thr Asp Arg
    210                 215                 220

<210> SEQ ID NO 49
<211> LENGTH: 90
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (90)..(90)
<223> OTHER INFORMATION: Xaa = any amino acid

<400> SEQUENCE: 49

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Val Asp Asp Arg His Gly Asp Gly Ser Phe Ser Asp Glu Met
    50                  55                  60

Asn Thr Ile Leu Asp Asn Leu Ala Ala Arg Asp Phe Ile Asn Trp Leu
65                  70                  75                  80

Ile Gln Thr Lys Ile Thr Asp Pro Tyr Xaa
                85                  90

<210> SEQ ID NO 50
<211> LENGTH: 86
<212> TYPE: PRT
<213> ORGANISM: Artificial Sequence
<220> FEATURE:
<223> OTHER INFORMATION: A synthetic peptide

<400> SEQUENCE: 50

Met Ala Ser Met Thr Gly Gly Gln Gln Met Gly Arg Gly Ser Asp Arg
1               5                   10                  15

His Gly Asp Gly Ser Phe Ser Asp Glu Met Asn Thr Ile Leu Asp Asn
            20                  25                  30

Leu Ala Ala Arg Asp Phe Ile Asn Trp Leu Ile Gln Thr Lys Ile Thr
        35                  40                  45

Asp Pro Gly Asp Arg His Gly Asp Gly Ser Phe Ser Asp Glu Met Asn
    50                  55                  60

Thr Ile Leu Asp Asn Leu Ala Ala Arg Asp Phe Ile Asn Trp Leu Ile
65                  70                  75                  80

Gln Thr Lys Ile Thr Asp
                85

<210> SEQ ID NO 51
<211> LENGTH: 87
<212> TYPE: PRT
<213> ORGANISM: Artificial Sequence
<220> FEATURE:
<223> OTHER INFORMATION: A synthetic peptide

<400> SEQUENCE: 51

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
```

```
                    20                  25                  30
Ser Gly Asp Thr Ala Ser Gln Val Asp Val Asn Gly Pro Arg Ala Met
        35                  40                  45

Val Asp Val Asp Asp Arg His Gly Asp Gly Ser Phe Ser Asp Glu Met
    50                  55                  60

Asn Thr Ile Leu Asp Asn Leu Ala Ala Arg Asp Phe Ile Asn Trp Leu
65                  70                  75                  80

Ile Gln Thr Lys Ile Thr Asp
                85

<210> SEQ ID NO 52
<211> LENGTH: 50
<212> TYPE: PRT
<213> ORGANISM: Artificial Sequence
<220> FEATURE:
<223> OTHER INFORMATION: A synthetic peptide

<400> SEQUENCE: 52

Met Ala Ser Met Thr Gly Gly Gln Gln Met Gly Arg Gly Ser Asp Arg
1               5                   10                  15

Gly His Gly Asp Gly Ser Phe Ser Asp Glu Met Asn Thr Ile Leu Asp
                20                  25                  30

Asn Leu Ala Ala Arg Asp Phe Ile Asn Trp Leu Ile Gln Thr Lys Ile
            35                  40                  45

Thr Asp
    50

<210> SEQ ID NO 53
<211> LENGTH: 220
<212> TYPE: PRT
<213> ORGANISM: Artificial Sequence
<220> FEATURE:
<223> OTHER INFORMATION: A synthetic peptide

<400> SEQUENCE: 53

Met Ala Ser Met Thr Gly Gly Gln Gln Met Gly Arg Gly Ser Asp Arg
1               5                   10                  15

His Ala Asp Gly Ser Phe Ser Asp Glu Met Asn Thr Ile Leu Asp Asn
                20                  25                  30

Leu Ala Ala Arg Asp Phe Ile Asn Trp Leu Ile Gln Thr Lys Ile Thr
            35                  40                  45

Asp Arg His Ala Asp Gly Ser Phe Ser Asp Glu Met Asn Thr Ile Leu
        50                  55                  60

Asp Asn Leu Ala Ala Arg Asp Phe Ile Asn Trp Leu Ile Gln Thr Lys
65                  70                  75                  80

Ile Thr Asp Arg His Ala Asp Gly Ser Phe Ser Asp Glu Met Asn Thr
                85                  90                  95

Ile Leu Asp Asn Leu Ala Ala Arg Asp Phe Ile Asn Trp Leu Ile Gln
            100                 105                 110

Thr Lys Ile Thr Asp Arg His Ala Asp Gly Ser Phe Ser Asp Glu Met
        115                 120                 125

Asn Thr Ile Leu Asp Asn Leu Ala Ala Arg Asp Phe Ile Asn Trp Leu
    130                 135                 140

Ile Gln Thr Lys Ile Thr Asp Arg His Ala Asp Gly Ser Phe Ser Asp
145                 150                 155                 160

Glu Met Asn Thr Ile Leu Asp Asn Leu Ala Ala Arg Asp Phe Ile Asn
                165                 170                 175

Trp Leu Ile Gln Thr Lys Ile Thr Asp Arg His Ala Asp Gly Ser Phe
```

```
              180              185              190

Ser Asp Glu Met Asn Thr Ile Leu Asp Asn Leu Ala Ala Arg Asp Phe
        195                 200                 205

Ile Asn Trp Leu Ile Gln Thr Lys Ile Thr Asp Arg
    210                 215                 220

<210> SEQ ID NO 54
<211> LENGTH: 220
<212> TYPE: PRT
<213> ORGANISM: Artificial Sequence
<220> FEATURE:
<223> OTHER INFORMATION: A synthetic peptide

<400> SEQUENCE: 54

Met Ala Ser Met Thr Gly Gly Gln Gln Met Gly Arg Gly Ser Asp Arg
1               5                   10                  15

His Gly Asp Gly Ser Phe Ser Asp Glu Met Asn Thr Ile Leu Asp Asn
            20                  25                  30

Leu Ala Ala Arg Asp Phe Ile Asn Trp Leu Ile Gln Thr Lys Ile Thr
        35                  40                  45

Asp Arg His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp Arg His Gly Asp Gly Ser Phe Ser Asp Glu Met Asn Thr
                85                  90                  95

Ile Leu Asp Asn Leu Ala Ala Arg Asp Phe Ile Asn Trp Leu Ile Gln
            100                 105                 110

Thr Lys Ile Thr Asp Arg His Gly Asp Gly Ser Phe Ser Asp Glu Met
        115                 120                 125

Asn Thr Ile Leu Asp Asn Leu Ala Ala Arg Asp Phe Ile Asn Trp Leu
    130                 135                 140

Ile Gln Thr Lys Ile Thr Asp Arg His Gly Asp Gly Ser Phe Ser Asp
145                 150                 155                 160

Glu Met Asn Thr Ile Leu Asp Asn Leu Ala Ala Arg Asp Phe Ile Asn
                165                 170                 175

Trp Leu Ile Gln Thr Lys Ile Thr Asp Arg His Gly Asp Gly Ser Phe
            180                 185                 190

Ser Asp Glu Met Asn Thr Ile Leu Asp Asn Leu Ala Ala Arg Asp Phe
        195                 200                 205

Ile Asn Trp Leu Ile Gln Thr Lys Ile Thr Asp Arg
    210                 215                 220

<210> SEQ ID NO 55
<211> LENGTH: 82
<212> TYPE: PRT
<213> ORGANISM: Artificial Sequence
<220> FEATURE:
<223> OTHER INFORMATION: A synthetic peptide

<400> SEQUENCE: 55

Met Ala Ser Met Thr Gly Gly Gln Gln Met Gly Arg His Gly Asp Gly
1               5                   10                  15

Ser Phe Ser Asp Glu Met Asn Thr Ile Leu Asp Asn Leu Ala Ala Arg
            20                  25                  30
```

```
Asp Phe Ile Asn Trp Leu Ile Gln Thr Lys Ile Thr Asp Gly Pro Asp
        35                  40                  45

Arg His Ala Asp Gly Ser Phe Ser Asp Glu Leu Asn Thr Ile Leu Asp
    50                  55                  60

Asn Leu Ala Ala Arg Asp Phe Ile Asn Trp Leu Ile Gln Thr Lys Ile
65                  70                  75                  80

Thr Asp
```

METHOD FOR ENZYMATIC PRODUCTION OF GLP-2(1-33) AND GLP-2(1-34) PEPTIDES

This application is a divisional of U.S. patent application Ser. No. 10/997,065, now U.S. Pat. No. 7,781,567, which was a continuation under 35 U.S.C. 111(a) of PCT/US03/16649, filed on May 23, 2003 and published on Dec. 4, 2003 as WO 03/099854 A2, which claims priority under 35 U.S.C. 119(e) of U.S. Provisional Application No. 60/383,359 and 60/383,468, both filed on May 24, 2002, which applications and publication are incorporated herein by reference.

BACKGROUND OF THE INVENTION

Although bioactive peptides can be produced chemically by a variety of synthesis strategies, recombinant technology offers the potential for inexpensive, large-scale production of peptides without the use of organic solvents, highly reactive reagents or potentially toxic chemicals. However, expression of short peptides in *Escherichia coli* and other microbial systems can sometimes be problematic. For example, short peptides are often degraded by the proteolytic and metabolic enzymes present in microbial host cells. Use of a fusion protein to carry the peptide of interest may help avoid cellular degradation processes because the fusion protein is large enough to protect the peptide from proteolytic cleavage. Moreover, certain fusion proteins can direct the peptide to specific cellular compartments, i.e., cytoplasm, periplasm, inclusion bodies or media, thereby helping to avoid cellular degradation processes. However, while use of a fusion protein may solve certain problems, cleavage and purification of the peptide away from the fusion protein can give rise to a whole new set of problems.

Preparation of a peptide from a fusion protein in pure form requires that the peptide be released and recovered from the fusion protein by some mechanism. In many cases, the peptide of interest forms only a small portion of the fusion protein. For example, many peptidyl moieties are fused with β-galactosidase that has a molecular weight of about 100,000 daltons. A peptide with a molecular weight of about 3000 daltons would only form about 3% of the total mass of the fusion protein. Also, separate isolation or purification procedures (e.g., affinity purification procedures) are generally required for each type of peptide released from a fusion protein. Release of the peptide from the fusion protein generally involves use of specific chemical or enzymatic cleavage sites that link the carrier protein to the desired peptide [Forsberg et al., *Int. J. Protein Chem.*, 11:201 (1992)]. Chemical or enzymatic cleavage agents employed for such cleavages generally recognize a specific sequence. However, if that cleavage sequence is present in the peptide of interest, then a different cleavage agent must usually be employed. Use of a complex fusion partner (e.g., β-galactosidase) that may have many cleavage sites produces a complex mixture of products and complicates isolation and purification of the peptide of interest.

Chemical cleavage reagents in general recognize single or paired amino acid residues that may occur at multiple sites along the primary sequence, and therefore may be of limited utility for release of large peptides or protein domains which contain multiple internal recognition sites. However, recognition sites for chemical cleavage can be useful at the junction of short peptides and carrier proteins. Chemical cleavage reagents include cyanogen bromide, which cleaves at methionine residues [Piers et al., *Gene*, 134:7, (1993)], N-chloro succinimide [Forsberg et al., *Biofactors*, 2:105 (1989)] or BNPS-skatole [Knott et al., *Eur. J. Biochem.*, 174: 405 (1988); Dykes et al., *Eur. J. Biochem.*, 174:411 (1988)] which cleave at tryptophan residues, dilute acid which cleaves aspartyl-prolyl bonds [Gram et al., *Bio/Technology*, 12:1017 (1994); Marcus, *Int. J. Peptide Protein Res.*, 25:542 (1985)], and hydroxylamine which cleaves asparagine-glycine bonds at pH 9.0 [Moks et al., *Bio/Technology*, 5:379 (1987)].

For example, Shen describes bacterial expression of a fusion protein encoding pro-insulin and β-galactosidase within insoluble inclusion bodies where the inclusion bodies were first isolated and then solubilized with formic acid prior to cleavage with cyanogen bromide. Shen, *Proc. Nat'l. Acad. Sci. (USA)*, 281:4627 (1984). Dykes et al. describes soluble intracellular expression of a fusion protein encoding α-human atrial natriuretic peptide and chloramphenicol acetyltransferase in *E. coli* where the fusion protein was chemically cleaved with 2-(2-nitrophenylsulphenyl)-methyl-3'-bromoindolenine to release peptide. Dykes et al., *Eur. J. Biochem.*, 174:411 (1988). Ray et al. describes soluble intracellular expression in *E. coli* of a fusion protein encoding salmon calcitonin and glutathione-S-transferase where the fusion protein was cleaved with cyanogen bromide. Ray et al., *Bio/Technology*, 11:64 (1993)

Proteases can provide gentler cleavage conditions and sometimes even greater cleavage specificity than chemical cleavage reagents because a protease will often cleave a specific site defined by the flanking amino acids and the protease can often perform the cleavage under physiological conditions. For example, Schellenberger et al. describes expression of a fusion protein encoding a substance P peptide (11 amino acids) and β-galactosidase within insoluble inclusion bodies, where the inclusion bodies were first isolated and then treated with chymotrypsin to cleave the fusion protein. Schellenberger et al., *Int. J. Peptide Protein Res.*, 41:326 (1993). Pilon et al. describe soluble intracellular expression in *E. coli* of a fusion protein encoding a peptide and ubiquitin where the fusion protein was cleaved with a ubiquitin specific protease, UCH-L3. Pilon et al., *Biotechnol. Prog.*, 13:374 (1997). U.S. Pat. No. 5,595,887 to Coolidge et al. discloses generalized methods of cloning and isolating peptides. U.S. Pat. No. 5,707,826 to Wagner et al. describes an enzymatic method for modification of recombinant polypeptides.

Glucagon Like Peptide or GLP is an example of a polypeptide that can be produced by recombinant methods. GLP-1 and GLP-2 are produced in vivo by cleavage of preproglucagon to produce the two bioactive polypeptides. The original sequencing studies indicated that GLP-2 included thirty-four amino acids.

The recombinant production of any of these GLP peptides in high yield, however, is elusive because post expression manipulation using traditional methods provides poor results. Consequently, the goal of recombinant production of GLP through a one pot, high yield process lends itself to protease post-expression manipulation. Currently available processes cleavage of possible pre-GLP polypeptide substrates necessitate use of different proteases and unique conditions and/or pre-or post-manipulation of the precursor polypeptides. Hence, improved and simplified methods for making GLP peptides are needed. In particular, a simplified, high yield method for making GLP peptides is needed.

SUMMARY OF THE INVENTION

These and other needs are achieved by the present invention which is directed to a site specific clostripain cleavage of single and multicopy polypeptides having or containing a peptide sequence of the formula GLP-2(1-33), GLP-2(1-33, A2G), GLP-2 (1-34) GLP-2 (1-34,A2G) and mutations, permutations and conservative substitutions thereof (hereinafter these peptides are termed the GLP-2 peptides as a group). In particular, the present invention is directed to a method that surprisingly selects a particular clostripain cleavage site from among several that may be present in a single or multicopy polypeptide. The result of this surprising characteristic of the method of the invention is the development of a versatile procedure for wide-ranging production of desired polypeptides from single and multicopy polypeptides.

An especially preferred method according to the invention involves the production of any desired peptide through recombinant techniques. This feature is accomplished through use of a single copy polypeptide having a discardable sequence ending in arginine joined to the N-terminus of the desired peptide. The cleavage of that designated arginine according to the invention is so selective that the desired peptide may contain any sequence of amino acids. The cleavage produces a single copy of the desired peptide. Thus, the methods according to the invention enable the production of polypeptides having C-terminal acidic, aliphatic or aromatic amino acid residues and the production of a GLP-2(1-33) or GLP-2(1-34) peptide. Some of the salient details of these methods of the invention are summarized in the following passages.

The invention provides methods for making peptides using clostripain cleavage of a larger polypeptide that has at least one copy of any of the GLP-2 peptides. According to the invention, clostripain recognizes a polypeptide having a site as indicated in Formula I and cleaves a peptide bond between amino acids $Xaa_2$ and $Xaa_3$:

$$Xaa_1\text{-}Xaa_2\text{-}Xaa_3 \qquad \text{Formula I}$$

wherein $Xaa_1$ and $Xaa_3$ may be any non-acidic amino acid residue and $Xaa_2$ is arginine. According to a preferable aspect of the invention, clostripain selectively recognizes a the site as indicated in Formula I and cleaves the peptide bond between amino acids $Xaa_2$ and $Xaa_3$ wherein $Xaa_1$ is an amino acid residue with an acidic side chain such as aspartic acid, or glutamic acid, or non-acidic amino acid such as proline or glycine; $Xaa_2$ is arginine; and $Xaa_3$ is not an acidic amino acid. Also, through the control of any one or more of pH, time, temperature and reaction solvent involved in the cleavage reaction, the rate and selectivity of the clostripain cleavage may be manipulated. Thus, for example, the GLP-2(1-34) peptide of the sequence

HADGSFSDGMNTILDNLAARDFINWLIQTKITDR SEQ ID NO: 9 may be formed as multiple copies coupled together with a linker of an appropriate sequence, or multiple copies coupled together in tandem with the N-terminus (H) forming a peptide bond with the C-terminus (R) of the upstream copy, or a discardable sequence ending with $Xaa_1\text{-}Xaa_2\text{-}Xaa_3$ coupled to the N-terminus, or beginning with $Xaa_3$ coupled to the C-terminus, of the desired peptide.

Clostripain will eventually cleave the peptide bond on the carboxyl side of any arginine or lysine appearing in an amino acid sequence irrespective of the amino acid residues adjacent arginine. Surprisingly, it has been discovered that the rate of clostripain cleavage of a polypeptide can be dramatically altered by specifically altering amino acids immediately on the N-terminal and C-terminal side of an arginine residue that acts as a clostripain cleavage site. In particular, according to the invention, this preferred clostripain cleavage of an arginine amino acid residue peptide bond can be manipulated to be highly selective through use of an acidic amino acid residue bonded to the amine side of arginine, eg. $Xaa_1$ of foregoing Formula I. According to the invention, it has also been discovered that by manipulation of any one or more of pH, time, temperature and solvent character, the rate of clostripain cleavage can be manipulated to affect cleavage of a selected $Xaa_2\text{-}Xaa_3$ peptide bond of Formula I. Combinations of these factors will enable selection of particular arginine—amino acid residue bonds from among several differing such bonds that may be present in the precursor polypeptide.

In one aspect, the invention provides a method for producing a desired peptide from a polypeptide by cleaving at least one peptide bond within the polypeptide using clostripain. The clostripain cleaves a peptide bond between amino acids $Xaa_2$ and $Xaa_3$ of a polypeptide having the Formula II:

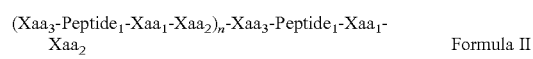

$$(Xaa_3\text{-Peptide}_1\text{-}Xaa_1\text{-}Xaa_2)_n\text{-}Xaa_3\text{-Peptide}_1\text{-}Xaa_1\text{-}Xaa_2 \qquad \text{Formula II}$$

In this aspect of the invention, the desired GLP-2 peptides have the Formula $Xaa_3\text{-Peptide}_1\text{-}Xaa_1\text{-}Xaa_2$. Also in this aspect of the invention, n is an integer ranging from 0 to 50. $Xaa_1$ is aspartic acid, glycine, proline or glutamic acid. $Xaa_2$ is arginine. $Xaa_3$ is not an acidic amino acid.

In another aspect, the invention provides a method for producing a desired peptide, such as GLP-2(1-33) or GLP-2 (1-34). Such a method involves cleaving with clostripain a peptide bond between amino acids $Xaa_2$ and $Xaa_3$ within a polypeptide comprising Formula III:

$$(\text{Linker-}Xaa_3\text{-Peptide}_1)_n\text{-Linker-}Xaa_3\text{-Peptide}_1 \qquad \text{Formula III}$$

In this aspect of the invention, the desired peptide GLP-2 has the Formula $Xaa_3\text{-Peptide}_1$. n is an integer ranging from 0 to 50. $Xaa_3$ is not an acidic amino acid. Linker is a cleavable peptide linker having Formula IV:

$$(\text{Peptide}_5)_m\text{-}Xaa_1\text{-}Xaa_2 \qquad \text{Formula IV}$$

m is an integer ranging from 0 to 50. $Xaa_1$ is aspartic acid, glycine, proline or glutamic acid. $Xaa_2$ is arginine. $Peptide_5$ is any single or multi amino acid sequence not containing the sequence $Xaa_1\text{-}Xaa_2$.

The invention further provides a method of producing a GLP-2(1-34) peptide. The method involves the steps of (a) recombinantly producing a polypeptide of the Formula VI:

$$\text{Tag-Linker-[GLP-2(1-34)]}_q \qquad \text{VI}$$

wherein Tag is a translation initiation sequence having SEQ ID NO:17 or 18; Linker is a cleavable peptide linker of Formula IV described above; GLP-2(1-34) has SEQ ID NO:9; and q is an integer of about 2 to about 20;

(b) isolating the polypeptide of Formula VI; and (c) cleaving at least one peptide bond within the polypeptide of Formula VI using clostripain, wherein clostripain cleaves a peptide bond on the C-terminal side of $Xaa_2$.

The invention also provides a method of producing a GLP-2 peptide from inclusion bodies. The method involves the steps of:

(a) recombinantly producing a polypeptide of the Formula V within inclusion bodies of a bacterial host cell:

$$\text{Tag-IBFP-Linker-GLP-2} \qquad \text{V}$$

wherein:
  Tag is a translation initiation sequence comprising SEQ ID NO:17 or 18;
  IBFP is an inclusion body leader partner comprising any one of SEQ ID NO:19, 20, 21 or 22;

Linker is a cleavable peptide linker having Formula IV:

(Peptide$_5$)$_m$-Xaa$_1$-Xaa$_2$  IV wherein:
n is an integer ranging from 0 to 50;
m is an integer ranging from 0 to 50;
Xaa$_1$ is aspartic acid, glycine, proline, or glutamic acid;
Xaa$_2$ is arginine; and
Peptide$_s$ is a single amino acid residue or a multiple amino acid sequence; and
GLP-2 has any of the sequences given for the GLP-2 peptides;
(b) isolating the bacterial inclusion bodies;
(c) solubilizing the inclusion bodies containing the polypeptide of Formula V using urea;
(d) cleaving, in the presence of about 0 M to about 8 M urea, at least one peptide bond within the polypeptide of Formula V using clostripain, wherein clostripain cleaves a peptide bond on the C-terminal side of Xaa$_2$.

The invention also includes methods of transpeptidation and C-terminus amidation. In particular, the invention also provides a method of producing a GLP-2 peptide amide or extension. The method involves the steps of:
(a) recombinantly producing a polypeptide of the Formula VIII:

Tag-Linker-[GLP-2-Linker$_2$]$_q$  VIII wherein:
Tag is an amino acid sequence comprising SEQ ID NO:17 or 18;
Linker is a cleavable peptide linker having Formula IV:

(Peptide$_5$)$_m$-Xaa$_1$-Xaa$_2$  IV wherein:
n is an integer ranging from 0 to 50;
m is an integer ranging from 0 to 50;
Xaa$_1$ is aspartic acid, glycine, proline, or glutamic acid;
Xaa$_2$ is arginine; and
Peptide$_5$ is any amino acid combination;
Linker$_2$ is SEQ ID NO:23;
GLP-2 is any of the GLP-2 peptide sequences described herein;
q is an integer of about 2 to about 20;
(b) isolating the polypeptide of Formula VIII;
cleaving at least one peptide bond within the polypeptide of Formula VIII using clostripain in the presence of ammonia, wherein clostripain cleaves a peptide bond on the C-terminal side of Xaa$_2$, amidates the carbonyl of Xaa$_2$ and thereby forms a GLP-2(1-34)NH$_2$ peptide having SEQ ID NO: 10, or a GLP-2(1-33)NH$_2$ peptide having SEQ ID NO:12. Alternatively, glycine instead of ammonia can be included within the clostripain cleavage to produce a GLP-2(1-33) peptide.

Finally, additional aspects of the invention include modifications regarding production of polypeptide within a bacterial cell. A DNA segment encoding the precursor polypeptide can be transformed into the bacterial host cells. The DNA segment can also encode a peptidyl sequence linked to the precursor polypeptide wherein the peptidyl sequence encourages the polypeptide to be sequestered within bacterial inclusion bodies. Such peptidyl sequences are termed "inclusion body leader partners" and include peptidyl sequences having, for example, SEQ ID NO:19, 20, 21 or 22. Use of such an inclusion body leader partner facilitates isolation and purification of the polypeptide. Isolation of the bacterial inclusion bodies containing the polypeptide is simple (e.g., centrifugation). According to the invention, the isolated inclusion bodies can be used without substantial purification, for example, by solubilizing the polypeptide in urea and then conducting the clostripain cleavage reaction either before or after removal of the urea. Clostripain is capable of cleaving polypeptide in comparatively high concentrations of urea, for example, in the presence of about 0 M to about 8 M urea, so removal of urea is not required. Hence, the invention provides methods for cleaving a soluble polypeptide, or an insoluble polypeptide that can be made soluble by adding urea.

The invention also includes an assay for measuring the development of inclusion bodies. The method involves use of a phenolic medium and separation/analytic techniques. Details are given within the Examples section.

DESCRIPTION OF THE DRAWINGS

FIG. 9A: (dashed line is 10% ethanol) (dotted line is 20% ethanol) (solid line is 35% ethanol). Peak 1 is GLP-2(21-33), Peak 2 is GLP-2(1-33,A2G) (SEQ ID NO:40) and Peak 3 is the T7tagVg-VDDR-GLP-2(1-33,A2G) (SEQ ID NO:40) precursor polypeptide. FIG. 9B: (closed square) rate of formation of GLP-2(1-33,A2G) in 30% ethanol; (closed triangle) rate of formation of GLP-2(1-33,A2G) in 30% acetonitrile; (closed circle) rate of formation of GLP-2(1-33,A2G) in the absence of organic solvent; (open circle) rate of formation of GLP-2(21-33) in the absence of an organic solvent; (open triangle) rate of formation of GLP-2(21-33) in 30% acetonitrile; (open square) rate of formation of GLP-2(21-33) in 30% ethanol.

DEFINITIONS OF THE INVENTION

Figure 1:
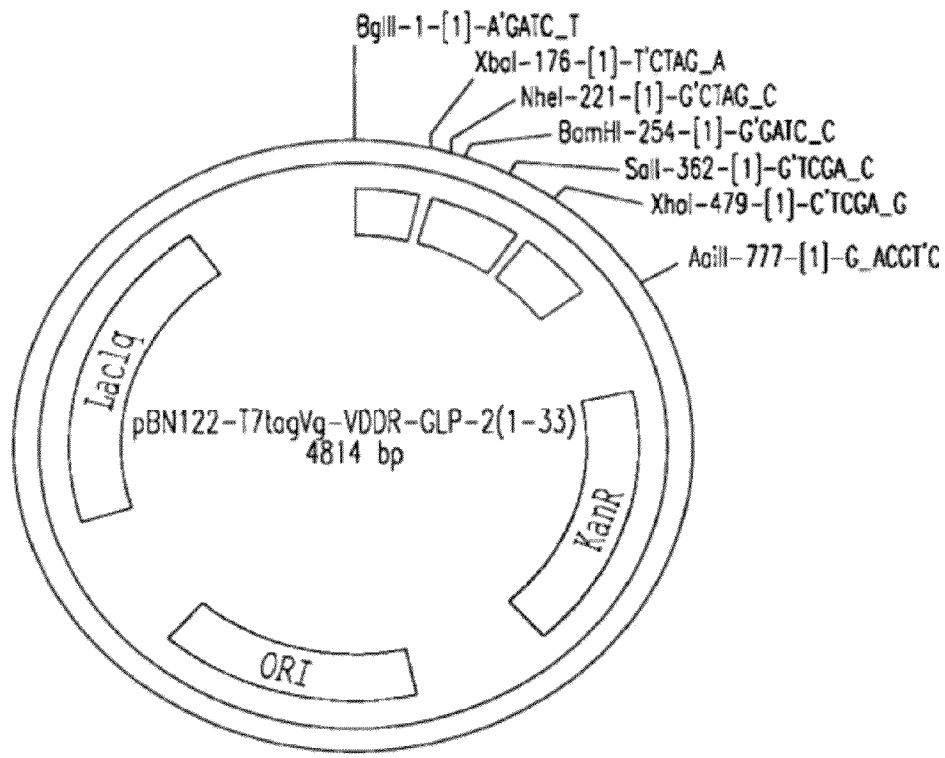
FIG. 1 provides schematic diagrams of A: a pBN121 vector containing a DNA segment encoding the precursor polypeptide, T7tag-GSDR(GLP-2(1-34))$_6$ (SEQ ID NO:37). B: a pBN122 vector containing a DNA segment encoding the precursor polypeptide. T7tagVg-VDDR-GLP-2(1-33,A2G) PYX (SEQ ID NO:38); chlorella Virus Promoter.

Abbreviations: LC-MS: liquid chromatography-mass spectroscopy; TFA: trifloroacetic acid; DTT: dithiothreitol; DTE: dithioerythritol.

An "Amino acid analog" includes amino acids that are in the D rather than L form, as well as other well-known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, N-methyl-alanine, para-benzoyl-phenylalanine, phenylglycine, propargylglycine, sarcosine, N-acetylserine, N-formylmethionine, 3-methyl-histidine, 5-hydroxylysine, norleucine, norvaline, orthonitrophenylglycine and other similar amino acids.

The terms, "cells," "cell cultures", "Recombinant host cells", "host cells", and other such terms denote, for example, microorganisms, insect cells, and mammalian cells, that can be, or have been, used as recipients for nucleic acid constructs or expression cassettes, and include the progeny of the original cell which has been transformed. It is understood that the progeny of a single parental cell may not necessarily be completely identical in morphology or in genomic or total DNA complement as the original parent, due to natural, accidental, or deliberate mutation. Many cells are available from ATCC and commercial sources. Many mammalian cell lines are known in the art and include, but are not limited to, Chinese hamster ovary (CHO) cells, HeLa cells, baby hamster kidney (BHK) cells, monkey kidney cells (COS), and human hepatocellular carcinoma cells (e.g., Hep G2). Many prokaryotic cells are known in the art and include, but are not limited to, *Escherichia coli* and *Salmonella typhimurium*. Sambrook and Russell, Molecular Cloning: A Laboratory Manual, 3rd edition (Jan. 15, 2001) Cold Spring Harbor Laboratory Press, ISBN: 0879695765. Many insect cells are known in the art and include, but are not limited to, silkworm cells and mosquito cells. (Franke and Hruby, *J. Gen. Virol.*, 66:2761 (1985); Marumoto et al., *J. Gen. Virol.*, 68:2599 (1987)).

A "cleavable peptide linker" refers to a peptide sequence having a clostripain cleavage recognition sequence.

A "coding sequence" is a nucleic acid sequence that is translated into a polypeptide, such as a preselected polypeptide, usually via mRNA. The boundaries of the coding sequence are determined by a translation start codon at the 5'-terminus and a translation stop codon at the 3'-terminus of an mRNA. A coding sequence can include, but is not limited to, cDNA, and recombinant nucleic acid sequences.

A "conservative amino acid" refers to an amino acid that is functionally similar to a second amino acid. Such amino acids may be substituted for each other in a polypeptide with minimal disturbance to the structure or function of the polypeptide. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Neutral: Asparagine (N), Glutamine (Q). Examples of other synthetic and non-genetically encoded amino acid types are provided herein.

The term "gene" is used broadly to refer to any segment of nucleic acid that encodes a preselected polypeptide. Thus, a gene may include a coding sequence for a preselected polypeptide and/or the regulatory sequences required for expression. A gene can be obtained from a variety of sources. For example, a gene can be cloned or PCR amplified from a source of interest, or it can be synthesized from known or predicted sequence information.

An "inclusion body" is an amorphous polypeptide deposit in the cytoplasm of a cell. In general, inclusion bodies comprise aggregated protein that is improperly folded or inappropriately processed.

An "inclusion body leader partner" is a peptide that causes a polypeptide to which it is attached to form an inclusion body when expressed within a bacterial cell. The inclusion body leader partners of the invention can be altered to confer isolation enhancement onto an inclusion body that contains the altered inclusion body leader partner.

The term "lysate" as used herein refers to the product resulting from the breakage of cells. Such cells include both prokaryotic and eukaryotic cells. For example, bacteria may be lysed though a large number of art recognized methods. Such methods include, but are not limited to, treatment of cells with lysozyme, French press, treatment with urea, organic acids, and freeze thaw methods. Methods for lysing cells are known and have been described. (Sambrook and Russell, Molecular Cloning: A Laboratory Manual, 3rd edition (Jan. 15, 2001) Cold Spring Harbor Laboratory Press, ISBN: 0879695765; Stratagene, La Jolla, Calif.).

An "open reading frame" (ORF) is a region of a nucleic acid sequence that encodes a polypeptide.

"Operably-linked" refers to the association of nucleic acid sequences or amino acid sequences on a single nucleic acid fragment or a single amino acid sequence so that the function of one is affected by the other. For example, a regulatory DNA sequence is said to be "operably linked to" or "associated with" a DNA sequence that codes for an RNA if the two sequences are situated such that the regulatory DNA sequence affects expression of the coding DNA sequence (i.e., that the coding sequence or functional RNA is under the transcriptional control of the promoter). In an example related to amino acid sequences, an inclusion body leader partner is said to be operably linked to a preselected amino acid sequence when the inclusion body leader partner causes a precursor polypeptide to form an inclusion body. In another example, a signal sequence is said to be operably linked to a preselected amino acid when the signal sequence directs the precursor polypeptide to a specific location in a cell.

The term "polypeptide" refers to a polymer of amino acids and does not limit the size to a specific length of the product. However, as used herein, a polypeptide is generally longer than a peptide and may include one or more copies of a peptide of interest (the terms peptide of interest and desired peptide are used synonymously herein). This term also optionally includes post expression modifications of the polypeptide, for example, glycosylations, acetylations, phosphorylations and the like. Included within the definition are, for example, polypeptides containing one or more analogues of an amino acid or labeled amino acids.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence. Promoters may be derived in their entirety from a native gene, or be composed of different elements derived from different promoters found in nature, or even be comprised of synthetic DNA segments. A promoter may also contain DNA segments that are involved in the binding of protein factors that control the effectiveness of transcription initiation in response to physiological or environmental conditions.

The term "purification stability" refers to the isolation characteristics of an inclusion body formed from a polypeptide having an inclusion body leader partner operably linked to a polypeptide. High purification stability indicates that an inclusion body can be isolated from a cell in which it was produced. Low purification stability indicates that the inclusion body is unstable during purification due to dissociation of the polypeptides forming the inclusion body.

When referring to a polypeptide or nucleic acid, "isolated" means that the polypeptide or nucleic acid has been removed from its natural source. An isolated polypeptide or nucleic acid may be present within a non-native host cell and so the polypeptide or nucleic acid is therefore not necessarily "purified."

The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

"Regulated promoter" refers to a promoter that directs gene expression in a controlled manner rather than in a constitutive manner. Regulated promoters include inducible promoters and repressable promoters. Such promoters may include natural and synthetic sequences as well as sequences that may be a combination of synthetic and natural sequences. Different promoters may direct the expression of a gene in response to different environmental conditions. Typical regulated promoters useful in the invention include, but are not limited to, promoters used to regulate metabolism (e.g., an IPTG-inducible lac promoter) heat-shock promoters (e.g., an SOS promoter), and bacteriophage promoters (e.g., a T7 promoter).

A "ribosome-binding site" is a DNA sequence that encodes a site on an mRNA at which the small and large subunits of a ribosome associate to form an intact ribosome and initiate translation of the mRNA. Ribosome binding site consensus sequences include AGGA or GAGG and are usually located some 8 to 13 nucleotides upstream (5') of the initiator AUG codon on the mRNA. Many ribosome-binding sites are known in the art. (Shine et al., *Nature*, 254:34, (1975); Steitz et al., "Genetic signals and nucleotide sequences in messenger RNA", in: Biological Regulation and Development: Gene Expression (ed. R. F. Goldberger) (1979)).

A "selectable marker" is generally encoded on the nucleic acid being introduced into the recipient cell. However, cotransfection of selectable marker can also be used during introduction of nucleic acid into a host cell. Selectable markers that can be expressed in the recipient host cell may include, but are not limited to, genes which render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. (Davies et al., *Ann. Rev. Microbiol.*, 32:469, (1978)). Selectable markers may also include biosynthetic genes, such as those in the histidine, tryptophan, and leucine biosynthetic pathways. Upon transfection or transformation of a host cell, the cell is placed into contact with an appropriate selection marker.

The term "self-adhesion" refers to the association between polypeptides that have an inclusion body leader partner to form an inclusion body. Self-adhesion may affect the purification stability of an inclusion body formed from the polypeptide. Self-adhesion that is too great produces inclusion bodies having polypeptides that are so tightly associated with each other that it is difficult to separate individual polypeptides from an isolated inclusion body. Self-adhesion that is too low produces inclusion bodies that are unstable during isolation due to dissociation of the polypeptides that form the inclusion body. Self-adhesion can be regulated by altering the amino acid sequence of an inclusion body leader partner.

A "signal sequence" is a region in a protein or polypeptide responsible for directing an operably linked polypeptide to a cellular location or compartment designated by the signal sequence. For example, signal sequences direct operably linked polypeptides to the inner membrane, periplasmic space, and outer membrane in bacteria. The nucleic acid and amino acid sequences of such signal sequences are well-known in the art and have been reported. Watson, Molecular Biology of the Gene, 4th edition, Benjamin/Cummings Publishing Company, Inc., Menlo Park, Calif. (1987); Masui et al., in: Experimental Manipulation of Gene Expression, (1983); Ghrayeb et al., *EMBO J.*, 3:2437 (1984); Oka et al., *Proc. Natl. Acad. Sci. USA*, 82:7212 (1985); Palva et al., *Proc. Natl. Acad. Sci. USA*, 79:5582 (1982); U.S. Pat. No. 4,336, 336).

Signal sequences, preferably for use in insect cells, can be derived from genes for secreted insect or baculovirus proteins, such as the baculovirus polyhedrin gene (Carbonell et al., *Gene*, 73:409 (1988)). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, signal sequences of non-insect origin, such as those derived from genes encoding human α-interferon (Maeda et al., *Nature*, 315:592 (1985)), human gastrin-releasing peptide (Lebacq-Verheyden et al., *Mol. Cell. Biol.*, 8:3129 (1988)), human IL-2 (Smith et al., *Proc. Natl. Acad. Sci. USA*, 82:8404 (1985)), mouse IL-3 (Miyajima et al., *Gene*, 58:273 (1987)) and human glucocerebrosidase (Martin et al., *DNA*, 7:99 (1988)), can also be used to provide for secretion in insects.

The term "solubility" refers to the amount of a substance that can be dissolved in a unit volume of solvent. For example, solubility as used herein refers to the ability of a polypeptide to be resuspended in a volume of solvent, such as a biological buffer.

A "Tag" sequence refers to an amino acid sequence that is operably linked to the N-terminus of a peptide or protein. Such tag sequences may provide for the increased expression of a desired peptide or protein. Such tag sequences may also form a cleavable peptide linker when they are operably linked to another peptide or protein. Examples of tag sequences include, but are not limited to, the sequences indicated in SEQ ID NOs: 17 and 18.

A "transcription terminator sequence" is a signal within DNA that functions to stop RNA synthesis at a specific point along the DNA template. A transcription terminator may be either rho factor dependent or independent. An example of a transcription terminator sequence is the T7 terminator. Transcription terminators are known in the art and may be isolated from commercially available vectors according to recombinant methods known in the art. (Sambrook and Russell, Molecular Cloning: A Laboratory Manual, 3rd edition (Jan. 15, 2001) Cold Spring Harbor Laboratory Press, ISBN: 0879695765; Stratagene, La Jolla, Calif.).

"Transformation" refers to the insertion of an exogenous nucleic acid sequence into a host cell, irrespective of the method used for the insertion. For example, direct uptake, transduction, f-mating or electroporation may be used to introduce a nucleic acid sequence into a host cell. The exogenous nucleic acid sequence may be maintained as a non-integrated vector, for example, a plasmid, or alternatively, may be integrated into the host genome.

A "translation initiation sequence" refers to a DNA sequence that codes for a sequence in a transcribed mRNA that is optimized for high levels of translation initiation. Numerous translation initiation sequences are known in the art. These sequences are sometimes referred to as leader sequences. A translation initiation sequence may include an optimized ribosome-binding site. In the present invention, bacterial translational start sequences are preferred. Such translation initiation sequences are available in the art and may be obtained from gene 10 of bacteriophage T7, and the gene encoding ompT. Those of skill in the art can readily obtain and clone translation initiation sequences from a variety of commercially available plasmids, such as the pET series of plasmids. (Stratagene, La Jolla, Calif.).

A "unit" of clostripain activity is defined as the amount of enzyme required to transform 1 µmole of benzoyl-L-arginine ethyl ester (BAEE) to benzoyl-L-arginine per minute at 25° C. under defined reaction conditions. The transformation is measured spectroscopically at 253 nm. The assay solution contained 2.5 mM BAEE, 10 mM HEPES (pH 6.7), 2 mM $CaCl_2$, and 1 mM DTT.

A "variant" polypeptide is intended a polypeptide derived from the reference polypeptide by deletion, substitution or addition of one or more amino acids to the N-terminal and/or C-terminal end of the native polypeptide; deletion or addition of one or more amino acids at one or more sites in the native protein; or substitution of one or more amino acids at one or more sites in the reference protein. Such substitutions or insertions are preferably conservative amino acid substitutions. Methods for such manipulations are generally known in the art. Kunkel, *Proc. Natl. Acad. Sci. USA*, 82:488, (1985); Kunkel et al., *Methods in Enzymol.*, 154:367 (1987); U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.).

DETAILED DESCRIPTION OF THE INVENTION

The invention provides methods for efficiently making peptides of the formulas GLP-2(1-33), GLP-2(1-33, A2G), GLP-2(1-34), GLP-2(1-34,A2G) and mutations, permutations and conservative substitutions thereof (hereinafter these peptides are termed the GLP-2 peptides as a group). The peptides are made using recombinant and proteolytic procedures. The invention enables the wide-ranging use of a single cleavage enzyme whose selectivity can be manipulated. In particular, the enzyme, clostripain, can be manipulated to cleave a particular site when the same primary cleavage site appears elsewhere in the peptide. Although limited to initial cleavage at a C-terminal side of arginine residues, the method provides versatility. The versatility arises from the surprising ability to manipulate clostripain so that it will cleave at the C-terminus even though arginine or lysine appears elsewhere within the peptide sequence.

The need to avoid reassimilation of an expressed, desired peptide by host expression cells dictates that the desired peptide should have a significantly high molecular weight and varied amino acid sequence. Such peptide features are desirable when recombinant peptides are being produced. This need means that the expressed polypeptide be formed either as a multicopy of the desired peptide or as a combination of the desired peptide be linked to a discardable peptide sequence. Use of the former multicopy scheme provides multiple copies of the desired peptide under certain circumstances and the desired peptide with several additional amino acid residues at its N- and C-termini under all other circumstances. Use of the latter single copy scheme provides at least a single copy of the desired peptide.

According to the invention, the latter scheme may be employed to produce virtually any desired peptide. The discardable sequence is manipulated according to the invention in part to have arginine as its carboxyl end. The arginine is in turn coupled by its peptide bond to the N-terminus of the desired peptide. The cleavage of that designated arginine according to the invention is so selective that the desired peptide may contain virtually any sequence of amino acids. The cleavage produces a single copy of the desired peptide.

Although it is not to be regarded as a limitation of the invention, the selectivity of this enzymatic cleavage is believed to be the result of the influence of secondary binding sites of the substrate with the enzyme, clostripain. These secondary sites are adjacent to the primary cleavage site and are known as the P and P' sites. There may be one or multiple P and P' sites. The P sites align with the amino acid residues on the amino side of the scissile bond while the P' sites align with the amino acid residues on the carboxyl side of the scissile bond. Thus, the scissile bond resides between the P and the P' bond. The corresponding sites of the enzyme are termed S and S' sites. It is believed that the side chain character of the P and P' amino acid residues immediately adjacent the primary cleavage residue have significant influence upon the ability of the enzyme to bind with and cleave the peptide bond at the primary cleavage site.

For clostripain, it has been discovered that an acidic amino acid residue occupying the $P_2$ site (amino side) immediately adjacent to the $P_1$ primary cleavage amino acid residue, arginine, causes highly selective, rapid attack of clostripain upon that particular primary cleavage site. It has also been discovered that an acidic amino acid residue occupying the $P_1'$ site (carboxyl side) immediately adjacent the primary cleavage site causes repulsion of, and extremely slow attack of, clostripain upon the primary cleavage site.

Thus, according to a preferred method of the invention, a polypeptide that has at least one copy of a peptide of interest may be recombinantly produced. The production may be of a soluble polypeptide or an inclusion body preparation containing at least a substantially insoluble mass of polypeptide. Next, the polypeptide is proteolytically cleaved using clostripain to produce the peptide of interest. By manipulating the polypeptide and/or the cleavage conditions, peptides having any C-terminal residue can be produced. Further, by using the method of this invention, peptides having any C-terminal residue amide can be produced. For example GLP-2(1-33) NH$_2$ or GLP-2(1-34)NH$_2$ can be produced from GLP-2(1-33) CH or GLP-2(1-34)CH respectively through use of the method of this invention.

The Clostripain Cleavage Process According to the Invention

According to the invention, clostripain is used in a selective manner to affect preferential cleavage at a selected arginine site. As explained below, clostripain is recognized to cleave at the carboxyl side of arginine and lysine residues in peptides. One of the surprising features of the present invention is the discovery of the ability to provide a selective cleavage site for clostripain so that it will preferentially cleave at a designated arginine even though other arginine or lysine residues are present within the peptide. Multicopy polypeptides having arginine residues at the inchoate C-termini of the desired peptide product copies within the polypeptide and also having arginine or lysine residues within the desired peptide sequence can be efficiently and selectively cleaved according to the invention to produce the desired peptide product.

Moreover, the enzymatic cleavage, precursor polypeptide and desired peptide product can be manipulated so that the C-terminus of the peptide product may be any amino acid residue. This feature is surprising in view of the cleavage preference of clostripain toward arginine. This feature is accomplished through use of a discardable sequence ending in arginine and joined to the N-terminus of the desired peptide. The cleavage of that designated arginine according to the invention is so selective that the desired peptide may contain virtually any sequence of amino acids. The cleavage produces a single copy of the desired peptide.

Traditional Clostripain Cleavage Conditions

Clostripain (EC 3.4.22.8) is an extracellular protease from *Clostridia* that can be recovered from the culture filtrate of *Clostridium histolyticum*. Clostripain has both proteolytic and amidase/esterase activity. Mitchell et al., *Biol. Chem.*, 243:4683 (1968). Clostripain is a heterodimer with a molecular weight of about 50,000 and an isoelectric point of pH 4.8 to 4.9. Clostripain proteolytic activity is inhibited, for example, by tosyl-L-lysine chloromethyl ketone, hydrogen peroxide, $Co^{++}$, $Cu^{++}$ or $Ca^{++}$ ions, citrate, or $Ca^{++}$ chelators, such as EGTA and EDTA. Examples of clostripain activators include cysteine, mercaptoethanol, dithiothreitol and calcium ions.

Clostripain is generally understood to have specificity for cleavage of Arg-Xaa linkages, though some cleavage can occur at lysine residues under certain reaction conditions. Thus, in the isolated B chain of insulin, clostripain cleaves the Arg-Gly linkage 500 times more rapidly than the Lys-Ala linkage. In glucagon, only the Arg-Arg, the Arg-Ala and the Lys-Tyr sites are cleaved. The relative initial rates of hydrolysis of these three bonds are 1, 1/7 and 1/300. (Labouesses, *Bull. Soc. Chim. Biol.*, 42:1293, (1960)).

Clostripain Cleavage According to the Invention

According to the invention, amino acids flanking arginine can strongly influence clostripain cleavage. In particular, clostripain has a strong preference for a polypeptide having a cleavage site shown by Formula I, where the cleavage occurs at a peptide bond after amino acid Xaa$_2$:

$$\text{Xaa}_1\text{-Xaa}_2\text{-Xaa}_3 \qquad (I)$$

wherein

Xaa$_1$ aspartic acid, glycine, proline or glutamic acid;
Xaa$_2$ is arginine; and
Xaa$_3$ is not an acidic amino acid.

According to the method of the invention, a polypeptide that has at least one copy of a desired peptide is recombinantly produced. The production may be of a soluble polypeptide or may be an inclusion body preparation containing at least a substantially insoluble mass of polypeptide. Next, the polypeptide is proteolytically cleaved using clostripain to produce the desired peptide. The proteolytic reaction can be performed on the solubilzed cellular contents in situations where the polypeptide is soluble. Or, it may be performed on crude preparations of inclusion bodies. In either situation, separation steps prior to or following the enzymatic cleavage may be employed. Use of varying concentrations of urea in the medium containing the crude cellular contents or inclusion bodies in optional combination with such separation steps may also be employed. A reaction vessel can also be used that permits continuous recovery and separation of the peptide away from the uncleaved polypeptide and the clostripain. Use of such a method produces large amounts of pure peptide in essentially one step, eliminating numerous processing steps typically used in currently available procedures.

Clostripain can be used to cleave purified or impure preparations of the polypeptide. The precursor polypeptide can be in solution or it can be an insoluble mass. For example, the precursor polypeptide can be in a preparation of inclusion bodies that becomes soluble in the reaction mixture. According to the invention, clostripain is active in high levels of reagents that are commonly used to solubilize proteins. For example, clostripain is active in high levels of urea. Therefore, concentrations of urea ranging up to about 8M can readily be used in the clostripain cleavage reaction.

Little purification of the polypeptide is required when an inclusion body preparation of the polypeptide is used as a substrate for clostripain cleavage. Essentially, host cells having a recombinant nucleic acid encoding the polypeptide are grown under conditions that permit expression of the polypeptide. Cells are grown to high cell densities, then collected, washed and broken open, for example, by sonication. Inclusion bodies are then collected, washed in water and employed without further purification.

Up to about 8M urea can be used to solubilized insoluble precursor polypeptides, for example, inclusion body preparations of precursor polypeptides. The amount of urea employed can vary depending on the precursor polypeptide. For example, about 0 M to about 8 M urea can be employed in the clostripain reaction mixture to solubilize the precursor polypeptide. Preferred concentrations of urea are about 4 M urea to about 8 M urea.

Urea can also be used in the clostripain reaction. Concentrations of up to 8 M urea can be used in the clostripain cleavage. Preferred concentrations of urea are about 0.0 to about 4 M urea. More preferred concentrations of urea are about 0.0 to about 1.0 M urea. Even more preferred concentrations of urea are about 0.0 to about 0.5 M urea.

In some cases, it may be preferable to remove the urea before cleavage with clostripain. In such cases, urea may be removed by dialysis, gel filtration, tangential flow filtration (TFF), numerous other chromatographic methods, and the like.

Moreover, according to the invention, the cleavage reaction conditions can be modified so that clostripain will have an even stronger preference for cleavage at sites having formula I. Several factors can be modified or implemented to obtain the desired product. Thus, by adjusting the pH and adding organic solvents, such as ethanol or acetonitrile, or by using a selected amount of enzyme relative to precursor polypeptide and/or by using selected reaction times and/or by continuously removing the peptide as it is formed, cleavage at undesired sites can be avoided.

Appropriate inorganic or organic buffers can be used to control the pH of the cleavage reaction. Such buffers include phosphate, Tris, glycine, HEPES and the like. The pH of the reaction can vary between pH 4 and pH 12. However, a pH range between pH 6 and pH 10 is preferred. For amidation, a pH range between 8.5 and 10.5 is preferred. While for hydrolysis, a pH range between 6 and 7 is preferred. When the cleavage is performed on precursor polypeptides in the absence or presence of significant amounts of urea, pH values ranging from about 6.0 to about 6.9 are preferred.

The activity of the clostripain enzyme has surprisingly been found to be influenced by the presence of organic solvents. For example, ethanol and acetonitrile may be used to increase the rate of substrate cleavage as well as the overall yield of product formed from the cleavage of a precursor polypeptide. Another surprising result is that organic solvents influence the cleavage specificity of clostripain. Thus, the presence of an organic solvent can dramatically influence the preferential hydrolysis of one cleavage site in a precursor polypeptide relative to another cleavage site within the same precursor polypeptide. This characteristic of clostripain can be exploited to design precursor polypeptides that are rapidly and preferentially cleaved at specific sites within the precursor polypeptide.

The clostripain enzyme can be activated at similar pH ranges. A suitable buffer substance, for example phosphate, Tris, HEPES, glycine and the like, can be added to maintain the pH.

The concentration of the precursor polypeptide employed during the cleavage is, for example, between 0.01 mg/ml and 100 mg/ml, preferably between 0.1 mg/ml and 20 mg/ml. The ratio of polypeptide to clostripain is, in mg to units about 1:0.01 to about 1:1,000, preferably about 1:0.1 to about 1:50. The temperature of the reaction can also be varied over a wide range and may depend upon the selected reaction conditions. Such a range can be between 0° C. and +80° C. A preferred temperature range is generally between +5° C. and +60° C. Amidation is preferably conducted at a temperature between 5° C. and 60° C., and is more preferably conducted at a temperature between 35° C. and 60° C., and is most preferably conducted at 45° C. Hydrolysis is preferably conducted at a temperature between 20° C. and 30° C., and more preferably is conducted at 25° C.

The time required for the conversion of the precursor polypeptides into the peptides of interest can vary and one of skill in the art can readily ascertain an appropriate reaction time. For example, the reaction time can vary between about 1 minute and 48 hours can be utilized. However, a reaction time of between 0.5 h and 6 h is preferred. A reaction time of 0.5 h and 2 hours is more preferred. In some embodiments, the reaction mixture is preferably placed in a reaction vessel that permits continuous removal of the peptide product. For example, the reaction vessel can have a filter that permits the peptide product of interest to pass through but that retains the precursor polypeptide and the clostripain. An example of an appropriate filtration system is tangential flow filtration (TFF). Reaction buffer, substrate and other components of the reaction mixture can be added batchwise or continuously as the peptide is removed and the reaction volume is lost.

The enzyme can be activated before use in a suitable manner in the presence of a mercaptan. Mercaptans suitable for activation are compounds containing SH groups. Examples of such activating compounds include DTT, DTE, mercaptoethanol, thioglycolic acid or cysteine. Cysteine is preferably used. The concentration of the mercaptan can also vary. In general, concentrations between about 0.01 mM and 50 mM are useful. Preferred mercaptan concentrations include concentrations between about 0.05 mM and 5 mM. More preferred mercaptan concentrations are between about 0.5 mM and 2 mM. The activation temperature can be between 0° C. and 80° C. Preferably the activation temperature can be between 0° C. and 40° C., more preferably the activation temperature is between 0° C. and 30° C. Most preferably the activation temperature is between 15° C. and 25° C.

Clostripain can be purchased from commercially available sources or prepared from microorganisms. Natural and recombinant clostripain is available. For example, natural clostripain can be prepared from *Clostridia* bacteria by cultivating the bacteria until clostripain accumulates in the nutrient medium. *Clostridia* used for producing clostripain include, for example, *Clostridium histolyticum*, especially *Clostridium histolyticum* DSM 627. Culturing is carried out anaerobically, singly or in mixed culture, for example, in non-agitated culture in the absence of oxygen or in fermenters. Where appropriate nitrogen, inert gases or other gases apart from oxygen can be introduced into the culture. The fermentation is carried out in a temperature range from about 10° to 45° C., preferably about 25° to 40° C., especially 30° to 38° C. Fermentation takes place in a pH range between 5 and 8.5, preferably between 5.5 and 8. Under these conditions, the culture broth generally shows a detectable accumulation of the enzyme after 1 to 3 days. The synthesis of clostripain starts in the late log phase and reaches its maximum in the stationary phase of growth. The production of the enzyme can be followed by means of activity assays (Mitchell, *Meth. of Enzymol.*, 47:165 (1977)).

The nutrient solution used for producing clostripain can contain 0.2 to 6%, preferably 0.5 to 3%, of organic nitrogen compounds, and inorganic salts. Suitable organic nitrogen compounds are: amino acids, peptones, also meat extracts, milled seeds, for example of corn, wheat, beans, soybean or the cotton plant, distillation residues from alcohol production, meat meals or yeast extracts. Examples of inorganic salts that the nutrient solution can contain are chlorides, carbonates, sulfates or phosphates of the alkali metals or alkaline earth metals, iron, zinc and manganese, but also ammonium salts and nitrates.

Clostripain can be purified by classical processes, for example by ammonium sulfate precipitation, ion exchange or gel permeation chromatography. Clostripain can also be produced recombinantly and thereafter purified according to standard methods.

Peptides of Interest Serving as Substrates According to the Invention

Almost any peptide can be formed by the methods of the invention. Peptides with an arginine at their C-terminus can readily be cleaved from a polypeptide containing end-to-end copies of the peptide. Peptides with one or more internal arginine residues can also be made by employing the teachings of the invention on which arginine-containing sites are favored for cleavage. Peptides having C-terminal amino acids other than arginine can be produced by placing a clostripain cleavage site within the polypeptide at the N-terminus of the peptide of interest. This latter technique produces the single copy desired peptide and employs a recombinantly expressed polypeptide having a discardable peptide sequence at the N-terminal side of the desired peptide.

Clostripain is generally perceived to be an "arginine" or an "arginine/lysine" protease, meaning that clostripain cleaves polypeptides on the carboxyl side of arginine and/or lysine amino acid residues. However, according to the invention, clostripain has even greater specificity, particularly under the reaction conditions provides herein. Hence, peptides with internal lysine and arginine residues can be made by the procedures of the invention.

Moreover, the construction of the polypeptide can be manipulated so that the peptide of interest is present at the C-terminus of the polypeptide and a clostripain cleavage site is at the N-terminus of the peptide of interest. Hence, when cleavage is performed on a polypeptide containing such a C-terminal peptide, the peptide is readily released. Using such a precursor polypeptide, peptides with any C-terminal residue can be formed.

According to the invention, peptides having one or more internal arginine residues can still be selectively cleaved at their termini so that a functional, full-length peptide can be recovered. This enhanced selectivity is achieved by recognition that clostripain preferentially cleaves a polypeptide having a sequence as shown in Formula I, where the cleavage occurs at a peptide bond after amino acid $Xaa_2$:

$$Xaa_1\text{-}Xaa_2\text{-}Xaa_3 \tag{I}$$

wherein
$Xaa_1$ aspartic acid, glycine, proline or glutamic acid;
$Xaa_2$ is arginine; and
$Xaa_3$ is not an acidic amino acid.

Hence, a peptide of the Formula $Xaa_3$-Peptide$_1$-$Xaa_1$-$Xaa_2$, can readily be excised from a polypeptide having end-to-end concatemers of the peptide, when $Xaa_1$, $Xaa_2$, and $Xaa_3$ are as described above. Peptide$_1$ refers to a peptidyl entity that is unique to the selected peptide of interest. Hence, Peptide$_1$ has any amino acid sequence that is selected by one of skill in the art. An example of such a polypeptide with end-to-end concatemers of the peptide of interest has Formula II:

$$(Xaa_3\text{-Peptide}_1\text{-}Xaa_1\text{-}Xaa_2)_n\text{-}Xaa_3\text{-Peptide}_1\text{-}Xaa_1\text{-}Xaa_2 \tag{II}$$

wherein
the peptide produced comprises $Xaa_3$-Peptide$_1$-$Xaa_1$-$Xaa_2$;
the desired GLP-2 peptides have the formula $Xaa_3$-Peptide$_1$;
n is an integer ranging from 0 to 50;
$Xaa_1$ is aspartic acid, glycine, proline or glutamic acid;
$Xaa_2$ is arginine; and
$Xaa_3$ is not an acidic amino acid.

However, the invention is not limited to cleavage of polypeptides having end-to-end concatemers of a peptide of interest. The invention also provides methods of making large amounts of a peptide that is present as a single copy within a polypeptide. This aspect of the invention enables the production of a single copy desired peptide having virtually any amino acid sequence and one not having an arginine at the C-terminus, such as the desired GLP-2 peptides of the invention. That is, the invention provides methods of making large amounts of peptides of the Formula, $Xaa_3$-Peptide$_1$, which do not have a C-terminal lysine or arginine. A cleavable peptide linker can be attached onto the peptide (e.g., Linker-$Xaa_3$-Peptide$_1$) to generate an N-terminal cleavage site for generating peptides of interest that have no C-terminal arginine or lysine. The Linker has a C-terminal $Xaa_1$-$Xaa_2$ sequence that directs cleavage to the junction between the C-terminal $Xaa_2$ residue of the Linker and the $Xaa_3$ N-terminal residue of the peptide. Hence, peptides of the Formula, $Xaa_3$-Peptide$_1$, that have C-terminal acidic, aliphatic or aromatic amino acids can readily be made by the present methods.

Cleavage of a peptide of the Formula, $Xaa_3$-Peptide$_1$, from a polypeptide having at least one copy of the peptide relies upon the presence of a site that has Formula I ($Xaa_1$-$Xaa_2$-$Xaa_3$) at the junction between the peptide and the attached Linker or polypeptide. The $Xaa_3$ amino acid forms the N-terminal end of the peptide and is not an acidic amino acid sequence. Polypeptides of Formula III can readily be cleaved by clostripain:

$$(\text{Linker-}Xaa_1\text{-}Xaa_2\text{-}Xaa_3\text{-Peptide}_1)_n\text{-Linker-}Xaa_1\text{-}Xaa_2\text{-}Xaa_3\text{-Peptide}_1 \qquad \text{Formula III}$$

wherein
the peptide comprises $Xaa_3$-$Peptide_1$
n is an integer ranging from 0 to 50;
$Xaa_1$ is aspartic acid, glycine, proline or glutamic acid;
$Xaa_2$ is arginine; and
$Xaa_3$ is not an acidic amino acid.

Cleavage of a polypeptide of Formula III yields one molar equivalent of the $Xaa_3$-$Peptide_1$ and n molar equivalents of a polypeptide of the following structure: $Xaa_3$-$Peptide_1$-Linker-$Xaa_1$-$Xaa_2$. While this polypeptide may not have a specific utility after cleavage, many "unused" parts of the linker or the polypeptide do have specific purposes. For example, the $Xaa_1$-$Xaa_2$ amino acids in the polypeptide are recognized by and direct clostripain to cleave the $Xaa_2$-$Xaa_3$ peptide bond with specificity. As described in the section entitled "Precursor polypeptides," other parts of the polypeptide or the linker have specific functions relating to the recombinant expression, translation, sub-cellular localization, etc. of the polypeptide within the host cell.

Almost any peptide of interest to one of skill in the art can be made by the methods of the invention. In particular, preferred peptides of interest (desired peptides) include, for example, a GLP-2 glucagon-like peptide. Different kinds of GLP-2 peptides can be made by the methods of the invention include, for example, GLP-2(1-33) (SEQ ID NO:11), GLP-2(1-33) amide (SEQ ID NO:12), GLP-2(1-33, A2G) (SEQ ID NO:13), GLP-2(1-33,A2G) amide (SEQ ID NO:14), GLP-2(1-34) (SEQ ID NO:9), GLP-2(1-34)$NH_2$ (SEQ ID NO:10), GLP-2(1-34) A2G (SEQ ID NO:15), GLP-2 (1-34)A2G-$NH_2$ (SEQ ID NO:16), and the like. The sequences of such GLPs are provided in Table 1 along with their names and SEQ ID NO: ("NO:").

TABLE 1

| Name | Sequence | SEQ ID NO: |
|---|---|---|
| GLP-2(1-34) | HADGSFSDEMNTILDNLAARD FINWLIQTKITDR | 9 |
| GLP-2(1-34)$NH_2$ | HADGSFSDEMNTILDNLAARD FINWLIQTKITDR-$NH_2$ | 10 |
| GLP-2(1-33) | HADGSFSDEMNTILDNLAARD FINWLIQTKITD | 11 |
| GLP-2(1-33)-$NH_2$ | HADGSFSDEMNTILDNLAARD FINWLIQTKITD-$NH_2$ | 12 |
| GLP-2(1-33, A2G) | HGDGSFSDEMNTILDNLAARD FINWLIQTKITD | 13 |
| GLP-2(1-33, A2G)-$NH_2$ | HGDGSFSDEMNTILDNLAARD FINWLIQTKITD-$NH_2$ | 14 |
| GLP-2(1-34)A2G | HGDGSFSDEMNTILDNLAARD FINWLIQTKITDR | 15 |
| GLP-2(1-34)A2G-$NH_2$ | HGDGSFSDEMNTILDNLAARD FINWLIQTKITDR-$NH_2$ | 16 |

The invention also contemplates peptide variants, mutations, and derivatives of the GLP-2 peptides described herein. Derivatives, mutations and variant peptides of the invention are derived from the reference peptide by deletion, substitution or addition of one or more amino acids to the N-terminal and/or C-terminal end; deletion, substitution or addition of one or more amino acids at one or more sites within the peptide; or substitution of one or more amino acids at one or more sites of peptide. Thus, the GLP-2 peptides of the invention may be altered in various ways including amino acid substitutions, deletions, truncations, and insertions. The invention also includes the GLP-2 peptides, analogs, variants, modifications, additions, substitutions, deletions and the like disclosed in U.S. Pat. Nos. 5,990,077 and 6,184,201

Such variant and derivative polypeptides may result, for example, from human manipulation. Methods for such manipulations are generally known in the art. For example, amino acid sequence variants of the polypeptides can be prepared by mutations in the DNA. Methods for mutagenesis and nucleotide sequence alterations are well-known in the art. See, for example, Kunkel, *Proc. Natl. Acad. Sci. USA*, 82:488 (1985); Kunkel et al., *Methods in Enzymol.*, 154:367 (1987); U.S. Pat. No. 4,873,192; Walker and Gaastra, eds., Techniques in Molecular Biology, MacMillan Publishing Company, New York (1983) and the references cited therein. Guidance as to appropriate amino acid substitutions that do not affect biological activity of the protein of interest may be found in the model of Dayhoff et al., Atlas of Protein Sequence and Structure, Natl. Biomed. Res. Found., Washington, C.D. (1978), herein incorporated by reference.

Precursor Polypeptides

Any precursor polypeptide containing one or more copies of a peptide of interest (desired peptide) and a Formula I sequence at one or both ends of that peptide can be utilized as a substrate for the clostripain cleavage methods of the invention. One of skill in the art can readily design many such precursor polypeptides. While the peptide of interest may form a substantial portion of the precursor polypeptide, the polypeptide may also have additional peptide segments unrelated to the peptide sequence of interest. Additional peptide segments can provide any function desired by one of skill in the art.

One example of an additional peptide segment that can be present in the precursor polypeptide is a "Tag" that provides greater levels of precursor polypeptide production in cells. Numerous tag sequences are known in the art. In the present invention, bacterial tag sequences are preferred. Such tag sequences may be obtained from gene 10 bacteriophage T7, and the gene encoding ompT. In one embodiment, a T7 tag is used that has the amino acid sequence ASMTGGQQMGR (SEQ ID NO:17). In another embodiment, a T7 tag is used that has the amino acid sequence MASMTGGQQMGR (SEQ ID NO:18).

The precursor polypeptide can also encode an "inclusion body leader partner" that is operably linked to the peptide of interest. Such an inclusion body leader partner may be linked to the amino-terminus, the carboxyl-terminus or both termini of a precursor polypeptide. In one example, the inclusion body leader partner has an amino acid sequence corresponding to: GSGQGQAQYLSASCVVFTNYSGDTASQVD (SEQ ID NO:19). In another embodiment, the inclusion body leader partner is a part of the *Drosophila* vestigial polypeptide ("Vg"), having sequence GSGQGQAQYLAASLVVF TNYSGDTASQ VDVNGPRAMVD (SEQ ID NO:20). In another embodiment, the inclusion body leader partner is a part of polyhedrin polypeptide ("Ph"), having sequence GSAEEEEILLEVSLVFKVKEFAPDAPLFTGPAYVD (SEQ ID NO:21). Other inclusion body leader partners that can be used include a part of the lactamase polypeptide, having sequence SIQHFRVALIPFFAAFSLPVFA (SEQ ID NO:22). Upon expression of the polypeptide, an attached inclusion body leader partner causes the polypeptide to form inclusion bodies within the bacterial host cell. Other inclusion body leader partners can be identified, for example, by linking a test inclusion body leader partner to a polypeptide construct.

The resulting inclusion body leader partner-polypeptide construct then would be tested to determine whether it will form an inclusion body within a cell.

The amino acid sequence of an inclusion body leader partner can be altered to produce inclusion bodies that facilitate isolation of inclusion bodies that are formed, thereby allowing an attached polypeptide to be purified more easily. For example, the inclusion body leader partner may be altered to produce inclusion bodies that are more or less soluble under a certain set of conditions. Those of skill in the art realize that solubility is dependent on a number of variables that include, but are not limited to, pH, temperature, salt concentration, protein concentration and the hydrophilicity or hydrophobicity of the amino acids in the protein. Thus, an inclusion body leader partner of the invention may be altered to produce an inclusion body having desired solubility under differing conditions.

An inclusion body leader partner may also be altered to produce inclusion bodies that contain polypeptide constructs having greater or lesser self-association. Self-association refers to the strength of the interaction between two or more polypeptides that form an inclusion body. Such self-association may be determined though use of a variety of known methods used to measure protein-protein interactions. Such methods are known in the art and have been described. Freifelder, Physical Biochemistry: Applications to Biochemistry and Molecular Biology, W.H. Freeman and Co., 2nd edition, New York, N.Y. (1982).

Self-adhesion can be used to produce inclusion bodies that exhibit varying stability to purification. For example, greater self-adhesion may be desirable to stabilize inclusion bodies against dissociation in instances where harsh conditions are used to isolate the inclusion bodies from a cell. Such conditions may be encountered if inclusion bodies are being isolated from cells having thick cell walls. However, where mild conditions are used to isolate the inclusion bodies, less self-adhesion may be desirable as it may allow the polypeptide constructs composing the inclusion body to be more readily solubilized or processed. Accordingly, an inclusion body leader partner of the invention may be altered to provide a desired level of self-adhesion for a given set of conditions.

The precursor polypeptide can also encode one or more "cleavable peptide linkers" that can flank one or more copies of the peptide of interest. Such a cleavable peptide linker provides a convenient clostripain cleavage site adjacent to a peptide of interest, and allows a peptide that does not naturally begin or end with an arginine or lysine to be excised with clostripain. Convenient cleavable peptide linkers include short peptidyl sequences having a C-terminal $Xaa_1$-$Xaa_2$ sequence, for example, a Linker-$Xaa_1$-$Xaa_2$ sequence, wherein $Xaa_1$ is aspartic acid, glycine, proline or glutamic acid, and $Xaa_2$ is arginine. The $Xaa_1$-$Xaa_2$ sequence directs cleavage to the junction between the C-terminal $Xaa_2$ residue of the linker and a $Xaa_3$ residue on the N-terminus of the peptide.

A cleavable peptide linker can have the following Formula IV:

$$(Peptide_5)_m\text{-}Xaa_1\text{-}Xaa_2 \quad\quad\quad IV$$

wherein:
   n and m are separately an integer ranging from 0 to 50;
   $Xaa_1$ is aspartic acid, glycine, proline or glutamic acid; and
   $Xaa_2$ is arginine; and
   $Peptide_5$ is any single or multiple amino acid residue.
In some embodiments, use of $Peptide_5$ as proline is preferred.

Many cleavable peptide linker sequences can readily be developed and used by one of skill in the art. A few examples of convenient cleavable peptide linker sequences are provided below.

```
Ala-Phe-Leu-Gly-Pro-Gly-Asp-Arg    (SEQ ID NO: 23)

Val-Asp-Asp-Arg                    (SEQ ID NO: 24)

Gly-Ser-Asp-Arg                    (SEQ ID NO: 25)

Ile-Thr-Asp-Arg                    (SEQ ID NO: 26)

Pro-Gly-Asp-Arg.                   (SEQ ID NO: 27)
```

Other amino acids, peptides, or polypeptides selected by one of skill in the art can also be included in the precursor polypeptide.

GLP-2 Polypeptides

In one embodiment of the invention, the polypeptide can encode one or more copies of GLP-2.

Examples of multi-copy GLP-2 polypeptides include polypeptides having the following generalized structures:

$$\text{Tag-Linker-[GLP-2(1-34)]}_q \quad\quad\quad VI$$

Where GLP-2 (1-34) has SEQ ID NO:9 and q is an integer of about 2 to about 20. A preferred value for q is about 6. The Linker is preferably $Peptide_5$-Asp-Arg or $Xaa_4$-$Xaa_5$-Asp-Arg-Arg. Tag is a translation initiation sequence, for example, SEQ ID NO: 18. A multi-copy GLP-2 polypeptide of this generalized structure with q equal to 6 and with Linker as $Peptide_5$-Asp-Arg (GSDR) has the following sequence:

```
                                              (SEQ ID NO: 29)
MASMTGGQQMGR-GSDR-

HADGSFSDEMNTILDNLAARDFINWLIQTKITDR-

HADGSFSDEMNTILDNLAARDFINWLIQTKITDR-

HADGSFSDEMNTILDNLAARDFINWLIQTKITDR-

HADGSFSDEMNTILDNLAARDFINWLIQTKITDR-

HADGSFSDEMNTILDNLAARDFINWLIQTKITDR-

HADGSFSDEMNTILDNLAARDFINWLIQTKITDR.
```

No cleavable peptide linkers are needed between the GLP-2 six peptides present within this precursor polypeptide because GLP-2(1-34) has an Asp-Arg sequence at its C-terminus.

In another embodiment of the invention, the polypeptide can encode a copy of GLP-2.

Examples of such a GLP-2 polypeptide include polypeptides having the following generalized structures:

$$\text{Tag-Linker-[GLP-2(1-33)]} \quad\quad\quad VI$$

Where GLP-2(1-33) has SEQ ID NO: 11. The Linker is preferably $Peptide_5$-Asp-Arg or $Peptide_5$-Asp-Arg-Arg. Tag is a translation initiation sequence, for example, SEQ ID NO: 17 or 18. A multi-copy GLP-2 polypeptide of this generalized structure with Linker as $Peptide_5$-Asp-Arg (GSDR) has the following sequence:

```
                                              (SEQ ID NO:28)
MASMTGGQQMGR-GSDR-

HADGSFSDEMNTILDNLAARDFINWLIQTKITD.
```

One of skill in the art can modify or mutate these GLP-2 polypeptide sequences as desired so long as the aspartic acid at position 21 of GLP-2 (HADGSFSDEMNTILDN LAARDFINWLIQTKITDR, SEQ ID NO:9) or GLP-2 (HADGSFSDEMNTILDN LAARDFINWLIQTKITD, SEQ ID NO:11) is not changed. This aspartic acid is on the C-terminal side of an arginine and is therefore at position $Xaa_3$ in the clostripain cleavage site. As described, $Xaa_3$ should not be an acidic amino acid when clostripain cleavage is desired. However, in the GLP-2 polypeptides described above, an acidic amino acid at position 21 (Asp-21) protects against cleavage at the internal arginine. Recognition that Asp-21 protects against cleavage allows a full-length GLP-2 peptide to be produced in far larger amounts than a GLP-2 fragment containing only amino acids 1-19.

One mutation that can be made is a substitution of glycine for alanine at position 2 of the GLP-2 peptide, to produce GLP-2(1-34)A2G having SEQ ID NO:15, or GLP-2(1-33, A2G) having SEQ ID NO:13. This amino acid substitution of glycine for alanine produces a GLP-2 peptide that lacks a recognition site for a eukaryotic endopeptidase that might degrade the peptide upon administration to a mammal. Hence, a GLP-2(1-33,A2G) or GLP-2(1-34,A2G) peptide can have a longer half-life in vivo than the GLP-2(1-33) or GLP-2(1-34) peptide.

Amidation Conditions

When clipped from a multicopy polypeptide under normal hydrolysis conditions, recombinant GLP-2 has a C-terminal carboxyl group. However, an amidated C-terminus is preferred for use in mammals. Clostripain can be used to amidate the C-terminal residue to make an amidated recombinant GLP-2 by adjusting the conditions to increase the amount of amide formation. However, the recombinant GLP-2 amide itself becomes a substrate for hydrolysis as it is formed. To solve this problem, a tangential flow filtration in combination with the enzyme reaction is used. Clostripain simultaneously cleaves multicopy peptide constructs and amidates the C-terminal residue of the single copy cleaved peptide. Use of tangential flow filtration during the enzymatic reaction to remove the amidated peptide produces that peptide in high yield.

For example, use of a 10K diafiltration/tangential flow filtration membrane will enhance the reaction yield. Undigested peptide construct and clostripain are retained on the retentate side of the membrane. The single copy cleaved GLP-2 passes through the membrane. Continued exposure of GLP-2 amide to clostripain will result in loss of the amide to OH. Continual removal of amide through the membrane will reduce this unwanted side reaction. Smaller pore sized membranes were not as efficient at removing the newly formed GLP-2 amide during the reaction time course.

Clostripain, like other proteases, will perform transpeptidation reactions in the presence of a nucleophile other than water. Ammonia or other amines can be used as the nucleophile. A polypeptide that had three copies of the GLP-2 peptide was used as a substrate. The polypeptide had a leader sequence as well.

Reaction conditions will enhance the transpeptidation reaction relative to hydrolysis for this particular polypeptide construct. Urea in the clostripain reaction maintains peptide solubility and minimizes membrane fouling. The clostripain digestion/amidation reaction will tolerate higher urea concentrations. The amount of clostripain can be varied to shorten or lengthen the overall reaction time. Fresh buffer can be added to maintain constant volume or after volume reduction. However, care must be maintained to ensure the minimum volume of liquid remains in place to prevent foaming.

Production of Precursor Polypeptides

A) DNA Constructs and Expression Cassettes

Precursor polypeptides are produced in any convenient manner, for example, by using a recombinant nucleic acid that encodes the desired precursor polypeptide. Nucleic acids encoding the precursor polypeptides of the invention can be inserted into convenient vectors for transformation of an appropriate host cell. Those of skill in the art can readily obtain and clone nucleic acids encoding a selected precursor polypeptide into a variety of commercially available plasmids. One example of a useful plasmid vector is the pET series of plasmids (Stratagene, La Jolla, Calif.). After insertion of the selected nucleic acid into an appropriate vector, the vector can be introduced into a host cell, preferably a bacterial host cell.

Nucleic acid constructs and expression cassettes can be created through use of recombinant methods that are available in the art. (Sambrook and Russell, Molecular Cloning: A Laboratory Manual, 3rd edition (Jan. 15, 2001) Cold Spring Harbor Laboratory Press, ISBN: 0879695765; Ausubel et al., *Current Protocols in Molecular Biology*, Green Publishing Associates and Wiley Interscience, NY (1989)). Generally, recombinant methods involve preparation of a desired DNA fragment and ligation of that DNA fragment into a preselected position in another DNA vector, such as a plasmid.

In a typical example, a desired DNA fragment is first obtained by synthesizing and/or digesting a DNA that contains the desired DNA fragment with one or more restriction enzymes that cut on both sides of the desired DNA fragment. The restriction enzymes may leave a "blunt" end or a "sticky" end. A "blunt" end means that the end of a DNA fragment does not contain a region of single-stranded DNA. A DNA fragment having a "sticky" end means that the end of the DNA fragment has a region of single-stranded DNA. The sticky end may have a 5' or a 3' overhang. Numerous restriction enzymes are commercially available and conditions for their use are also well-known. (USB, Cleveland, Ohio; New England Biolabs, Beverly, Mass.).

The digested DNA fragments may be extracted according to known methods, such as phenol/chloroform extraction, to produce DNA fragments free from restriction enzymes. The restriction enzymes may also be inactivated with heat or other suitable means. Alternatively, a desired DNA fragment may be isolated away from additional nucleic acid sequences and restriction enzymes through use of electrophoresis, such as agarose gel or polyacrylamide gel electrophoresis. Generally, agarose gel electrophoresis is used to isolate large nucleic acid fragments while polyacrylamide gel electrophoresis is used to isolate small nucleic acid fragments. Such methods are used routinely to isolate DNA fragments. The electrophoresed DNA fragment can then be extracted from the gel following electrophoresis through use of many known methods, such as electoelution, column chromatography, or binding of glass beads. Many kits containing materials and methods for extraction and isolation of DNA fragments are commercially available. (Qiagen, Venlo, Netherlands; Qbiogene, Carlsbad, Calif.).

The DNA segment into which the fragment is going to be inserted is then digested with one or more restriction enzymes. Preferably, the DNA segment is digested with the same restriction enzymes used to produce the desired DNA fragment. This will allow for directional insertion of the DNA fragment into the DNA segment based on the orientation of the complimentary ends. For example, if a DNA fragment is produced that has an EcoRI site on its 5' end and a BamHI site at the 3' end, it may be directionally inserted into a DNA segment that has been digested with EcoRI and BamHI based on the complementarity of the ends of the respective DNAs. Alternatively, blunt ended cloning may be used if no convenient restriction sites exist that allow for directional cloning. For example, the restriction enzyme BsaAI leaves DNA ends that do not have a 5' or 3' overhang. Blunt ended cloning may be used to insert a DNA fragment into a DNA segment that was also digested with an enzyme that produces a blunt end. Additionally, DNA fragments and segments may be digested with a restriction enzyme that produces an overhang and then treated with an appropriate enzyme to produce a blunt end. Such enzymes include polymerases and exonucleases. Those of skill in the art know how to use such methods alone or in combination to selectively produce DNA fragments and segments that may be selectively combined.

A DNA fragment and a DNA segment can be combined though conducting a ligation reaction. Ligation links two pieces of DNA through formation of a phosphodiester bond between the two pieces of DNA. Generally, ligation of two or more pieces of DNA occurs through the action of the enzyme ligase when the pieces of DNA are incubated with ligase under appropriate conditions. Ligase and methods and conditions for its use are well-known in the art and are commercially available.

The ligation reaction or a portion thereof is then used to transform cells to amplify the recombinant DNA formed, such as a plasmid having an insert. Methods for introducing DNA into cells are well-known and are disclosed herein.

Those of skill in the art recognize that many techniques for producing recombinant nucleic acids can be used to produce an expression cassette or nucleic acid construct of the invention.

B) Promoters

The expression cassette of the invention includes a promoter. Any promoter able to direct transcription of the expression cassette may be used. Accordingly, many promoters may be included within the expression cassette of the invention. Some useful promoters include, constitutive promoters, inducible promoters, regulated promoters, cell specific promoters, viral promoters, and synthetic promoters. A promoter is a nucleotide sequence which controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Examples of Promoters Useful in Bacteria

For expression of a precursor polypeptide in a bacterium, an expression cassette having a bacterial promoter will be used. A bacterial promoter is any DNA sequence capable of binding bacterial RNA polymerase and initiating the downstream (3") transcription of a coding sequence into mRNA. A promoter will have a transcription initiation region which is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in E. coli (Raibaud et al., Ann. Rev. Genet., 18:173 (1984)). Regulated expression may therefore be positive or negative, thereby either enhancing or reducing transcription. A preferred promoter is the YX chlorella virus promoter. (U.S. Pat. No. 6,316,224).

Sequences encoding metabolic pathway enzymes provide particularly useful promoter sequences. Examples include promoter sequences derived from sugar metabolizing enzymes, such as galactose, lactose (lac) (Chang et al., Nature, 198:1056 (1977), and maltose. Additional examples include promoter sequences derived from biosynthetic enzymes such as tryptophan (tip) (Goeddel et al., Nuc. Acids Res., 8:4057 (1980); Yelverton et al., Nuc. Acids Res., 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$, (Shimatake et al., Nature, 292:128 (1981)) and T5 (U.S. Pat. No. 4,689,406) promoter systems also provide useful promoter sequences.

Synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., Gene, 25:167 (1983); de Boer et al., Proc. Natl. Acad. Sci. USA, 80:21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., J. Mol. Biol., 189:113 (1986); Tabor et al., Proc. Natl. Acad. Sci. USA, 82:1074 (1985)). In addition, a hybrid promoter can also be comprised of a bacteriophage promoter and an E. coli operator region (EPO Publ. No. 267 851).

Examples of Promoters Useful in Insect Cells

An expression cassette having a baculovirus promoter can be used for expression of a precursor polypeptide in an insect cell. A baculovirus promoter is any DNA sequence capable of binding a baculovirus RNA polymerase and initiating transcription of a coding sequence into mRNA. A promoter will have a transcription initiation region which is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein (Friesen et al., "The Regulation of Baculovirus Gene Expression", in: The Molecular Biology of Baculoviruses (ed. Walter Doerfler), 1986; and EPO Publ. Nos. 127 839 and 155 476) and the gene encoding the baculoviral p10 protein (Vlak et al., *J. Gen. Virol.*, 69:765 (1988)).

Examples of Promoters Useful in Yeast

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PHO5 gene, encoding acid phosphatase, also provides useful promoter sequences. (Myanohara et al., *Proc. Natl. Acad. Sci. USA*, 80:1 (1983).

Synthetic promoters which do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters are known in the art. (Cohen et al., *Proc. Natl. Acad. Sci. USA*, 77:1078 (1980); Henikoff et al., *Nature*, 283:835 (1981); Hollenberg et al., *Curr. Topics Microbiol. Immunol.*, 96:119 (1981); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979; Mercerau-Puigalon et al., *Gene*, 11:163 (1980); Panthier et al., *Curr. Genet.*, 2:109 (1980)).

Examples of Promoters Useful in Mammalian Cells

Many mammalian promoters are known in the art that may be used in conjunction with the expression cassette of the invention. Mammalian promoters often have a transcription initiating region, which is usually placed proximal to the 5' end of the coding sequence, and a TATA-box, usually located 25-30 base pairs (bp) upstream of the transcription initiation site. The TATA-box is thought to direct RNA polymerase II to begin RNA synthesis at the correct site. A mammalian promoter may also contain an upstream promoter element, usually located within 100 to 200 bp upstream of the TATA-box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumour virus LTR promoter, adenovirus major late promoter (Ad MLP), and herpes simplex virus promoter. In addition, sequences derived from non-viral genes, such as the murine metallothioneih gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science*, 236:1237 (1987)); Alberts et al., *Molecular Biology of the Cell*, 2nd ed., 1989). Enhancer elements derived from viruses are often times useful, because they usually have a broad host range. Examples include the SV40 early gene enhancer (Dijkema et al., *EMBO J.*, 4:761 (1985)) and the enhancer/promoters derived from the long terminal repeat (LTR) of the Rous Sarcoma Virus (Gorman et al., *Proc. Natl. Acad. Sci. USA*, 79:6777 (1982b)) and from human cytomegalovirus (Boshart et al., *Cell*, 41:521 (1985)). Additionally, some enhancers are regulatable and become active only in the presence of an inducer, such as a hormone or metal ion (Sassone-Corsi and Borelli, *Trends Genet.*, 2:215 (1986); Maniatis et al., *Science*, 236:1237 (1987)).

It is understood that many promoters and associated regulatory elements may be used within the expression cassette of the invention to transcribe an encoded leader protein. The promoters described above are provided merely as examples and are not to be considered as a complete list of promoters that are included within the scope of the invention.

C) Translation Initiation Sequence

The expression cassette of the invention may contain a nucleic acid sequence for increasing the translation efficiency of an mRNA encoding a precursor polypeptide of the invention. Such increased translation serves to increase production of the leader protein. The presence of an efficient ribosome binding site is useful for gene expression in prokaryotes. In bacterial mRNA a conserved stretch of six nucleotides, the Shine-Dalgarno sequence, is usually found upstream of the initiating AUG codon. (Shine et al., *Nature*, 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well-known. (Ausubel et al., *Current Protocols in Molecular Biology*, Green Publishing Associates and Wiley Interscience, NY. (1989); Beaucage and Caruthers, *Tetra. Letts.*, 22:1859 (1981); VanDevanter et al., *Nucleic*

*Acids Res.,* 12:6159 (1984). Alternatively, translational start sequences can be obtained from numerous commercial vendors. (Operon Technologies; Life Technologies Inc, Gaithersburg, Md.). In a preferred embodiment, the T7 leader sequence is used. The T7 leader sequence is derived from the highly expressed 17 Gene 10 cistron. Other examples of translation initiation sequences include, but are not limited to, the maltose-binding protein (Mal E gene) start sequence (Guan et al., *Gene,* 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Current Protocols in Molecular Biology,* Chapter 16, Green Publishing Associates and Wiley Interscience, NY).

Eucaryotic mRNA does not contain a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a precursor polypeptide encoded by the expression cassette of the invention. Such nucleic acid sequences are within the scope of the invention.

D) Vectors

Vectors that may be used include, but are not limited to, those able to be replicated in prokaryotes and eukaryotes. Vectors include, for example, plasmids, phagemids, bacteriophages, viruses, cosmids, and F-factors. The invention includes any vector into which the expression cassette of the invention may be inserted and replicated in vitro or in vivo. Specific vectors may be used for specific cells types. Additionally, shuttle vectors may be used for cloning and replication in more than one cell type. Such shuttle vectors are known in the art. The nucleic acid constructs may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolabs, Beverly, Mass.; Stratagene, La Jolla, Calif.; Promega, Madison, Wis.; ATCC, Rockville, Md.; CLONTECH, Palo Alto, Calif.; Invitrogen, Carlsbad, Calif.; Origene, Rockville, Md.; Sigma, St. Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

Examples of Vectors Useful in Bacteria

A nucleic acid construct for use in a prokaryote host, such as bacteria, will preferably include a replication system allowing it to be maintained in the host for expression or for cloning and amplification. In addition, a nucleic acid construct may be present in the cell in either high or low copy number. Generally, about 5 to about 200, and usually about 10 to about 150 copies of a high copy number nucleic acid construct will be present within a host cell. A host containing a high copy number plasmid will preferably contain at least about 10, and more preferably at least about 20 plasmids. Generally, about 1 to 10, and usually about 1 to 4 copies of a low copy number nucleic acid construct will be present in a host cell. The copy number of a nucleic acid construct may be controlled by selection of different origins of replication according to methods known in the art. Sambrook and Russell, Molecular Cloning: A Laboratory Manual, 3rd edition (Jan. 15, 2001) Cold Spring Harbor Laboratory Press, ISBN: 0879695765.

A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrations are thought to result from recombinations between homologous DNA in the vector and the bacterial chromosome. For example, integrating vectors constructed with DNA from various *Bacillus* strains integrate into the *Bacillus* chromosome (EPO Publ. No. 127 328). Integrating vectors may also contain bacteriophage or transposon sequences.

Extrachromosomal and integrating nucleic acid constructs may contain selectable markers to allow for the selection of bacterial strains that have been transformed. Selectable markers can be expressed in the bacterial host and may include genes that render bacteria resistant to drugs such as ampicillin, chloramphenicol, erythromycin, kanamycin (neomycin), and tetracycline (Davies et al., *Ann. Rev. Microbiol.,* 32:469, 1978). Selectable markers may also include biosynthetic genes, such as those in the histidine, tryptophan, and leucine biosynthetic pathways.

Numerous vectors, either extra-chromosomal or integrating vectors, have been developed for transformation into many bacteria. For example, vectors have been developed for the following bacteria: *B. subtilis* (Palva et al., *Proc. Natl. Acad. Sci. USA,* 79:5582, 1982; EPO Publ. Nos. 036 259 and 063 953; PCT Publ. No. WO 84/04541), *E. coli* (Shimatake et al., *Nature,* 292:128, 1981; Amann et al., *Gene,* 40:183, 1985; Studier et al., *J. Mol. Biol.,* 189:113, 1986; EPO Publ. Nos. 036 776, 136 829 and 136 907), *Streptococcus cremoris* (Powell et al., *Appl. Environ. Microbiol.,* 54:655, 1988); *Streptococcus lividans* (Powell et al., *Appl. Environ. Microbiol.,* 54:655, 1988), and Streptomyces lividans (U.S. Pat. No. 4,745,056). Numerous vectors are also commercially available (New England Biolabs, Beverly, Mass.; Stratagene, La Jolla, Calif.).

Examples of Vectors Useful in Yeast

Many vectors may be used to construct a nucleic acid construct that contains an expression cassette of the invention and that provides for the expression of a precursor polypeptide in yeast. Such vectors include, but are not limited to, plasmids and yeast artificial chromosomes. Preferably the vector has two replication systems, thus allowing it to be maintained, for example, in yeast for expression and in a prokaryotic host for cloning and amplification. Examples of such yeast-bacteria shuttle vectors include YEp24 (Botstein, et al., *Gene,* 8:17 (1979)), pCl/1 (Brake et al., *Proc. Natl. Acad. Sci. USA,* 81:4642 (1984)), and YRp17 (Stinchcomb et al., *J. Mol. Biol.,* 158:157 (1982)). A vector may be maintained within a host cell in either high or low copy number. For example, a high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the precursor polypeptide on the host. (Brake et al., *Proc. Natl. Acad. Sci. USA,* 81:4642 (1984)).

A nucleic acid construct may also be integrated into the yeast genome with an integrating vector. Integrating vectors usually contain at least one sequence homologous to a yeast chromosome that allows the vector to integrate, and preferably contain two homologous sequences flanking an expression cassette of the invention. Integrations appear to result from recombinations between homologous DNA in the vector and the yeast chromosome. (Orr-Weaver et al., *Methods in Enzymol.*, 101:228 (1983)). An integrating vector may be directed to a specific locus in yeast by selecting the appropriate homologous sequence for inclusion in the vector. One or more nucleic acid constructs may integrate, which may affect the level of recombinant protein produced. (Rine et al., *Proc. Natl. Acad. Sci. USA*, 80:6750 (1983)). The chromosomal sequences included in the vector can occur either as a single segment in the vector, which results in the integration of the entire vector, or two segments homologous to adjacent segments in the chromosome and flanking an expression cassette included in the vector, which can result in the stable integration of only the expression cassette.

Extrachromosomal and integrating nucleic acid constructs may contain selectable markers that allow for selection of yeast strains that have been transformed. Selectable markers may include, but are not limited to, biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a selectable marker may also provide yeast with the ability to grow in the presence of toxic compounds, such as metal. For example, the presence of CUP1 allows yeast to grow in the presence of copper ions. (Butt et al., *Microbiol. Rev.*, 51:351 (1987)).

Many vectors have been developed for transformation into many yeasts. For example, vectors have been developed for the following yeasts: *Candida albicans* (Kurtz et al., *Mol. Cell. Biol.*, 6:142 (1986)), *Candida maltose* (Kunze et al., *J. Basic Microbiol.*, 25:141 (1985)), *Hansenula polymorpha* (Gleeson et al., *J. Gen. Microbiol.*, 132:3459 (1986); Roggenkamp et al., *Mol. Gen. Genet.*, 202:302 (1986), *Kluyveromyces fragilis* (Das et at., *J. Bacteriol.*, 158: 1165 (1984)), *Kluyveromyces lactis* (De Louvencourt et al., *J. Bacteriol.*, 154:737 (1983); van den Berg et al., *Bio/Technology*, 8:135 (1990)), *Pichia guillerimondii* (Kunze et al., *J. Basic Microbiol.*, 25:141 (1985)), *Pichia pastoris* (Cregg et al., *Mol. Cell. Biol.*, 5:3376, 1985; U.S. Pat. Nos. 4,837,148 and 4,929,555), *Saccharomyces cerevisiae* (Hinnen et al., *Proc. Natl. Acad. Sci. USA*, 75:1929 (1978); Ito et al., *J. Bacteriol.*, 153:163 (1983)), *Schizosaccharomyces pombe* (Beach and Nurse, *Nature* 300:706 (1981)), and *Yarrowia lipolytica* (Davidow et al., *Curr. Genet.*, 10:39 (1985); Gaillardin et al., *Curr. Genet.*, 10:49 (1985)).

Examples of Vectors Useful in Insect Cells

Baculovirus vectors have been developed for infection into several insect cells and may be used to produce nucleic acid constructs that contain an expression cassette of the invention. For example, recombinant baculoviruses have been developed for *Aedes aegypti*, *Autographa californica*, *Bombyx mori*, *Drosophila melanogaster*, *Spodoptera frugiperda*, and *Trichoplusia ni* (PCT Pub. No. WO 89/046699; Carbonell et al., *J. Virol.*, 56:153 (1985); Wright, *Nature*, 321: 718 (1986); Smith et al., *Mol. Cell. Biol.*, 3: 2156 (1983); and see generally, Fraser et al., *In Vitro Cell. Dev. Biol.*, 25:225 (1989)). Such a baculovirus vector may be used to introduce an expression cassette into an insect and provide for the expression of a precursor polypeptide within the insect cell.

Methods to form a nucleic acid construct having an expression cassette of the invention inserted into a baculovirus vector are well-known in the art. Briefly, an expression cassette of the invention is inserted into a transfer vector, usually a bacterial plasmid which contains a fragment of the baculovirus genome, through use of common recombinant methods. The plasmid may also contain a polyhedrin polyadenylation signal (Miller et al., *Ann. Rev. Microbiol.*, 42:177 (1988) and a prokaryotic selection marker, such as ampicillin resistance, and an origin of replication for selection and propagation in *Escherichia coli*. A convenient transfer vector for introducing foreign genes into AcNPV is pAc373. Many other vectors, known to those of skill in the art, have been designed. Such a vector is pVL985 (Luckow and Summers, *Virology*, 17:31 (1989)).

A wild-type baculoviral genome and the transfer vector having an expression cassette insert are transfected into an insect host cell where the vector and the wild-type viral genome recombine. Methods for introducing an expression cassette into a desired site in a baculovirus virus are known in the art. (Summers and Smith, Texas Agricultural Experiment Station Bulletin No. 1555, 1987. Smith et al., *Mol. Cell. Biol.*, 3:2156 (1983); and Luckow and Summers, *Virology*, 17:31 (1989)). For example, the insertion can be into a gene such as the polyhedrin gene, by homologous double crossover recombination; insertion can also be into a restriction enzyme site engineered into the desired baculovirus gene (Miller et al., *Bioessays*, 4:91 (1989)). The expression cassette, when cloned in place of the polyhedrin gene in the nucleic acid construct, will be flanked both 5' and 3' by polyhedrin-specific sequences. An advantage of inserting an expression cassette into the polyhedrin gene is that occlusion bodies resulting from expression of the wild-type polyhedrin gene may be eliminated. This may decrease contamination of leader proteins produced through expression and formation of occlusion bodies in insect cells by wild-type proteins that would otherwise form occlusion bodies in an insect cell having a functional copy of the polyhedrin gene.

The packaged recombinant virus is expressed and recombinant plaques are identified and purified. Materials and methods for baculovirus and insect cell expression systems are commercially available in kit form. (Invitrogen, San Diego, Calif., USA ("MaxBac" kit)). These techniques are generally known to those skilled in the art and fully described in Summers and Smith, Texas Agricultural Experiment Station Bulletin No. 1555, 1987.

Plasmid-based expression systems have also been developed the may be used to introduce an expression cassette of the invention into an insect cell and produce a leader protein. (McCarroll and King, *Curr. Opin. Biotechnol.*, 8:590 (1997)). These plasmids offer an alternative to the production of a recombinant virus for the production of leader proteins.

Examples of Vectors Useful in Mammalian Cells

An expression cassette of the invention may be inserted into many mammalian vectors that are known in the art and are commercially available. (CLONTECH, Carlsbad, Calif.; Promega, Madision, Wis.; Invitrogen, Carlsbad, Calif.). Such vectors may contain additional elements such as enhancers and introns having functional splice donor and acceptor sites. Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papillovaviruses, such as SV40 (Gluzman, *Cell*, 23:175 (1981)) or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification.

Examples of such mammalian-bacteria shuttle vectors include pMT2 (Kaufman et al., *Mol. Cell. Biol.,* 9:946 (1989)) and pHEBO (Shimizu et al., *Mol. Cell. Biol.,* 6:1074 (1986)).

E) Host Cells

Host cells producing the recombinant precursor polypeptides for the methods of the invention include prokaryotic and eukaryotic cells of single and multiple cell organisms. Bacteria, fungi, plant, insect, vertebrate and its subclass mammalian cells and organisms may be employed. Single cell cultures from such sources as well as functional tissue and whole organisms can operate as production hosts according to the invention. Examples include *E. coli,* tobacco plant culture, maize, soybean, fly larva, mice, rats, hamsters, as well as CHO cell cultures, immortal cell lines and the like.

In a preferred embodiment, bacteria are used as host cells. Examples of bacteria include, but are not limited to, Gram-negative and Gram-positive organisms. *Escherichia coli* is a preferred organism for expression of preselected polypeptides and amplification of nucleic acid constructs. Many publicly available *E. coli* strains include K-strains such as MM294 (ATCC 31, 466); X1776 (ATCC 31, 537); KS 772 (ATCC 53, 635); JM109; MC1061; HMS 174; and the B-strain BL21. Recombination minus strains may be used for nucleic acid construct amplification to avoid recombination events. Such recombination events may remove concatemers of open reading frames as well as cause inactivation of an expression cassette. Furthermore, bacterial strains that do not express a select protease may also be useful for expression of preselected polypeptides to reduce proteolytic processing of expressed polypeptides. Such strains include, for example, Y1090hsdR, which is deficient in the lon protease.

Eukaryotic cells may also be used to produce a preselected polypeptide and for amplifying a nucleic acid construct. Eukaryotic cells are useful for producing a preselected polypeptide when additional cellular processing is desired. For example, a preselected polypeptide may be expressed in a eukaryotic cell when glycosylation of the polypeptide is desired. Examples of eukaryotic cell lines that may be used include, but are not limited to: AS52, H187, mouse L cells, NIH-3T3, HeLa, Jurkat, CHO-K1, COS-7, BHK-21, A-431, HEK293, L6, CV-1, HepG2, HC11, MDCK, silkworm cells, mosquito cells, and yeast.

F) Transformation

Methods for introducing exogenous DNA into bacteria are available in the art, and usually include either the transformation of bacteria treated with $CaCl_2$ or other agents, such as divalent cations and DMSO. DNA can also be introduced into bacterial cells by electroporation, use of a bacteriophage, or ballistic transformation. Transformation procedures usually vary with the bacterial species to be transformed (see, e.g., Masson et al., *FEMS Microbiol. Lett.,* 60:273, 1989; Palva et al., *Proc. Natl. Acad. Sci. USA,* 79:5582, 1982; EPO Publ. Nos. 034 259 and 063 953; PCT Publ. No. WO 84/04541 [*Bacillus*], Miller et al., *Proc. Natl. Acad. Sci. USA,* 8:856, 1988; Wang et al., *J. Bacteriol.,* 172:949, 1990 [*Campylobacter*], Cohen et al., *Proc. Natl. Acad. Sci. USA,* 69: 2110, 1973; Dower et al., *Nuc. Acids Res.,* 16:6127, 1988; Kushner, "An improved method for transformation of *Escherichia coli* with ColE1-derived plasmids", in: Genetic Engineering: Proceedings of the International Symposium on Genetic Engineering (eds. H. W. Boyer and S. Nicosia), 1978; Mandel et al., *J. Mol. Biol.,* 53:159, 1970; Taketo, *Biochim. Biophys. Acta,* 949:318, 1988 [*Escherichia*], Chassy et al., *FEMS Microbiol. Lett.,* 44:173, 1987 [*Lactobacillus*], Fiedler et al., *Anal. Biochem,* 170:38, 1988 [*Pseudomonas*], Augustin et al., *FEMS Microbiol. Lett.,* 66:203, 1990 [*Staphylococcus*], Barany et al., *J. Bacteriol.,* 144:698, 1980; Harlander, "Transformation of *Streptococcus lactis* by electroporation", in: Streptococcal Genetics (ed. J. Ferretti and R. Curtiss III), 1987; Perry et al., *Infec. Immun.,* 32: 1295, 1981; Powell et al., *Appl. Environ. Microbiol.,* 54: 655, 1988; Somkuti et al., *Proc. 4th Eur. Cong. Biotechnology,* 1:412, 1987 [*Streptococcus*]).

Methods for introducing exogenous DNA into yeast hosts are well-known in the art, and usually include either the transformation of spheroplasts or of intact yeast cells treated with alkali cations. Transformation procedures usually vary with the yeast species to be transformed (see, e.g., Kurtz et al., *Mol. Cell. Biol.,* 6:142 (1986); Kunze et al., *J. Basic Microbiol.,* 25:141 (1985) [*Candida*], Gleeson et al., *J. Gen. Microbiol.,* 132:3459 (1986); Roggenkamp et al., *Mol. Gen. Genet.,* 202:302 (1986) [*Hansenula*], Das et al., *J. Bacteriol.,* 158: 1165 (1984); De Louvencourt et al., *J. Bacteriol.,* 754:737 (1983); Van den Berg et al., *Bio/Technology,* 8:135 (1990) [*Kluyveromyces*], Cregg et al., *Mol. Cell. Biol.,* 5:3376 (1985); Kunze et al., *J. Basic Microbiol.,* 25:141 (1985); U.S. Pat. Nos. 4,837,148 and 4,929,555 [*Pichia*], Hinnen et al., *Proc. Natl. Acad. Sci. USA,* 75:1929 (1978); Ito et al., *J. Bacteriol.,* 153:163 (1983) [*Saccharomyces*], Beach and Nurse, *Nature,* 300:706 (1981) [*Schizosaccharomyces*], and Davidow et al., *Curr. Genet.,* 10:39 (1985); Gaillardin et al., *Curr. Genet.,* 10:49 (1985) [*Yarrowia*]).

Exogenous DNA is conveniently introduced into insect cells through use of recombinant viruses, such as the baculoviruses described herein.

Methods for introduction of heterologous polynucleotides into mammalian cells are known in the art and include lipid-mediated transfection, dextran-mediated transfection, calcium phosphate precipitation, polybrene-mediated transfection, protoplast leader, electroporation, encapsulation of the polynucleotide(s) in liposomes, biollistics, and direct microinjection of the DNA into nuclei. The choice of method depends on the cell being transformed as certain transformation methods are more efficient with one type of cell than another. (Feigner et al., *Proc. Natl. Acad. Sci.,* 84:7413 (1987); Feigner et al., *J. Biol. Chem.,* 269:2550 (1994); Graham and van der Eb, *Virology,* 52:456 (1973); Vaheri and Pagano, *Virology,* 27:434 (1965); Neuman et al., *EMBO J.,* 1:841 (1982); Zimmerman, *Biochem. Biophys. Acta.,* 694: 227 (1982); Sanford et al., *Methods Enzymol.,* 217:483 (1993); Kawai and Nishizawa, *Mol. Cell. Biol.,* 4:1172 (1984); Chaney et al., *Somat. Cell Mol. Genet.,* 12:237 (1986); Aubin et al., *Methods Mol. Biol.,* 62:319 (1997)). In addition, many commercial kits and reagents for transfection of eukaryotic are available.

Following transformation or transfection of a nucleic acid into a cell, the cell may be selected for through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes which render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. (Davies et al., *Ann. Rev. Microbiol.,* 32:469, 1978). Selectable markers may also include biosynthetic genes, such as those in the histidine, tryptophan, and leucine biosynthetic pathways.

Upon transfection or transformation of a host cell, the cell is placed into contact with an appropriate selection marker.

For example, if a bacterium is transformed with a nucleic acid construct that encodes resistance to ampicillin, the transformed bacterium may be placed on an agar plate containing ampicillin. Thereafter, cells into which the nucleic acid construct was not introduced would be prohibited from growing to produce a colony while colonies would be formed by those bacteria that were successfully transformed.

EXAMPLES

The following series of Examples illustrates procedures for cloning, expression and detection of precursor polypeptides that can be used to generate a peptide of interest. Examples 1 through 5 provide the protocol and experimental procedures used for preparing peptides of interest using the clostripain cleavage techniques of the present invention. Example 6 provides the application of these protocols and procedures to specific peptides. The peptides chosen are GLP-2(1-34) and GLP-2(1-33, A2G). Example 7 provides data showing the parameters for affecting selectivity of the clostripain cleavage of GLP-2(1-34). Example 10 provides the application of these protocols and procedures to GLP-2(1-33, A2G). Example 11 provides data showing the parameters for affecting selectivity of the clostripain cleavage to GLP-2(1-33, A2G). This series of examples are intended to illustrate certain aspects of the invention and are not intended to be limiting thereof.

Example 1

Construction of Vectors that Contain DNA Which Encodes a Desired Precursor Polypeptide In order to express a desired precursor polypeptide, an expression vector, pBN121 or pBN122, was constructed through use of PCR, restriction enzyme digestion, DNA ligation, transformation into a bacterial host, and screening procedures according to procedures described, for example, in Sambrook et al., Molecular Cloning ($2^{nd}$ edition). Preferably the vector contains regulatory elements that provide for high level expression of a desired precursor polypeptide. Examples of such regulatory elements include, but are not limited to: an inducible promoter such as the chlorella virus promoter (U.S. Pat. No. 6,316,224); an origin of replication for maintaining the vector in high copy number such as a modified pMB1 promoter; a LaqIq gene for promoter suppression; an aminophosphotransferase gene for kanamycin resistance; and a GST terminator for terminating mRNA synthesis (FIGS. 1 and 1A). The pBN121 vector uses a Tac promoter instead of the chlorella virus promoter.

E. coli is a preferred host. To clone the expression cassette of T7tag-GSDR-[GLP-2(1-34)]$_6$(SEQ ID NO:37), or T7tagVg-VDDR-GLP-2(1-33,A2G) (SEQ ID NO:40), PCR or multiple PCR extension was performed to synthesize DNA encoding the T7tag and the indicated GLP-2 gene using preferred codons for E. coli. DNA providing the T7 gene 10 ribosome binding site and the first twelve amino acids (T7tag) after initiation codon was cloned into plasmid pBN121 or pBN122 at XbaI-SalI sites between the promoter and the terminator. DNA encoding the hydrophobic core of the Vestigial (Vg) gene [Williams et al., *Genes Dev. Dec.,* 5:2481 (1991)] was cloned into the plasmid at BamHI-SalI sites. DNA encoding GLP-2(1-33, A2G) or GLP-2(1-34) was cloned into pBN122 or pBN121 respectively at SalI-XhoI sites. Plasmids were transformed into E. coli using heat shock or electroporation procedures ($2^{nd}$ edition, Sambrook et. al). Cells were streaked onto LB+Kanamycin+agar plates, cultures were grown in LB+Kanamycin media from single colonies. Plasmids from these cultures were prepared, screened by restriction enzyme digestion, and sequenced using DNA sequencers. The cultures with the correct plasmid sequence were saved in glycerol stock at −80° C. or below.

Alternative peptides can be cloned by this method using different combinations of restriction enzymes and restriction sites according to methods known in the art.

Example 2

Expression of the Precursor Polypeptide

A shaking flask was inoculated from a glycerol stock of an E. coli strain containing a pBN121 or pBN122 plasmid encoding the desired polypeptide. A complex media containing 1% tryptone was employed that was supplemented with glucose and kanamycin. The shaking culture was grown in a rotary shaker at 37° C. until the optical density was 1.5±0.5 at 540 nm. The contents of the shaking flask culture were then used to inoculate a 5 L fermentation tank containing a defined minimal media containing magnesium, calcium, phosphate and an assortment of trace metals. Glucose served as the carbon source. Kanamycin was added to maintain selection of the recombinant plasmid. During fermentation, dissolved oxygen was controlled at 40% by cascading agitation and areation with additional oxygen. A solution of ammonium hydroxide was used to control the pH at about pH 6.9.

Figure 2:
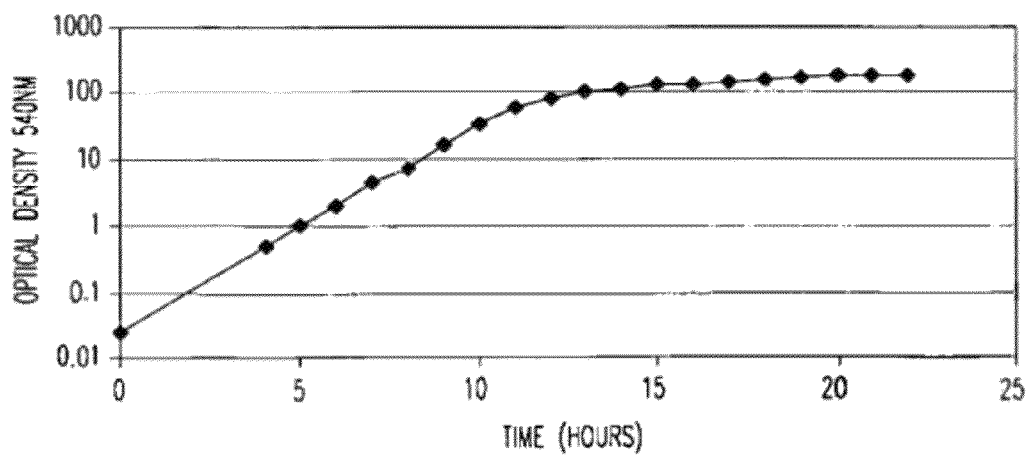
FIG. 2 illustrates a typical growth curve of recombinant *E. coli*. Addition of IPTG generally occurs between 10 and 11 hours. Cells are harvested 6 to 10 hours after induction.

Cell growth was monitored at 540 nm until a target optical density of between about 75 OD, was reached and isopropyl-β D-thiogalactoside (IPTG at between 0.1 and 1.0 mM) was added to induce expression of the desired polypeptide (FIG. 2). When induction was complete, the cells were cooled in the fermenter and harvested with a continuous flow solid bowl centrifuge. The sedimented cells were frozen until used.

The frozen cell pellet was thawed and homogenized in 50 mM Tris, 2.5 mM EDTA, pH 7.8. Inclusion bodies were washed in water and were collected by solid bowl centrifugation. Alternatively, cells were suspended in 8M urea then lysed by conventional means and then centrifuged. The supernatant fluid contained the precursor peptide.

Example 3

Detection of Precursor Polypeptides

To monitor the production of the GLP-2(1-34) precursor polypeptide preparation, cell free extract was diluted 5-fold in 0.2 M HCl in 7.2 M urea. A sample of 15 μl was injected into a Waters Symmetry C-18 column connected to a LCM spectrophotometer. The sample was eluted with a linear gradient from 20% Buffer B (95% acetonitrile, 0.1% TFA) to 75% Buffer B over 15 minutes. The gradient was then charged from 75% B to 100% B over 1 minute. The column was then eluted with 100% Buffer B. Buffer A was 5% acetonitrile with 0.1% TFA.

Figure 3A:
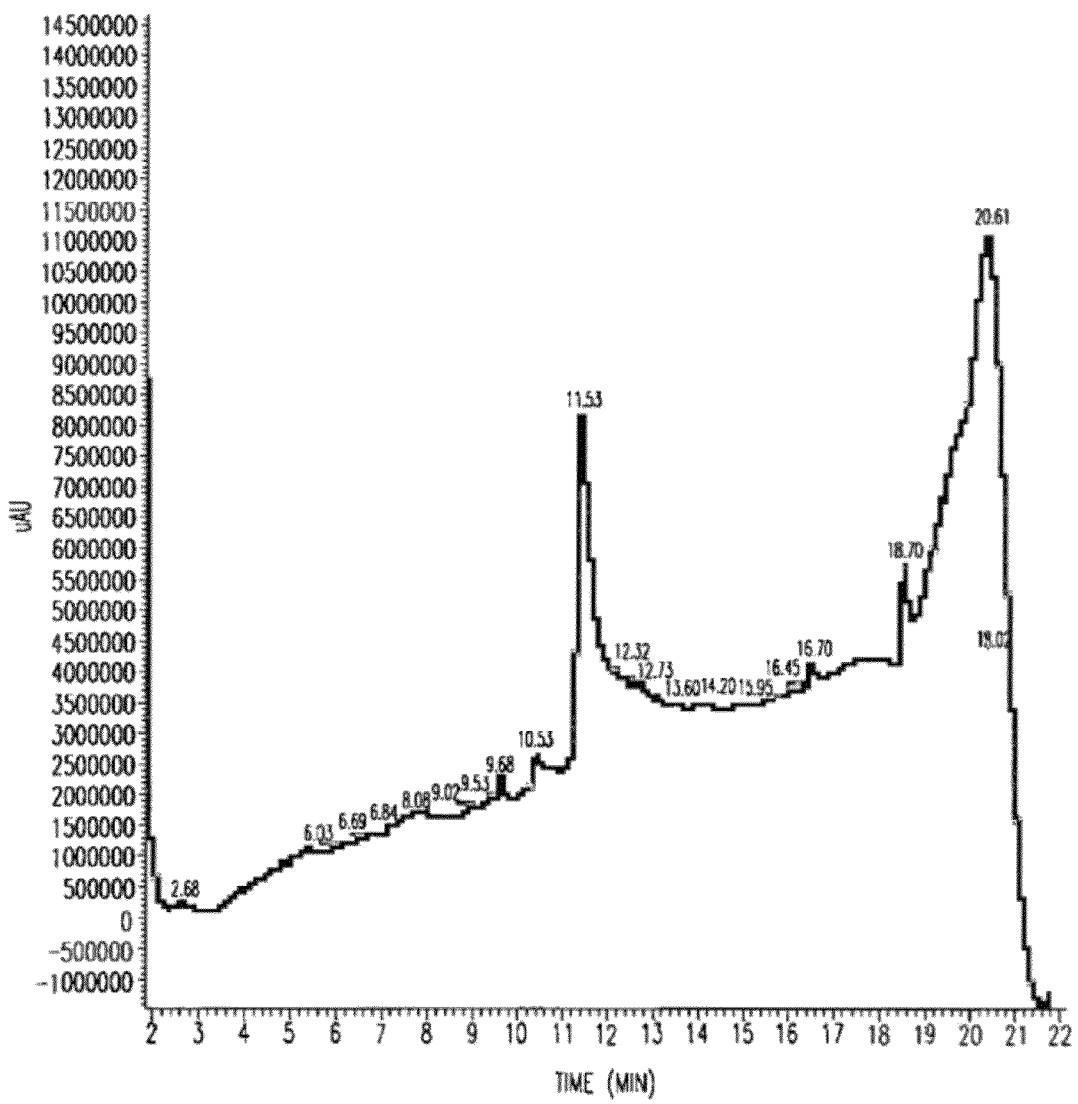
FIGS. 3A and 3B illustrate an LC-MS analysis of cell free extracts from a typical fermentation producing T7tagVg-GSDR-[GLP-2(1-34)]$_6$ (SEQ ID NO:37) (about 9 gm/L)
Figure 3B:
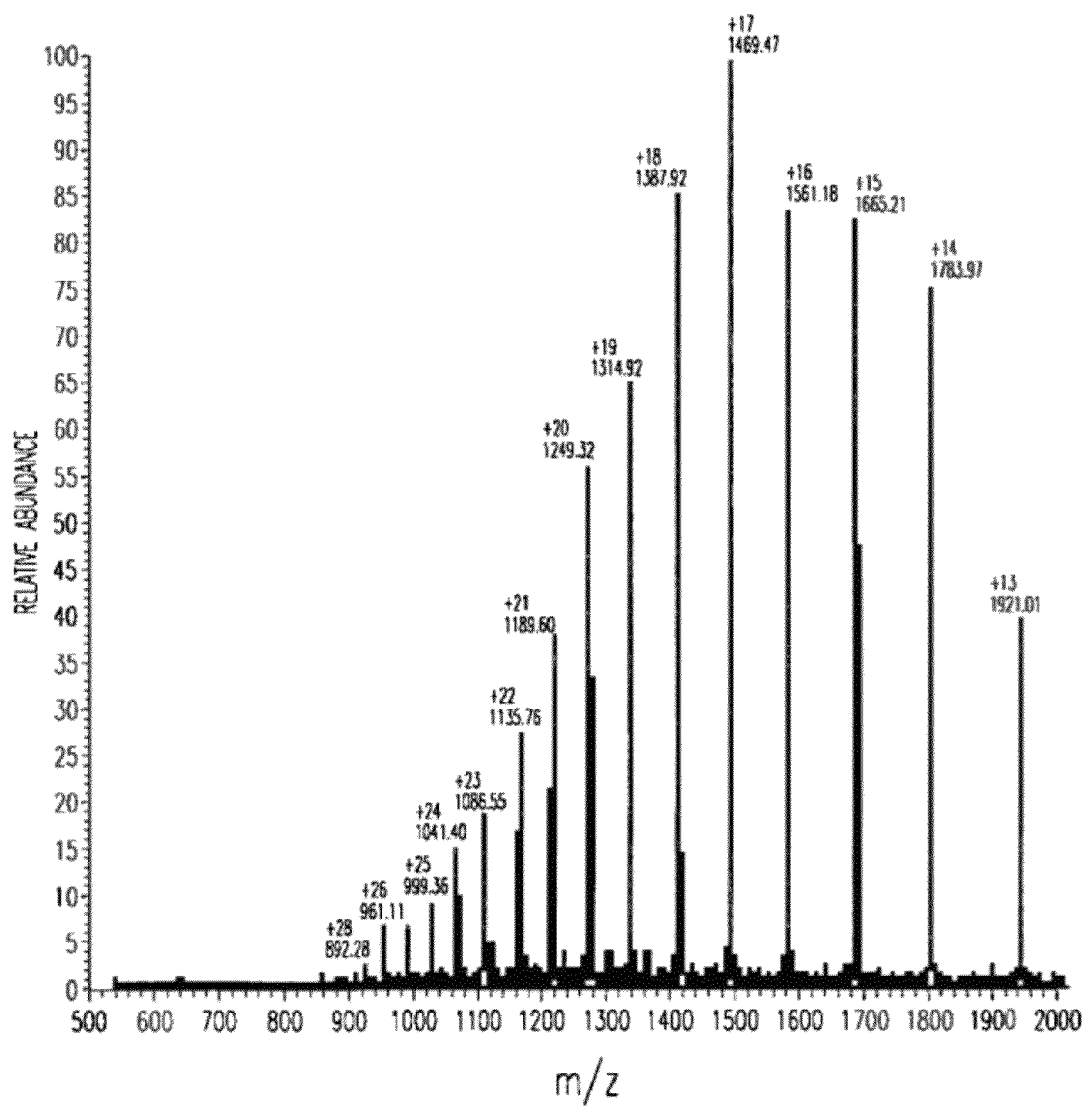

The precursor polypeptide peak area is compared to the peak area from a reference polypeptide standard chromatographed under the same conditions. The precursor polypeptide concentration (FIG. 3A—Peak 1) is determined by normalizing for the different calculated molar absorptivities ($\epsilon_{280\ nm}$) of a standard and the precursor polypeptide, injection volumes, and dilution factors. Alternatively, the molar absorbtivity of the precursor peptide can be estimated from the proportional contributions of the molar absorbtivities at 280 nm of the constituent amino acids. FIG. 3B shows the mass spectrum of Peak 1 of FIG. 3A. The precursor polypeptide had a molecular weight of 24,963.

To monitor the production of a T7tagVg-VDDR-GLP-2(1-33,A2G) (SEQ ID NO:40), or T7tag-GSDR-GLP-1(1-33) A2G-PGDR-GLP-2(1-33,A2G) (SEQ ID NO:39) precursor polypeptide preparation, 100 µL of sample (fermentation culture or from a purification process step) was dissolved in 1 mL 71% phenol, 0.6 M citric acid, vortexed and bath sonicated briefly. The dissolved sample was diluted 12.5-fold to 50-fold in 50% acetonitrile, 0.09% TFA, and centrifuged to render it compatible with the chromatography system to be employed. The dissolved precursor polypeptide and *E. coli* cell products remain soluble in the diluted solution, while other insoluble matters are removed.

The samples were then analyzed using a tapered, 5 µm Magic Bullet C4 column (Michrom BioResources). The absolute peak area of the precursor polypeptide was obtained by recording the absorbance at 280 nm as a function of time. The HPLC method was as follows:
1. Mobile phase: A—0.1% TFA in water, B—0.08% TFA in acetonitrile.
2. Detection: 280 nm.
3. Gradient: 1 mL/min. at 50° C., using 10-90% B(2.5 min.), 90-10% B(0.1 min.), 10% B(1.4 min.). The gradient may be modified for better separation of different precursor peptides.
4. Injection: 1-10 µL.

Figure 3C:
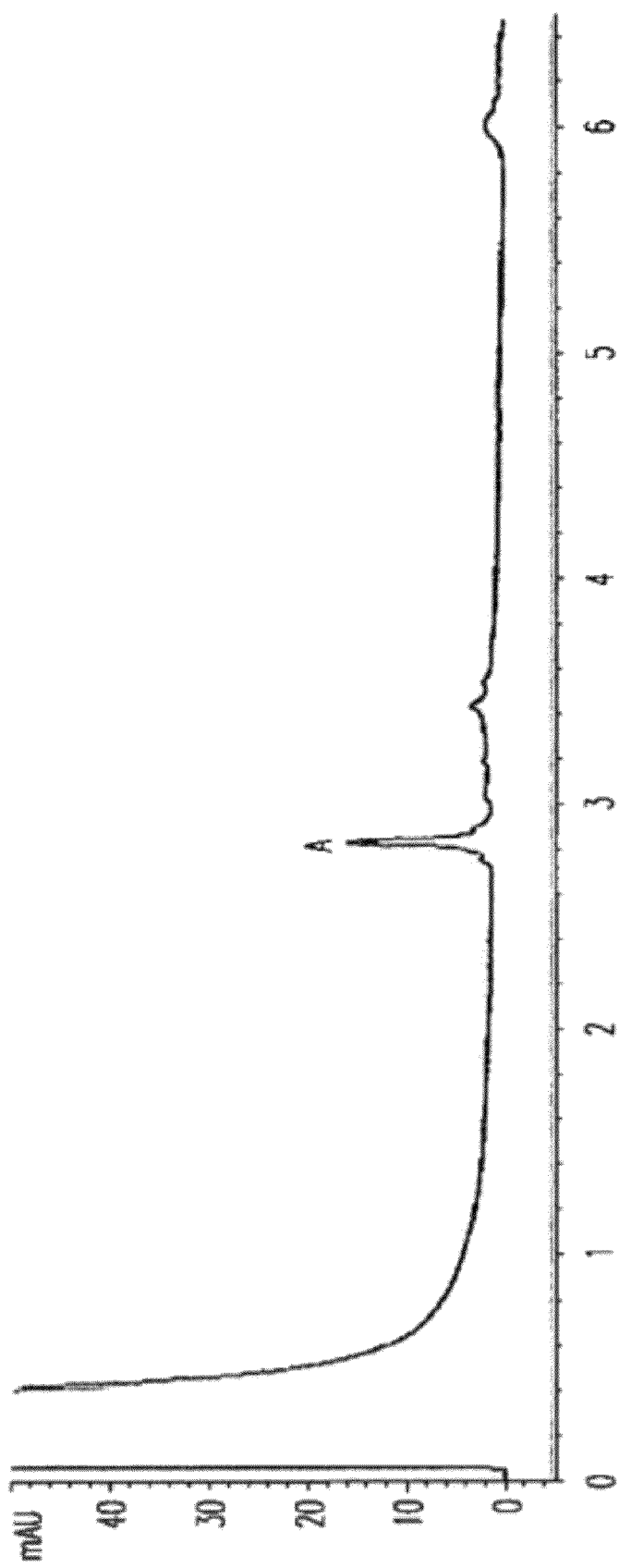
FIGS. 3C and 3D illustrate HPLC analysis of cell free extracts of C) T7tagVg-VDDR-GLP-2(1-33,A2G) (SEQ ID NO:40) (8.7 gm/L); or D: T7tag-GSDR-GLP-1(1-33)A2G-PGDR-GLP-2(1-33,A2G) (SEQ ID NO:39) (10.4 gm/L). In each case cell samples were taken after 10 hours of induction and prepared for analysis as described in the text.
Figure 3D:
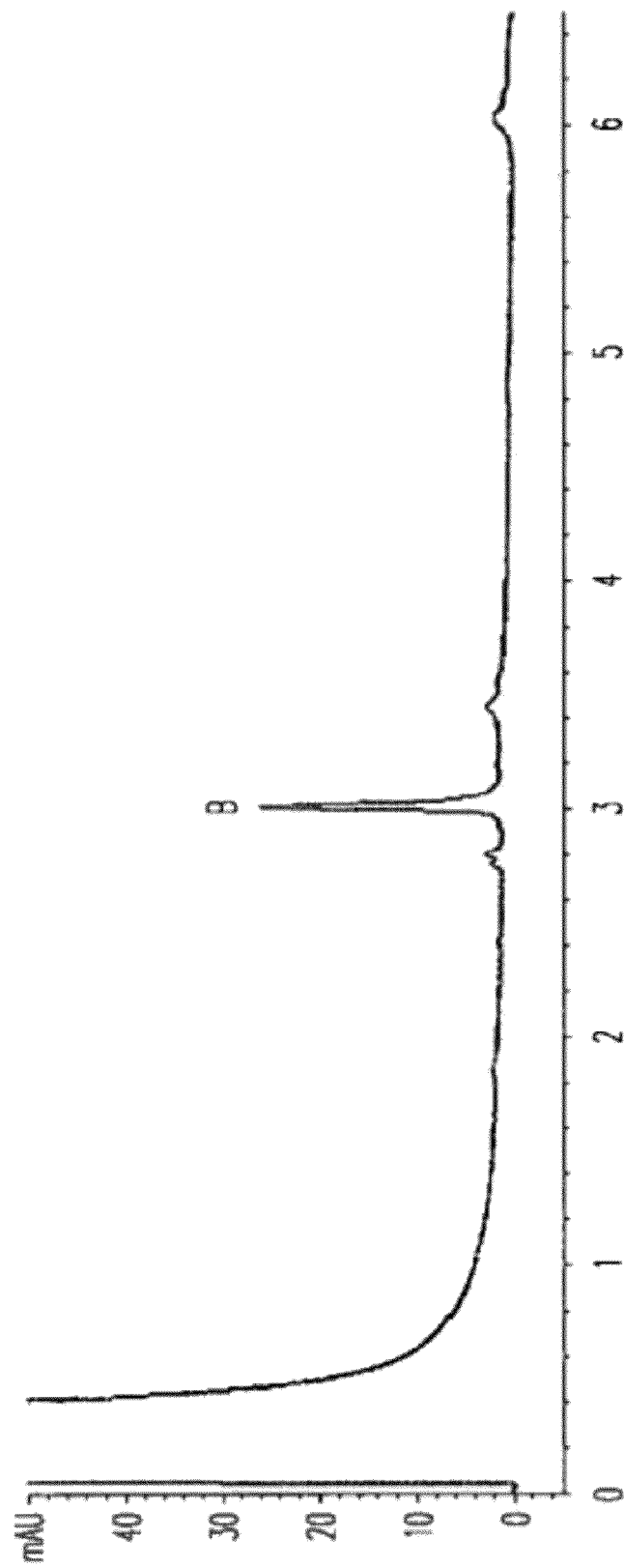

The precursor polypeptide peak area is compared to the peak area from a reference polypeptide standard chromatographed under the same conditions. The precursor polypeptide concentration is determined by normalizing for the different calculated molar absorptivities ($\epsilon_{280\ nm}$) of a standard and the precursor polypeptide, injection volumes, and dilution factors. Alternatively, the molar absorbtivity of the precursor peptide can be estimated from the proportional contributions of the molar absorbances $E_{(280\ nm)}$ of the constituent amino acids. Multiplying the polypeptide concentration times the process step volume yields the total quantity of polypeptide (FIGS. 3C and 3D).

Example 4

Cleavage of Precursor Polypeptides

Figure 4:
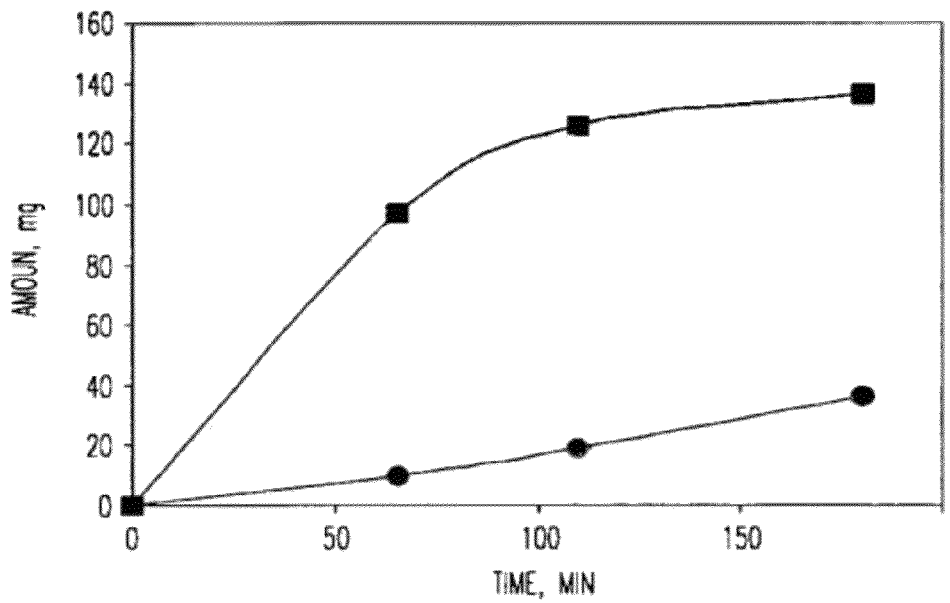
FIG. 4 illustrates the digestion of a precursor polypeptide, T7tag-GSDR-[GLP-2(1-34)]$_6$ (SEQ ID NO:37) in a cell free extract with clostripain to produce GLP-2(1-34)(closed squares) and a GLP-2 fragment (21-34)(closed circle). The digestion was conducted by combining 0.1 unit of clostripain per mg of the precursor polypeptide. The precursor polypeptide was present in the digestion mixture at a concentration of about 0.45 mg/ml.

GLP-2(1-34) precursor polypeptide: About 100 grams of cells resuspended in a buffer containing 50 mm Tris (pH 7.5) and 5 mM EDTA were homogenized in a Ranie high pressure homogenizer to produce a cell free extract. About 45 milliliters of the resulting cell extract containing about 445 mg of the T7tag-GSDR-[GLP-2(1-34)]$_6$ (SEQ ID NO:37) precursor polypeptide was adjusted to pH 6.4 with about 100 ml of NaH$_2$PO$_4$ (100 mM) and the solution was rendered 1 mM CaCl$_2$ and 1 mM DTT. The digestion reaction was initiated by the addition of 0.1 unit of clostripain per milligram of precursor polypeptide. The solution was incubated at 25° C. for approximately 3 hours. The time course of the digestion is shown in FIG. 4.

GLP-2(1-33,A2G) precursor polypeptide: Approximately 100 grams of *E. coli* cells containing the desired precursor polypeptide were lysed by combining them with approximately two liters of 8 M urea containing 0.1 M NH$_4$OH, pH 10.0 (adjusted with reagent grade HCl). This treatment caused the cells to lyse and produce a cell free extract. Alternatively, cells can be lysed with 8 M urea at neutral pH. Lysis methods utilizing urea are preferably used to lyse cells that express soluble precursor polypeptides.

Recombinant clostripain was prepared as 1400 unit/mL solution. Dilutions were made, when necessary, in 25 mM HEPES buffer at pH 7.1 with 10 mM DTT and 5 mM CaCl$_2$ and were stored at 4° C. or in an ice bucket before use.

In one example, the lysate was homogenized for 3 minutes using a commercial homogenizer. The suspension was then centrifuged for 45 minutes at 16,900×g. The supernatant fluid was diluted to a final protein concentration of from 0.1 to 2 mg/ml in 50 mM HEPES buffer, containing 1 mM CaCl$_2$ and 1 mM cysteine. Alternately the lysate was subjected to tangential flow filtration (TFF) using an 8 kD exclusion membrane. The loss in the filtered volume was replaced with 50 mM HEPES containing 0-3 M urea, 1 mM CaCl$_2$, and 1 mM cysteine, pH 6.0-6.9.

For cells that express precursor polypeptides in inclusion bodies, cell lysis was preferably performed by sonication or mechanical homogenization in 50 mM Tris, 2.5 mM EDTA, pH 7.5. Centrifugation was then be performed to sediment the inclusion bodies. After the supernatant fluid was decanted, the pellet was dissolved in 8 M urea, mechanically homogenized for 2 minutes then centrifuged to remove the insoluble material. The supernatant fluid was treated as above to reduce the urea concentration.

Figure 4A:
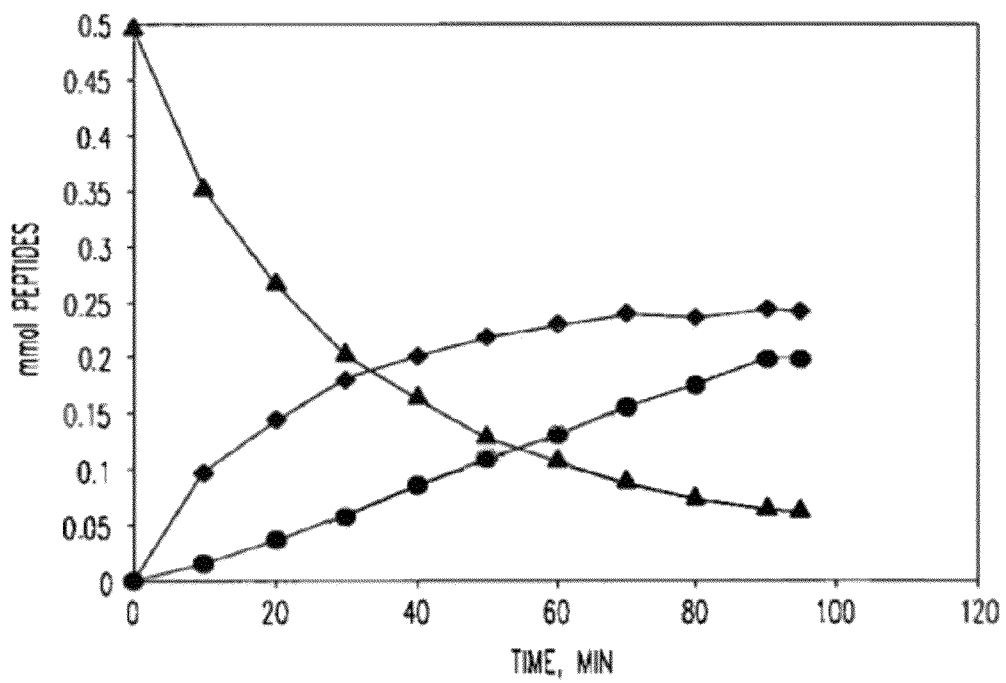
FIG. 4A illustrates the digestion of a precursor polypeptide, T7tagVg-VDDR-GLP-2(1-33,A2G) (SEQ ID NO:40), in a cell free extract with clostripain to produce GLP-2(1-33, A2G) and a GLP-2 fragment (21-33). The digestion was conducted by combining 0.2 units of clostripain per mg of the precursor polypeptide. The precursor polypeptide was present in the digestion mixture at a concentration of about 0.45 mg/ml (closed triangle) T7tagVg-VDDR-GLP-2(1-33,A2G) (SEQ ID NO:40); (closed diamond) GLP-2(1-33,A2G); (closed circle) GLP-2 fragment (21-33).

Enzymatic digestion of the precursor polypeptide was initiated by combining about 0.01 to 2 U/mg of precursor polypeptide and clostripain. In this example, the reaction contained 0.45 mg/ml of precursor polypeptide and 0.2 units of recombinant clostripain per mg precursor polypeptide. The digest was allowed to proceed for up to 3 hours (FIG. 4A).

Example 5

Identification of Reactants and Products Following Digestion of a Precursor Polypeptide by Clostripain The identity of products produced by cleavage of a precursor polypeptide by clostripain was determined by liquid chromatography/mass spectroscopy (LC/MS) analysis. In one example, a cleavage reaction containing clostripain and a T7tag-GSDR-[GLP-2(1-34)]$_6$ (SEQ ID NO:37) precursor polypeptide was assembled that contained 3 mg/ml precursor polypeptide and 0.4 units clostripain per mg of precursor peptide. In another example, a cleavage reaction containing clostripain and a T7tag-GSDR-GLP-2(1-33,A2G)-PGDR-GLP-2(1-33,A2G) (SEQ ID NO:39) precursor polypeptide was assembled that contained 3 mg/ml precursor polypeptide and 0.4 Units clostripain per mg of precursor peptide. The cleavage reactions were conducted for 80 minutes and resulted in a 90% conversion to the indicated products. A 30 µl aliquot was obtained from a cleavage reaction and mixed with 100 µl of a solution containing 8 M urea to which 20 µl of 0.1 M EDTA (pH 6.5) was added. Samples were clarified by centrifugation if needed.

Prepared samples (5 µl) were injected into a Finnigan LCQ DUO ion trap mass spectrometer equipped with a Waters Symmetry C18 column operating in a positive ion electrospray mode for analysis. During the sampling period, molecular weight determination was performed by full scan mass spectrometry. Typical MS conditions included a scan range of 300-2000 Dale.

LC analysis was performed on a system consisting of a Xcaliber software, ThermoQuest Surveyor MS pumps, a ThermoQuest Surveyor UV spectrophotometric PDA detector and a ThermoQuest Surveyor autosampler. The parameters of the chromatagraphic column are indicated below.

| Column: | |
|---|---|
| Manufacturer: | Waters Company |
| Packing support: | Symmetry C18 |
| Particle size: | 3.5 μM |
| Pore size: | 100 Å |
| Column size: | 2.1 × 150 mm |
| Guard column: | 3.5 μm, 2.1 × 10 mm |

Chromatographic conditions were: flow-rate 300 ul/min and buffers A: 0.1% TFA, B: acetonitrile, 0.08% TFA. The gradient was from 15% B to 30% B in 3 minutes, to 55% B in 19 minutes, to 90% B in 3 minutes, temperature 50° C. Detection was over the range 210-320 nm on the PDA detector, Channel A 214 nm, channel B 280 nm. Mass detection was over the 300-2000 Dale range. All the samples were analyzed on an LCQ-DUO ESI mass spectrometer. Usually, the masses observed with significant relative abundance are the doubly or triply charged ions, i.e., $[M+2H]^{2+}/2$ or $[M+3H]^{3+}/3$. The complete mass spectrum as a function of time could be evaluated following the chromatographic procedure through use of the system software. This allows for analysis of individual peaks that eluted from the column.

Figure 5:
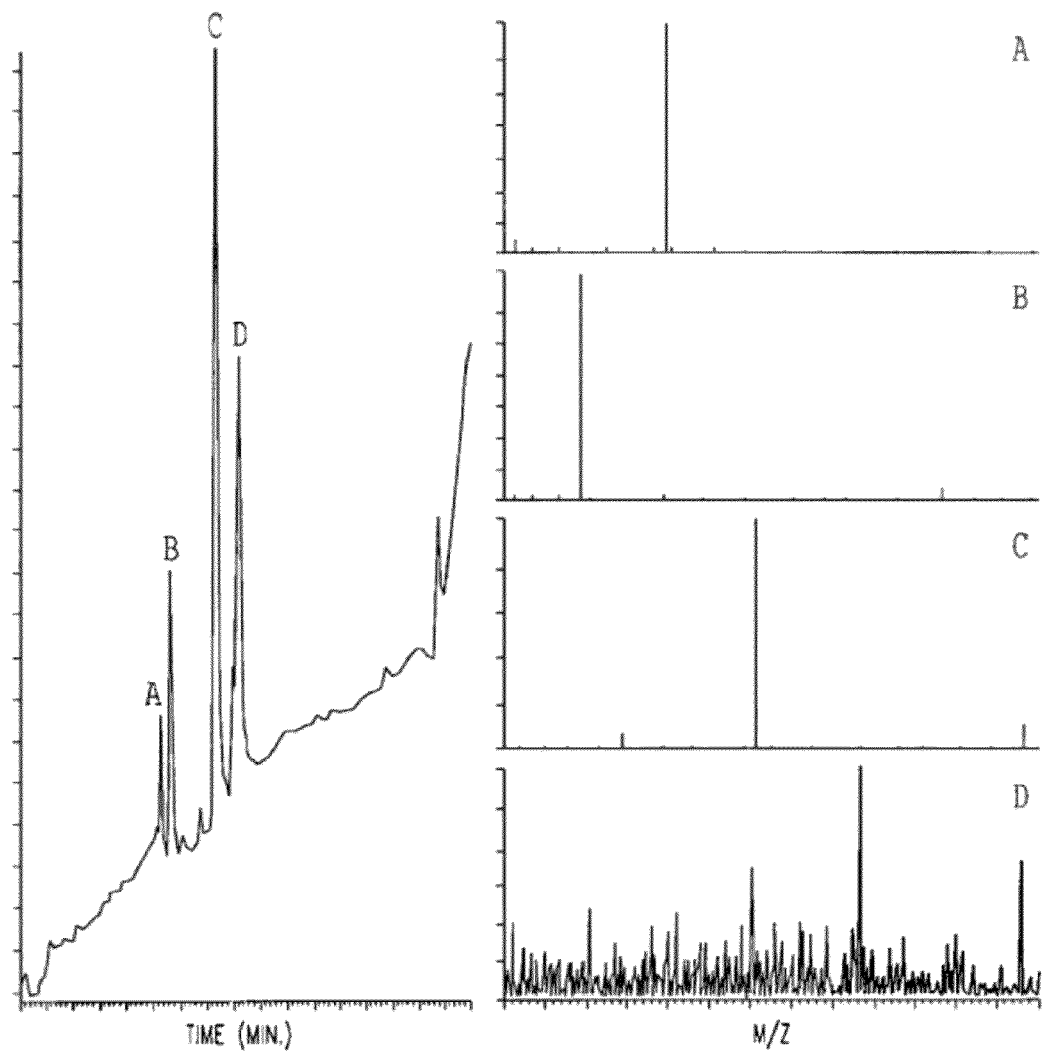
FIG. 5 shows the results of a liquid chromatography-mass spectroscopy (LC/MS) conducted on the products of the precursor polypeptide, T7tag-GSDR-[GLP-2(1-34)]$_6$ (SEQ ID NO:37), after digestion with clostripain. The mass spectra represent the masses of the peak from HPLC. Mass spectrum A was from peak at 8.25 minutes, B from peak at 8.6 minutes, C from peak at 10.24 minutes and D from peak at 11.2 minutes. Peak A was identified as GLP-2(1-20) and had a mass of 2177; Peak B was identified as GLP-2 (21-34) and had a mass of 1763, Peak C was identified as GLP-2(1-34) and had a mass of 3922; and peak D was identified as [(GLP-2(1-34)]$_2$ and has a mass of 7826.
Figure 5A:
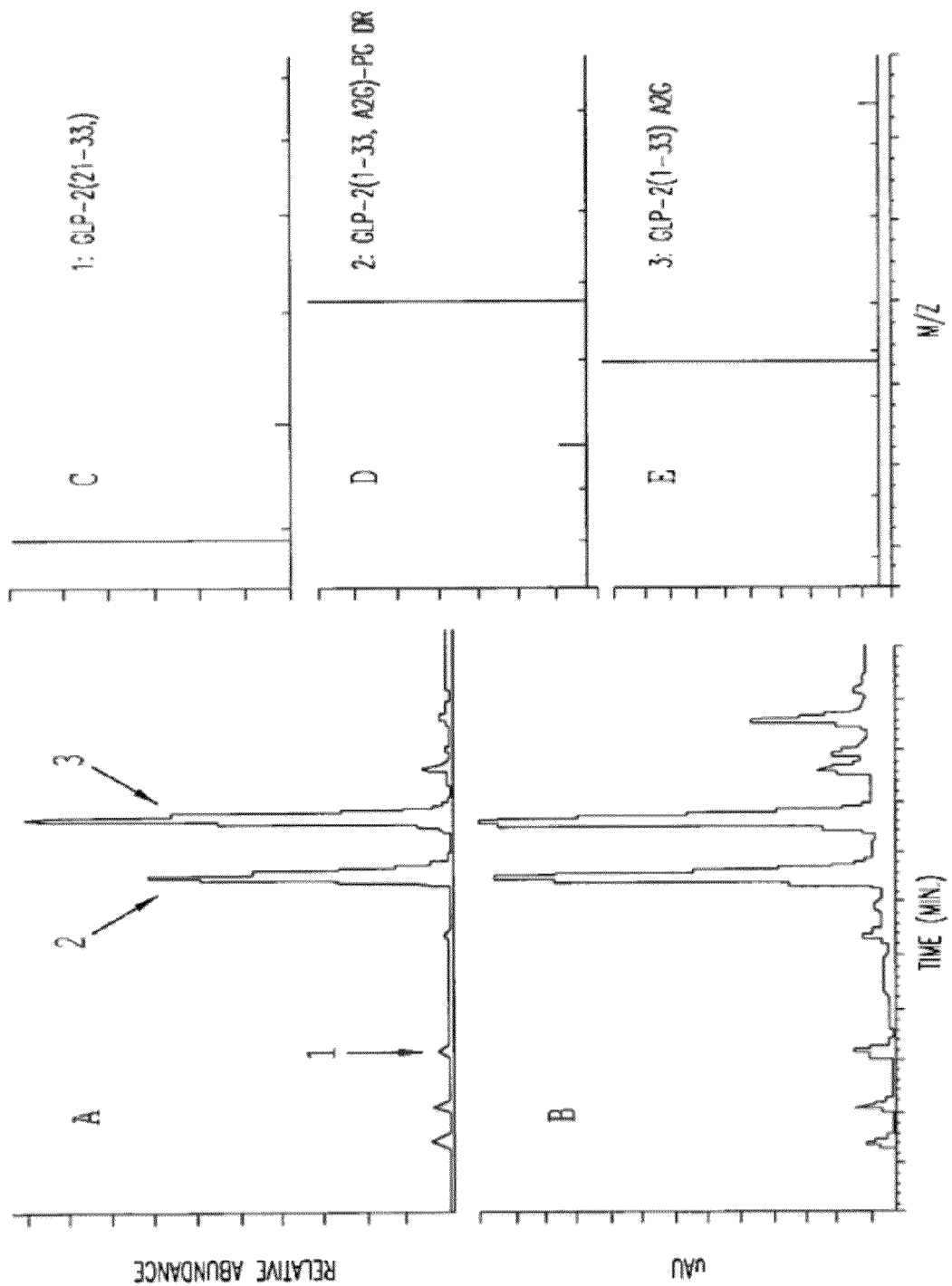
FIG. 5A illustrates typical liquid chromatography-mass spectroscopy (LC-MS) analysis of the reaction products of a clostripain digestion of a precursor polypeptide. Panel (A) shows the relative abundance chromatogram. Panel (B) shows the absorbance chromatogram at A280 nm. Panel (C) shows the mass of peak 1 of panel (A) which correlated to GLP-2(21-33). Panel (D) shows the mass of peak 2 of panel (A) which corresponds to GLP-2(1-33,A2G)-PGDR (SEQ ID NO:41). Panel (E) shows the mass of peak 3 in panel (A) which corresponds to GLP-2(1-33,A2G).

The results shown in FIG. 5 illustrate that the identity of peptides produced in a cleavage reaction can be identified. FIG. 5 shows cleavage at DRH (FIG. 5, yields peptides C and D). The slower cleavage at ARE) of the product C, precursor polypeptide T7tag-GSDR-[GLP-2(1-34)]$_6$ (SEQ ID NO:37) was not detected, thus the reaction went to completion and yields peptides A and B. A purified preparation of GLP-2(1-34)A2G was subjected to complete amino acid sequence analysis which confirmed the structure of this peptide.

FIGS. 5C and 5D also show that cleavage at DRH (FIG. 5C, peaks 2 and 3) is nearly quantitative (90% yield), while the cleavage at ARD (FIG. 5C, peak 1) was minimal. A purified preparation of GLP-2(1-33,A2G) was subjected to complete amino acid sequence analysis which confirmed the structure of this peptide.

Example 6

A. Effects of pH on the Digestion of a Precursor Polypeptide by Clostripain

The pH was varied in a series of clostripain cleavage reactions using the soluble six-copy GLP-2 polypeptide as substrate T7tag-GSDR-GLP-2(1-34)$_6$. In the first set of reactions, the buffer utilized was varied with the pH of the reaction mixture, as follows:

For pH 6.28: 50 mM of Piperazine-NN'-bis(2-ethanesulfonic acid)(PIPES);

For pH 6.55: 4-(2-hydroxyethyl)-1-piperazineethanesulfonic acid)(HEPES);

For pH 7.50: 4-(2-hydroxyethyl)-1-piperazineethanesulfonic acid)(HEPES);

For pH 7.94: 3-(cyclohexylamino)-2-hydroxy-1-propanesulfonic acid)(CAPSO);

For pH 8.82: 3-(cyclohexylamino)-2-hydroxy-1-propanesulfonic acid)(CAPSO).

Figure 6:
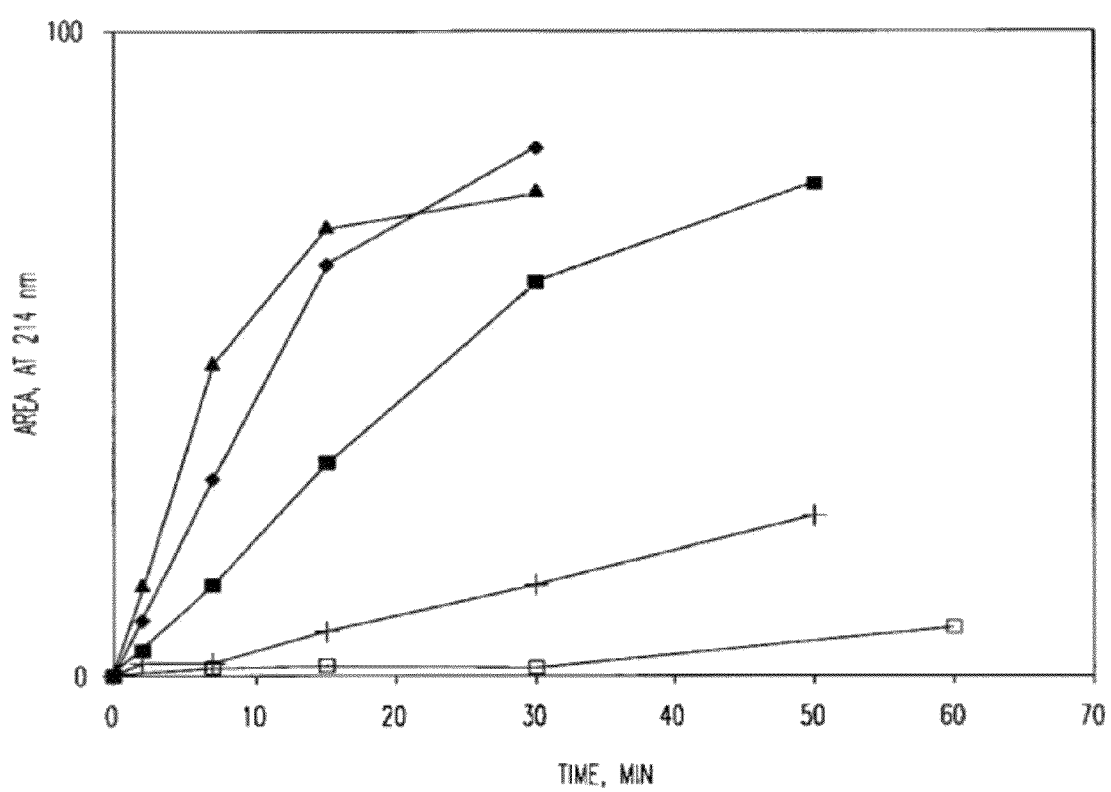
FIG. 6 shows a plot of peak area of GLP-2(1-34) produced from the cleavage reaction as a function of time under different pH conditions; (closed triangles) pH 6.0; (closed diamonds) pH 6.5; (closed squares) pH 7.05; (+ signs) pH 7.63; (open squares) pH 8.0.

The reaction mixture contained 0.33 mg/mL soluble six-copy GLP-2 precursor polypeptide in a cleavage reaction containing 5 mM CaCl$_2$, 10 mM DTT, 4.2 units clostripain per mg of precursor polypeptide, and an appropriate buffer at pH 6.28, 6.55, 7.50, 7.94 or 8.82. The reaction temperature was 20° C. The pH of the cleavage reaction was measured just before addition of clostripain to initiate the reaction. Aliquots of the cleavage reaction were removed at selected time intervals (3, 10, 20 and 40 minutes) and quenched in a volume of a solution containing 7.2 M urea and 1.2 M HCl that was three times the volume of the aliquot. The quenched aliquot was centrifuged before injection into the HPLC. Peptide cleavage products were detected by the HPLC at 214 nm and 280 nm. As illustrated in FIG. 6, the fastest cleavage velocity was observed at a pH range between about 6.0 and about 7.0. However, loss of the GLP-2 monomer by continued internal cleavage was minimized by use of buffer at pH 6.5.

The effect of pH may also be studied in a series of clostripain cleavage reactions using the single copy GLP-2 polypeptide as substrate T7tag-GSDR-GLP-2 (1-33)A2G (SEQ ID NO:44). In the first set of reactions, the buffer utilized may be varied with the pH of the reaction mixture, as follows:

For pH 6.28: 50 mM of Piperazine-NN'-bis(2-ethanesulfonic acid)(PIPES);

For pH 6.55: 4-(2-hydroxyethyl)-1-piperazineethanesulfonic acid)(HEPES);

For pH 7.50: 4-(2-hydroxyethyl)-1-piperazineethanesulfonic acid)(HEPES);

For pH 7.94: 3-(cyclohexylamino)-2-hydroxy-1-propanesulfonic acid)(CAPSO); For pH 8.82: 3-(cyclohexylamino)-2-hydroxy-1-propanesulfonic acid)(CAPSO).

Figure 6A:
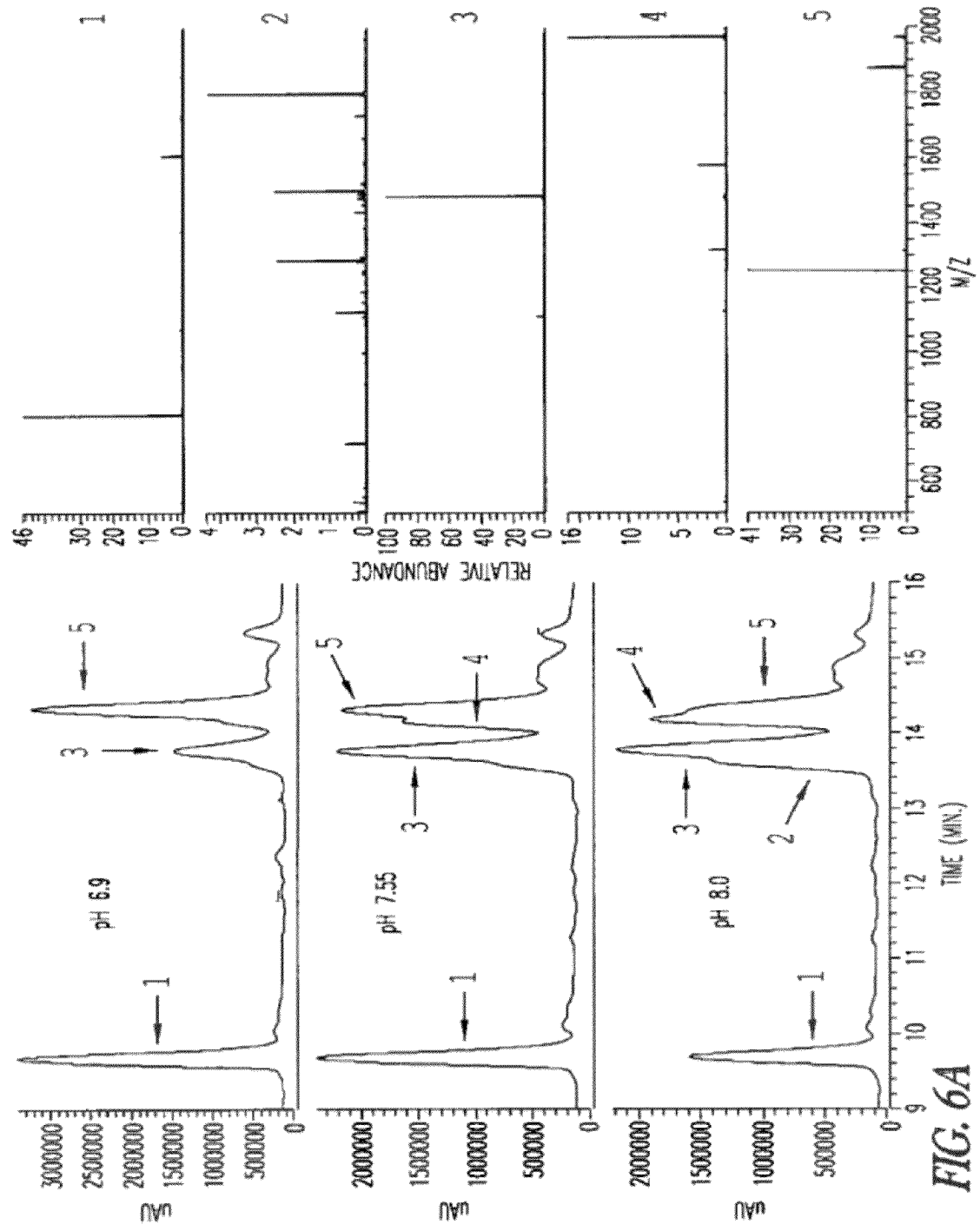
FIG. 6A: illustrates clostripain digestion under different pH conditions. peak 1: GLP-2(21-33), peak 2: T7Vg-GLP-2 (1-33,A2G), peak 3: AMVDDR-GLP-2(1-33,A2G) (SEQ ID NO:42), peak 4: GSGQGQAQYLAASLVVFTNYSGD-TASQVDVVGPRAMVDDR-GLP-2(1-33,A2G) (SEQ ID NO:43), and peak 5: GLP-2(1-33,A2G). At pH 6.9, the greatest transformation of the precursor polypeptide to the peptide product was achieved. The clostripain cleavage reaction above pH 7 is less specific.

The reaction mixture may contain 0.33 mg/mL T7tag-GSDR-GLP-2 (1-33, A2G) (SEQ ID NO:44) precursor polypeptide in a cleavage reaction containing 5 mM CaCl$_2$, 10 mM DTT, 4.2 units clostripain per mg of precursor polypeptide, and an appropriate buffer at pH 6.28, 6.55, 7.50, 7.94 or 8.82. The reaction temperature may be kept at 20° C. The pH of the cleavage reaction may be measured just before addition of clostripain to initiate the reaction. Aliquots of the cleavage reaction can be removed at selected time intervals (3, 10, 20 and 40 minutes) and quenched in a volume of a solution containing 7.2 M urea and 1.2 M HCl that can be three times the volume of the aliquot. The quenched aliquot may be centrifuged before injection into the HPLC. Peptide cleavage products may be detected by the HPLC at 214 nm and 280 nm. As illustrated in FIG. 6A for the cleavage of a GLP-2 (1-33,A2G) substrate tested in a similar study, the fastest cleavage velocity was observed at a pH range between about 6.0 and about 7.0. However, loss of the GLP-2 monomer by continued internal cleavage can be minimized by use of buffer at pH 6.0.

B. Influence of Urea on the Cleavage of a Precursor Polypeptide by Clostripain

Figure 6B:
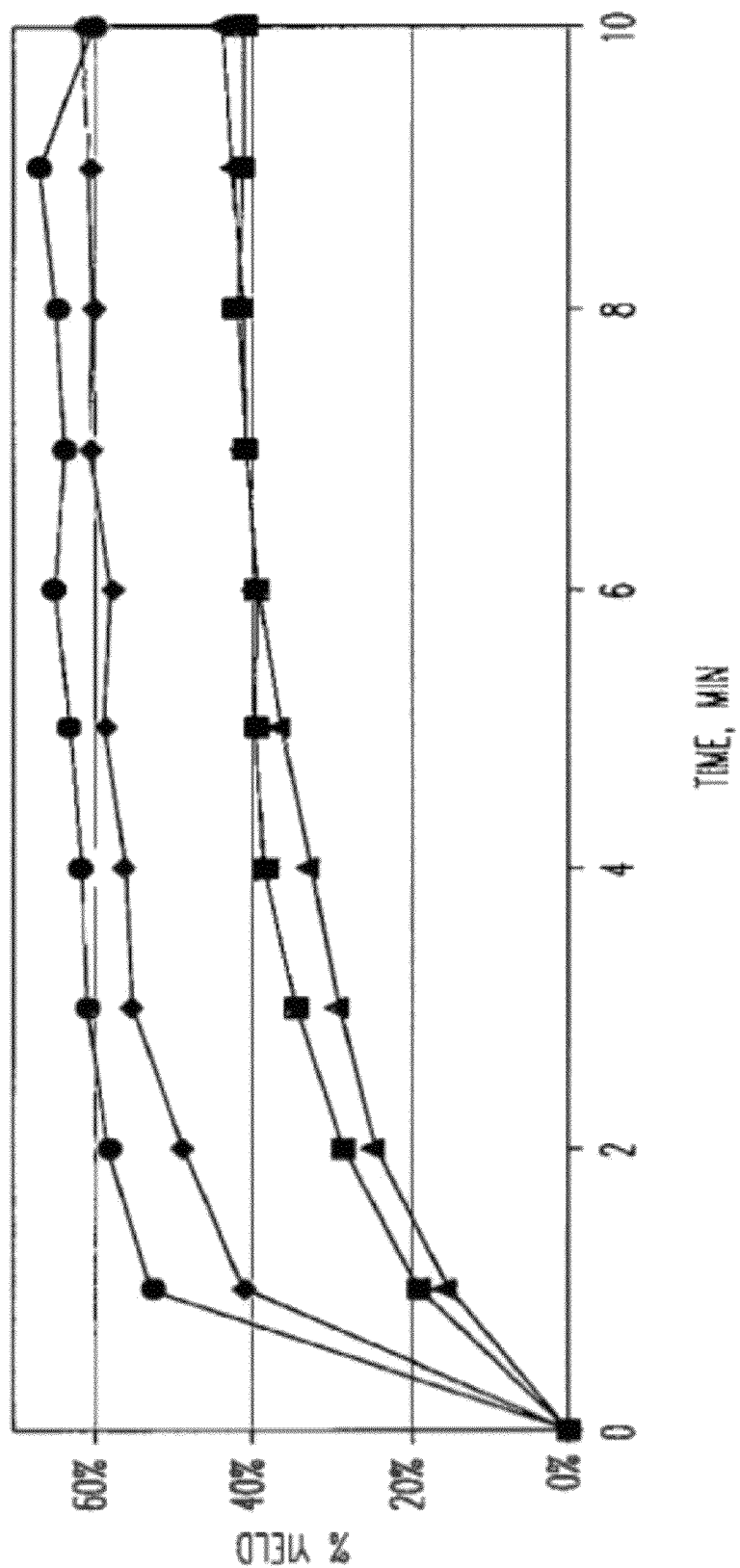
FIG. 6B: shows a plot of percent yield of GLP-2(1-33,A2G) produced from the cleavage reaction as a function of time under different urea concentrations (closed circle) 0 M; (closed diamond) 0.5 M; (closed square) 1.0 M; (closed triangle) 1.5 M urea.

The effect of urea on the cleavage of a precursor polypeptide by clostripain was tested by cleaving a T7tagVg-VDDR-GLP-2(1-33,A2G) (SEQ ID NO:40) precursor polypeptide in the presence of various urea concentrations. The precursor polypeptide (0.4 mg/ml) was cleaved with clostripain (3.3 Units per mg of precursor polypeptide) in a reaction mixture containing 50 mM HEPES buffer (pH 6.3), 1 mM CaCl$_2$, 1 mM cysteine, and various concentrations of urea at 25° C. The urea concentrations tested were 0, 0.5, 1.0 and 1.5 M. Aliquots of the cleavage reaction were removed at one minute intervals for 10 minutes and quenched by addition of EDTA to a final concentration of 10 mM. Peptide cleavage products were analyzed by the HPLC at 214 nm and 280 nm as previously described. As illustrated in FIG. 6B, the fastest cleavage velocity was observed in the absence of urea. Concentrations of urea above 1.5 M caused a decreasing yield to about 20% at 6.5 M urea.

Example 7

The Effect of Precursor Polypeptide and Clostripain Concentration

A. The Effect of Precursor Polypeptide Concentration

The concentration of the soluble six-copy GLP-2 polypeptide T7tag-GSDR-[GLP-2(1-34)]$_6$ (SEQ ID NO:37) was varied in a series of cleavage reactions to ascertain how much precursor polypeptide can optimally be cleaved in a single reaction.

Figure 7A:
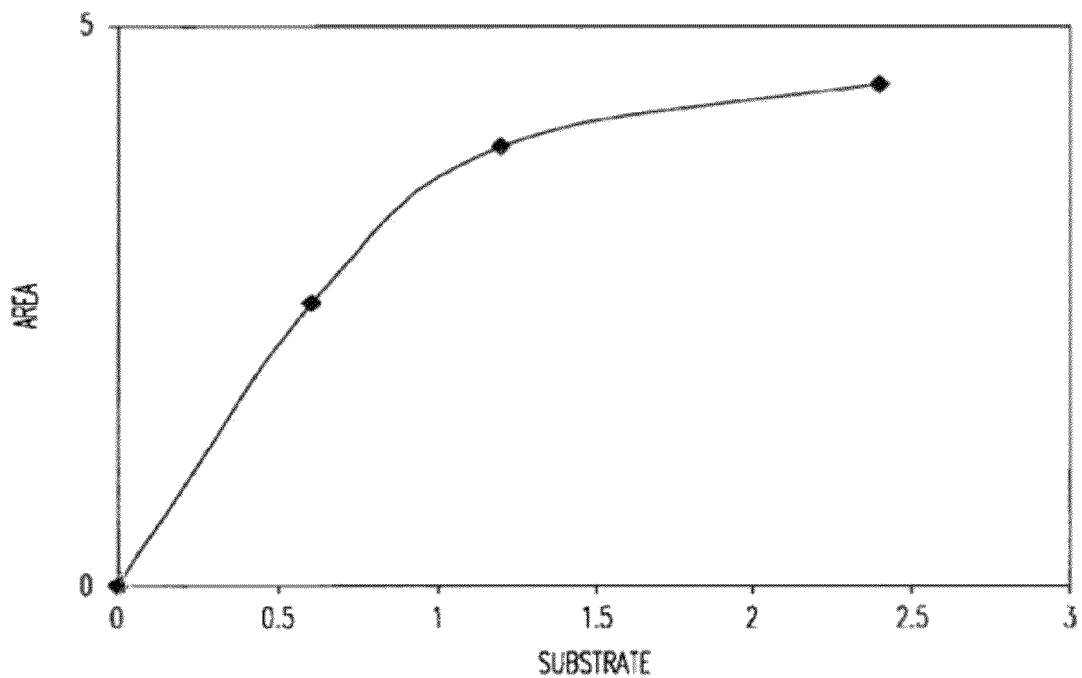
FIG. 7A shows the effect of precursor polypeptide concentration on the rate of cleavage by clostripain.

A stock solution of the soluble six-copy GLP-2 polypeptide was prepared in 10 mM Tris, 1 mM EDTA, 5 mM of CaCl$_2$, pH 8.0 buffer. Aliquots of the substrate stock solution were withdrawn and added to various reaction mixtures as needed. In this series of experiments the substrate concentration was varied within the reaction mixture as follows: 0.6, 1.2, 2.4 and 4.28 mg/mL. The buffer utilized was a phosphate-based buffer at 150 mM (ionic strength about 0.45 M), pH: 6.60±0.01. As before, 10 mM DTT was utilized in the reaction mixture. The reaction temperature was 21° C. and was initiated by the addition of clostripain. Hydrolysis was terminated at 25 minutes by the addition of 3 volumes of 7.2 M urea in 1.2 M HCl. Products of the reaction were analyzed by HPLC according to the procedure described in Example 7. The results of the reaction are shown in FIG. 7A. The yield of GLP-2(1-34) was in excess of 90%.

The identity of the peptide product prepared according to the described method was confirmed by amino acid sequence analysis by LC-MS-MS as being GLP-2(1-34). It was determined that the product had a mass of 3921.9 ([M+3H+]=1308.3 m/z). The designated peak was further fragmented to yield the MS/MS data contained in Table I. The calculated masses are from monoisotopes. The charges of the fragments were also indicated as (M+n H+), where n is the number of additional hydrogen ions.

B. The Effect of Clostripain Concentration

The effect of clostripain concentration on the cleavage of a precursor polypeptide was determined by combining clostripain with T7tag-GSDR-[GLP-2(1-34)]$_6$ (SEQ ID NO:37) at various ratios of clostripain to the precursor polypeptide in a cleavage reaction. The tested ratios were 1, 1/2, 1/4, 1/8 units of clostripain per mg of precursor polypeptide. The concentration of the precursor polypeptide was kept constant at 1.2 mg/ml. The cleavage reaction was conducted in buffer containing 10 mM Tris, 1 mM EDTA, and 5 mM of CaCl$_2$ (pH 8.0) at 21° C. The cleavage reactions were initiated by addition of clostripain to the cleavage reactions. Aliquots were withdrawn at selected time intervals, quenched, and analyzed by HPLC.

Figure 7B:
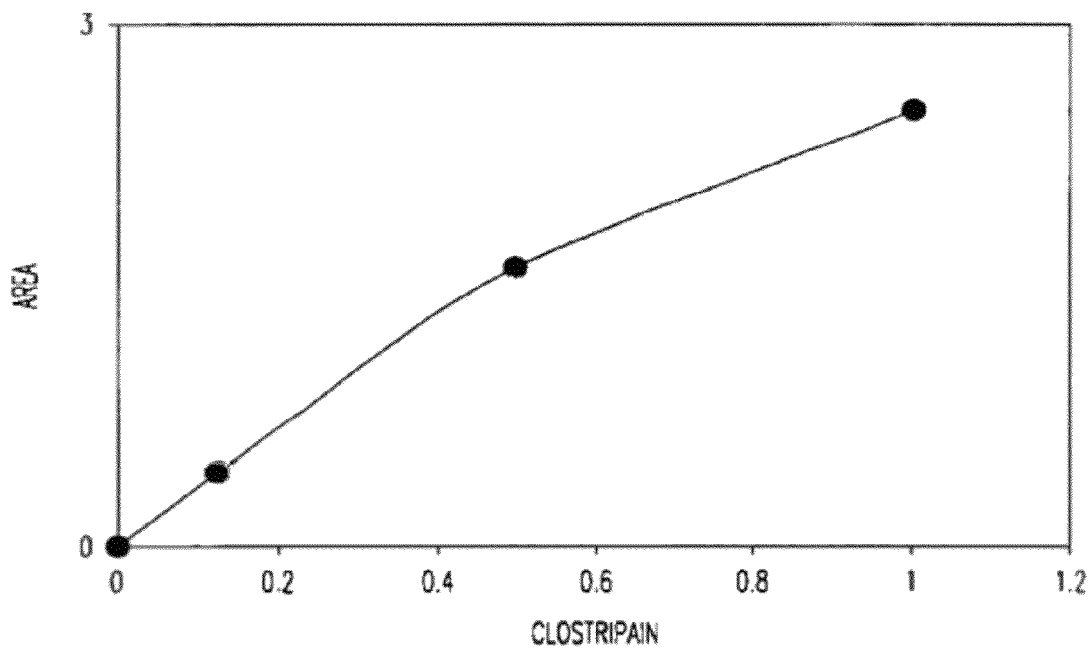
FIG. 7B shows the effect of clostripain concentration on the rate of cleavage of a precursor polypeptide.
Figure 8A:
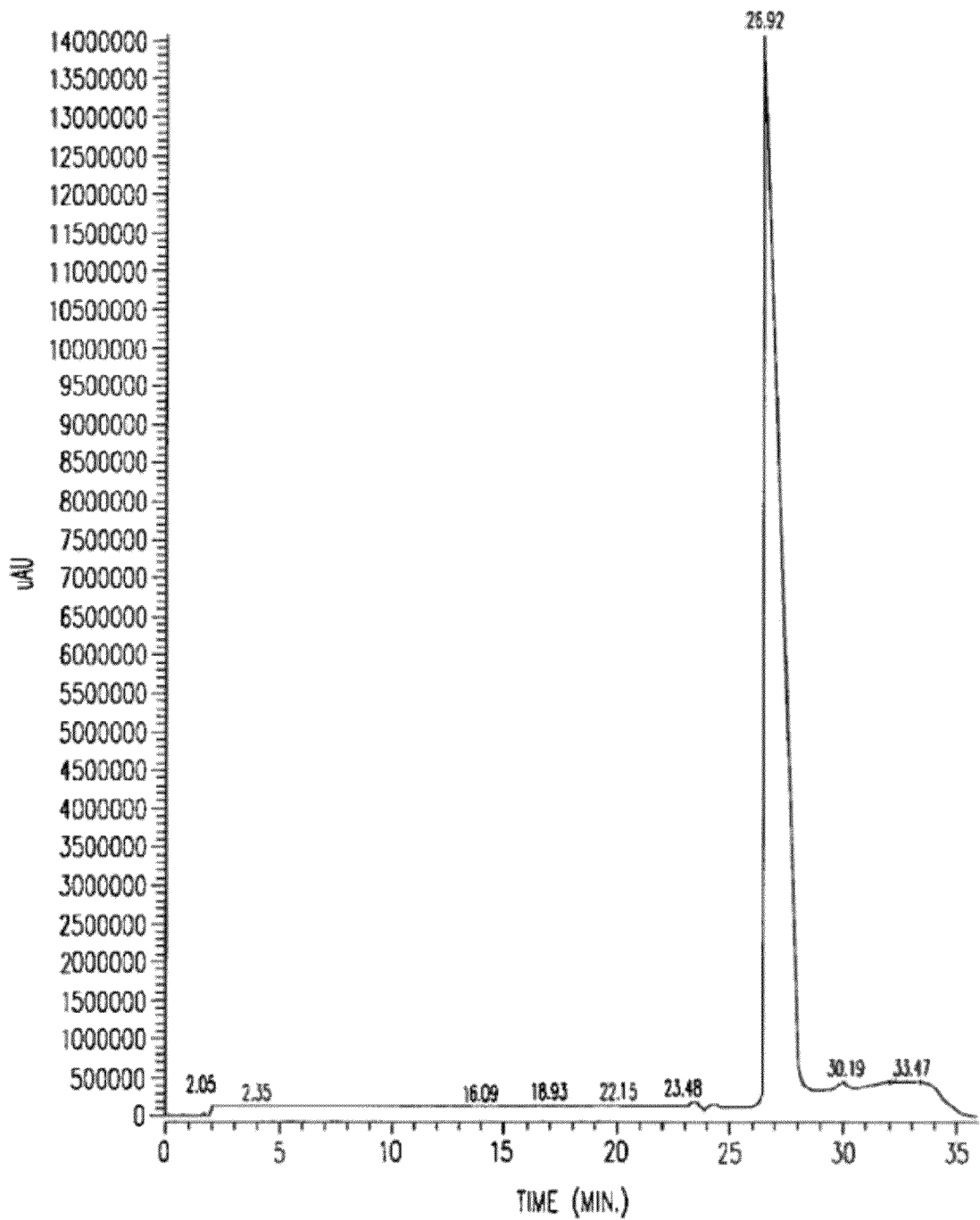
FIG. 8 shows purified GLP-2 (1-34) obtained through use of the methods described in Example 8. Panel A illustrates an HPLC analysis of the purified peptide at the retention time of 26.9 minutes. Panel B illustrates the mass spectrum of the peptide, in which the 1308.5 m/z value is the 3+ charged species. Accordingly the mass is 3922.5 which confirms the identity of GLP-2(1-34).
Figure 8B:
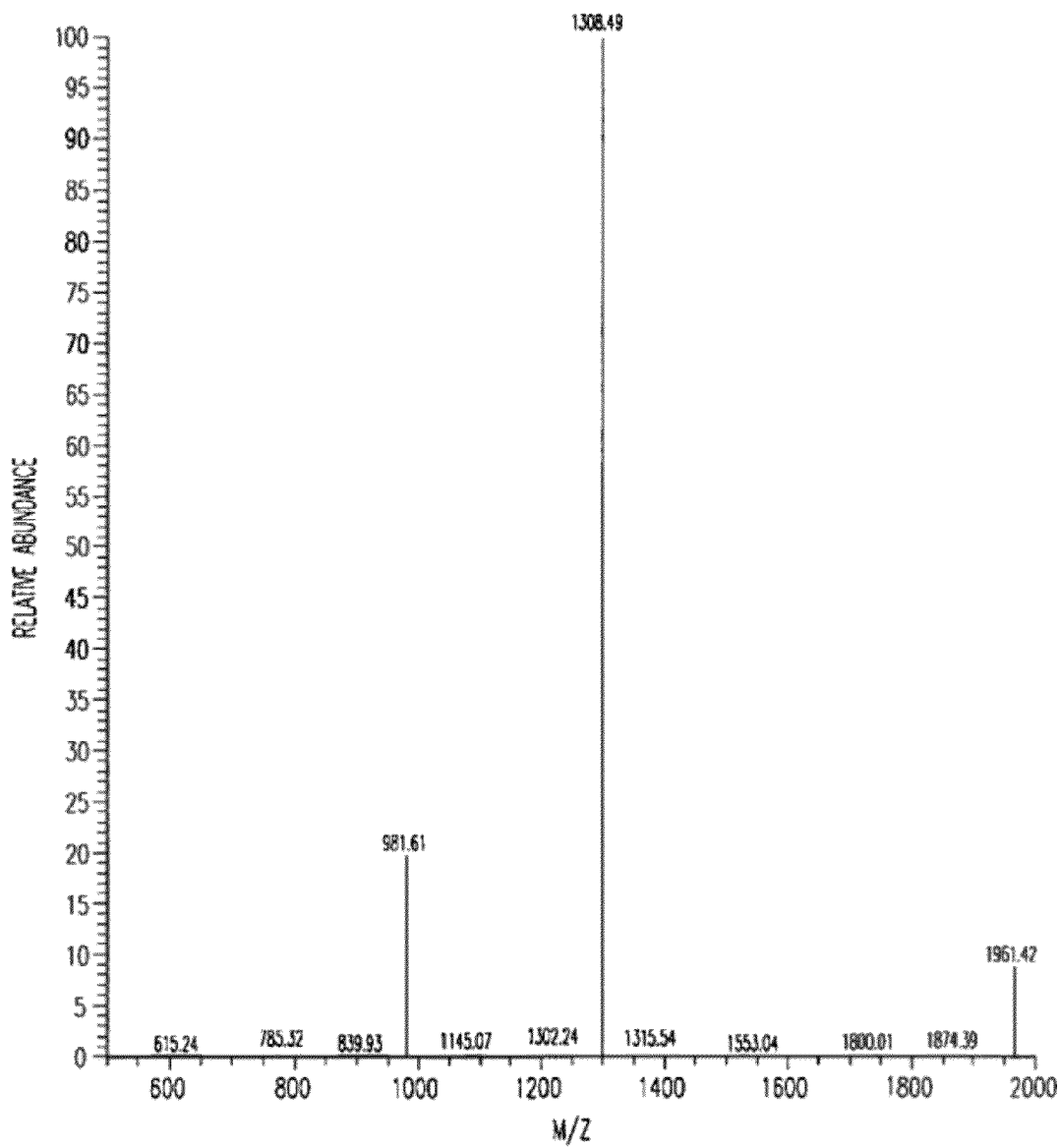

As shown in FIG. 7B, the slowest reaction containing a ratio of 1 unit clostripain per 8 mg of precursor polypeptide was three times slower than the fastest reaction containing a ratio of 1 unit clostripain per 1 mg of substrate. As shown in FIGS. 7A and 7B, a 180 minute reaction at 40° C. containing a ratio of 1 unit clostripain per 20 mg of substrate was approximately equivalent to a 20 minute reaction with 1 unit clostripain per 1 mg of substrate at room temperature. It is noteworthy that a reaction containing only 1 unit clostripain per 100 mg of substrate produced a higher ratio of full length GLP-2(1-34) to truncated GLP-2(21-34). It is also noteworthy that a reaction containing 1 unit clostripain per 20 mg of precursor polypeptide at the ambient room temperature was almost complete at 10 hr and produced less GLP-2(21-34) than did the same reaction at 40° C. after about 3.5 hr. An analytical HPLC of the purified product is shown in FIG. 8.

Example 8

Preparation of Highly Purified GLP-2(1-34)

A solution containing approximately 136 milligrams of GLP-2(1-34) was prepared according to the methods described in Example 4. This solution was applied to an Amberchrom CG-300 column (4.4×8.0 cm, about 121.6 ml) that was equilibrated with buffer A (10% acetonitrile and 5 mM HCl). The sample was loaded at 40 ml/min and washed with buffer A at 40 ml/min. The sample was then eluted with a linear gradient of 10% buffer B (70% acetonitrile and 5 mM Table I Observed Mass of Peptides from the LC-MS Chromatogram

| Fragments | Calc. Mass | Obs. Mass | Conv. Mass | n | SEQ ID NO |
|---|---|---|---|---|---|
| HADGS FSDEM NTILD NLAAR DFINW LIQTK ITDR | 3920.9 | 1308.3 | 3922.08 | 3 | 1 |
| ADGS FSDEM NTILD NLAAR DFINW LIQTK ITDR | 3783.84 | 1262.37 | 3784.11 | 3 | 2 |
| DGS FSDEM NTILD NLAAR DFINW LIQTK ITDR | 3712.8 | 1238.97 | 3713.91 | 3 | 3 |
| GS FSDEM NTILD NLAAR DFINW LIQTK ITDR | 3597.77 | 1200.64 | 3598.92 | 3 | 4 |
| FSDEM NTILD NLAAR DFINW LIQTK ITDR* | 3410.72 | 1138.16 | 3411.48 | 3 | 5 |
| SDEM NTILD NLAAR DFINW LIQTK ITDR* | 3263.65 | 817.22 | 3264.88 | 4 | 6 |
| DGS FSDEM NTILD NLAAR DFINW LIQTK ITDR | 3712.8 | 1857.81 | 3713.91 | 2 | 7 |
| GS FSDEM NTILD NLAAR DFINW LIQTK ITDR | 3597.77 | 1799.95 | 3598.92 | 2 | 8 |
| SDEM NTILD NLAAR DFINW LIQTK ITDR* | 3263.65 | 1634.43 | 3266.8 | 2 | 30 |
| EM NTILD NLAAR DFINW LIQTK ITDR | 3104.59 | 1553.41 | 3104.82 | 2 | 31 |
| ILD NLAAR DFINW LIQTK ITDR | 2629.42 | 1315.68 | 2629.36 | 2 | 32 |
| NLAAR DFINW LIQTK ITDR | 2288.23 | 1144.92 | 2287.84 | 2 | 33 |

*These peptides had lost a CN$_2$H$_3$ fragment (43 au) from an arginine side chain.

HCl) to 70% buffer B in 40 minutes at 30 mL/min. Fractions containing GLP-2(1-34) were pooled. The yield of GLP-2(1-34) was approximately 70%.

The pooled fractions were diluted two fold with dionized water and mixed with solid urea to form a solution having a final urea concentration of about 8 M. A solution containing 1 M N-methyl morpholine (NMM) (50 mL) was then added to produce a solution containing NMM at a final concentration of 50 mM. The final solution volume was 1050 ml. The pH of the solution was adjusted to 8.3 by the addition of HCl to a final concentration of 12 mM. The solution was then filtered through a 0.45 µm membrane filter. This solution was then applied to a Toyopearl super Q-650S column (1.6×11 cm) at a flow rate of 5 ml/min for a period of one hour and 6 mL/min for 2 hours. The column was washed with buffer A (6 M urea, 50 mM NMM (pH 8.3), 12 mM HCl). The sample was then eluted from the column by application of a linear gradient of 0-40% buffer B in 37 minutes at a flow rate of 6 mL/min. Fractions containing GLP-2(1-34) were pooled and diluted to a protein concentration below 0.3 mg/mL with buffer A. The yield was approximately 50%.

The pooled fractions were then diluted two fold with dionized water and acetonitrile was added to a final concentration of about 10%. The sample was then loaded onto a reverse phase HPLC column (Vydac C18) and the column was washed with buffer A (10% acetonitrile and 5 mM HCl) at a flow rate of 10 ml/min. GLP-2(1-34) was then eluted from the column with a linear gradient of buffer B (70% acetonitrile and 5 mM HCl) of 39-46% in 30 minutes and 46% to 100% in 5 minutes. Fractions containing GLP-2(1-34) were pooled and diluted two-fold with deionized water.

The solution of the previous step was applied to a reverse phase HPLC column (Vydac C18) and the column was washed with buffer A (10% acetonitrile and 10 mM HCl) at a flow rate of 10 mL/min. GLP-2(1-34) was eluted with a linear gradient of 39-46% buffer B (70% acetonitrile and 10 mM HCl) in 30 minutes and 46-100% buffer B in 5 minutes. The overall yield of GLP-2(1-34) was about 30% FIG. 8.

Example 9

Production of Variant Forms of GLP-2(1-34), GLP-2(1-34,A2G), and Others

The methods described in examples 1-5 can be used to produce nearly any variant of a GLP-2(1-34) or GLP-2(1-34, A2G). An example of such a variant includes, but is not limited to, GLP-2(1-34,M10L). For example, an expression construct can be constructed that expresses the T7tag-GSDR-[GLP-2(1-34,M10L)]$_6$ (SEQ ID NO:45) or T7tag-GSDR-[GLP-2(1-34)]$_6$A2G (SEQ ID NO:46) precursor polypeptide according to the method described in Example 1. This precursor polypeptide can be expressed and detected according to the methods described in Examples 2 and 3 and then cleaved according to the method of Example 4. The identification of GLP-2(1-34,M10L) as the cleavage product can be conducted according to the methods described in Example 5. Accordingly, analogous methods can be used to create peptide products having virtually any desired amino acid substitution.

Example 10

Figure 9A:
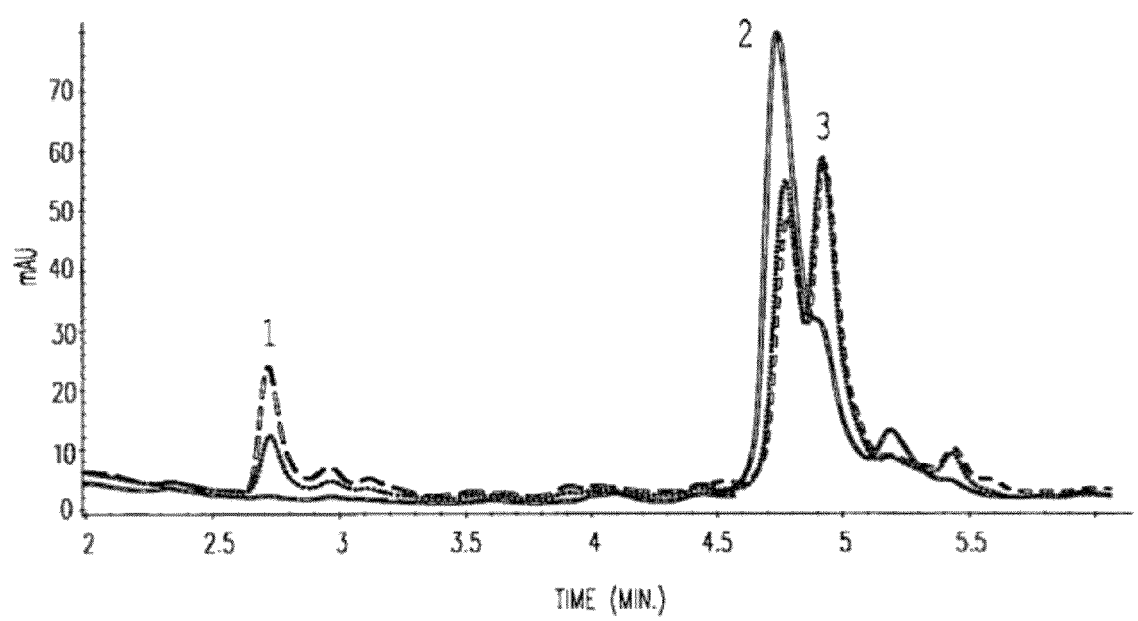
FIGS. 9A and 9B illustrate the effect of organic solvents on the rate and extent of cleavage of a precursor polypeptide T7tagVg-VDDR-GLP-2(1-33,A2G) by clostripain.
Figure 9B:
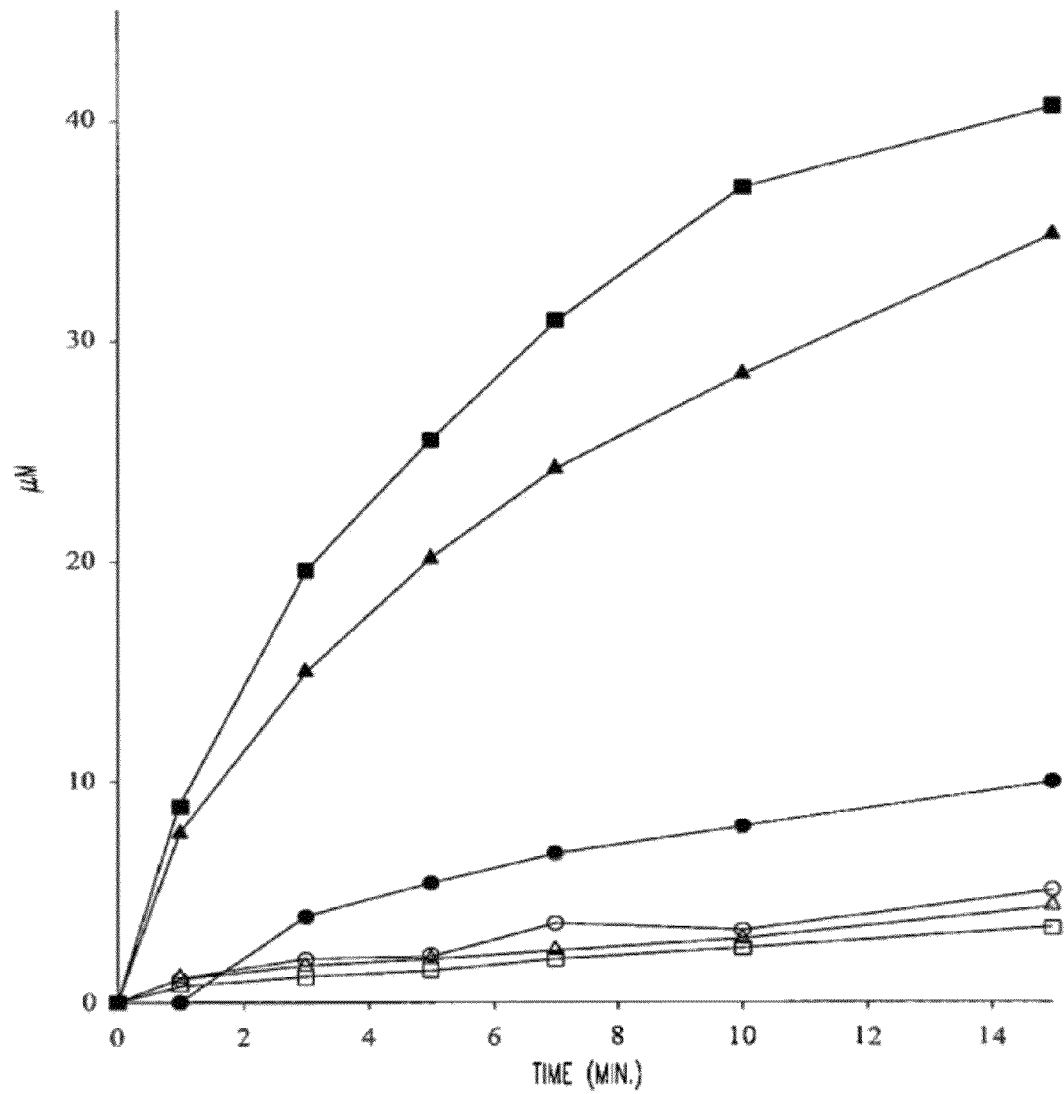

Effect of Organic Solvents on the Digestion of a Precursor Polypeptide by Clostripain The effect of organic solvents on the cleavage of a precursor polypeptide by clostripain was tested by cleaving a T7tagVg-VDDR-GLP-2(1-33,A2G) (SEQ ID NO:40) precursor polypeptide in the presence of various concentrations of ethanol or acetonitrile (FIGS. 9A and 9B).

In one example, the precursor polypeptide (1.2 mg/ml) was cleaved with clostripain (5.0 Units per mg of precursor polypeptide) in a reaction mixture containing 50 mM HEPES buffer (pH 6.7), 1 mM CaCl$_2$, 1 mM cysteine, and 4.8 M urea at 25° C. The ethanol concentrations tested were 10, 20 and 35% ethanol. The reaction was initiated by the addition of clostripain and allowed to proceed for 30 minutes. The reaction was terminated by the addition of EDTA to a final concentration of 17 mM. The products of the cleavage reaction were resolved by C4 reverse phase chromatography. Briefly, a 40 µl sample containing the cleavage products was injected into a Vydac C4 protein column and eluted from the column through application of a gradient composed of Buffer A (5% acetonitrile and 0.1% TFA) and Buffer B (95% acetonitrile and 0.1% TFA). The following gradient was used: time (minutes) 0, % B: 30; time 7.5, % B: 50; time 8.5, % B: 70; time 8.6, % B:30; and time 11, % B:30.

FIG. 9A illustrates the elution position of the major products of digestion (peak 1: GLP-2(21-33), peak 2: GLP-2(1-33,A2G), peak 3: precursor polypeptide). It can be seen that increasing concentrations of ethanol cause a) an increase in the rate of disappearance of the precursor polypeptide (peak 3), b) a concomitant increase in the rate of the appearance of the product (peak 2), and c) a decrease in the appearance of an undesired product (peak 1) produced by cleavage of a secondary cleavage site within the precursor polypeptide.

FIG. 9B illustrates the effects of ethanol and acetonitrile on the cleavage rate, and the extent of cleavage, of a precursor polypeptide by clostripain. It can be seen from the figure that the presence of ethanol or acetonitrile in the cleavage reaction increases the rate of cleavage of a precursor polypeptide as well as increases the yield of cleaved product. Another surprising result is that production of an undesired product produced by cleavage of a second cleavage site within the precursor polypeptide is decreased at increased ethanol or acetonitrile concentrations. These results show that the specificity of clostripain cleavage can be influenced by the presence or absence of an organic solvent in the cleavage reaction. Thus, the discovery that organic solvents can influence clostripain cleavage rate and specificity be used in conjunction with the methods to design clostripain cleavage sites, as disclosed herein, to produce precursor polypeptides that are selectively cleaved to yield desired products in high yield (in excess of 90%).

The complete amino acid sequence of a purified preparation of GLP-2(1-33, A2G) prepared according to the above method was determined to confirm the composition of the peptide product.

Example 11

Production of Gram Quantities of GLP-2(1-33,A2G)

Whole cells (146 g of cells isolated from 1 liter of culture from fermentation) expressing the T7tagVg-VDDR-GLP-2 (1-33,A2G) (SEQ ID NO: 40) precursor polypeptide were suspended in 1 liter of buffer containing 8M urea, 50 mM Hepes buffer (pH 6.9), and homogenized for 5 minutes using a hand held homogenizer (Omni 5000). The suspension was then centrifuged for 30 minutes at 10,000 rpm (Sorvall centrifuge, SLA 3000 rotor) to remove cellular debris. The clear supernatant solution (1000 ml) was found to contain 5.77 grams of precursor polypeptide by analytical reverse-phase HPLC.

For digestion of the precursor polypeptide, the 8M urea supernatant solution containing the precursor polypeptide was diluted with 4 liters of a buffer (40% ethanol:60% 50 mM Hepes buffer (pH 6.9)) and digested for 20 minutes at room temperature with recombinant clostripain (about 15 units of clostripain per mg precursor peptide). The reaction was terminated by the addition of 200 ml EDTA (0.25M) and then centrifuged for 30 minutes to obtain a clear supernatant solution containing 2.1 g of GLP-2(1-33,A2G).

The digestion products were then subjected to anion exchange chromatography. The pH of the digestion reaction containing 2.1 g of the digested GLP-2(1-33,A2G) was adjusted to 8.5 and then loaded onto a column of Toyopearl Super Q 650S (250 ml bed volume) equilibrated with 20 mM Tris buffer pH 8.5. Due to the volume of resin available the chromatography was performed in two stages using ~2.5 liters of digest solution per load. The column was washed with Tris buffer and then eluted sequentially with NaCl solutions at concentrations of 0.1M, 0.3M and 2M in the same buffer. The peptide eluted from the resin with 0.3M salt. Pigmented material and other contaminants were found to elute at both higher and lower salt concentrations. The yield of GLP-2(1-33,A2G) from this chromatography step was 1.8 g.

Figure 10:
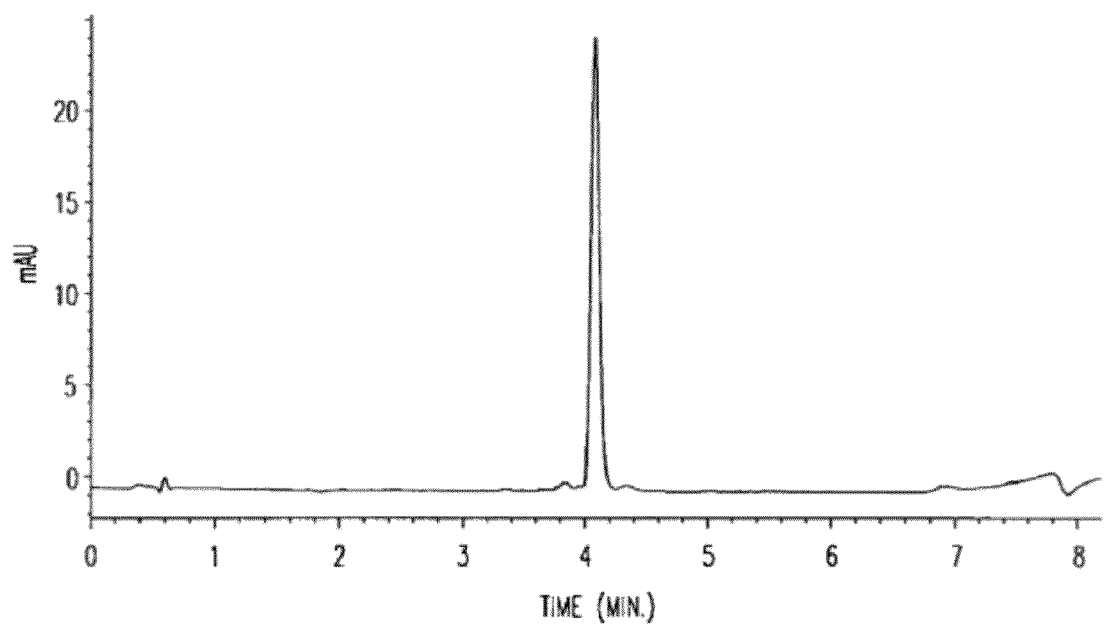
FIG. 10 illustrates is an analytical reverse phase HPLC of purified GLP-2(1-33,A2G). Chromatography was performed using an Alltima C18 column (7×33 mm, resin size is 3.5 µm). The mobile phase was (A) 0.1% TFA in water and (B) 0.08% TFA in acetonitrile. The flow rate was 2 ml per minute and the column was maintained at 50° C. The column was equilibrated with 15% (B) and 85% (A). The gradient was formed from 15% to 45% (B) in 1 minute, 35% to 50% (B) in 5 minutes, and 50% to 90% (B) in 1 minute. The GLP-2(1-33, A2G) eluted in about 4.8 minutes.

The GLP-2(1-33,A2G) prepared by ion-exchange chromatography was loaded onto a column of Amberchrome CG-71 (1 liter bed volume) equilibrated with 5 mM HCl for reverse phase chromatography. The resin was washed with 20 mM Tris buffer pH 8.5 and then eluted with 5% ethanol, 5 mM HCl followed by 40% ethanol, 10% iso-propanol, 5 mM HCl. Approximately 65% of the GLP-2(1-33,A2G) eluted from the column with the 5% ethanol solution while the remainder appeared to be more tightly bound and eluted with 40% ethanol. The GLP-2(1-33,A2G) prepared in this manner exhibited a purity of about 97% when analyzed by reverse phase HPLC. The total recovery of GLP-2(1-33,A2G) was 1.1 gram. The GLP-2(1-33,A2G) produced according to this method had the correct mass and amino acid sequence. FIG. 10 illustrates an analytical reverse phase chromatogram of a sample of the purified material under the conditions of the analysis.

Example 12

Production of Variant Forms of GLP-2(1-33) and GLP-2(1-33,A2G)

The methods described in Examples 1-5 can be used to produce nearly any variant of a GLP-2(1-33) or GLP-2(1-33,A2G). An example of such a variant includes, but is not limited to, GLP-2(133,M10L). For example, an expression construct can be constructed that expresses the T7tagVg-VDDR-GLP-2(1-33,M10L) (SEQ ID NO:40) or T7tag-GLP-2(1-33,A2G)-GPDR-GLP-2(1-33,M10L) (SEQ ID NO:47) precursor polypeptide according to the method described in Example 1. This precursor polypeptide can be expressed and detected according to the methods described in Examples 2 and 3 and then cleaved according to the method of Example 4. The identification of GLP-2(1-33,M10L) as the cleavage product can be conducted according to the methods described in Example 5. Accordingly, analogous methods can be used to create peptide products having virtually any desired amino acid substitution.

REFERENCES

Alberts et al., *Molecular Biology of the Cell*, 2nd ed., 1989
Amann et al., *Gene*, 25:167 (1983)
Amann et al., *Gene*, 40: 183, (1985)
Aubin et al., *Methods Mol. Biol.*, 62:319 (1997)
Augustin et al., *FEMS Microbiol. Lett.*, 66: 203 (1990)
Ausubel et al., *Current Protocols in Molecular Biology*, Green Publishing Associates and Wiley Interscience, NY (1989)
Barany et al., *J. Bacteriol.*, 144: 698 (1980)
Beach and Nurse, *Nature*, 300:706 (1981)
Beaucage and Caruthers, *Tetra. Letts.*, 22:1859 (1981)
Boshart et al., *Cell*, 41:521 (1985)
Botstein, et al., *Gene*, 8:17 (1979)
Brake et al., *Proc. Natl. Acad. Sci. USA*, 81:4642 (1984)
Butt et al., *Microbiol. Rev.*, 51:351 (1987)
Carbonell et al., *Gene*, 73: 409 (1988)
Carbonell et al., *J. Virol.*, 56:153 (1985)
Catsimpoolas and Wood, *J. Biol. Chem.*, (1979)
Chaney et al., *Somat. Cell Mol. Genet.*, 12:237 (1986)
Chang et al., *Nature*, 198:1056 (1977)
Chassy et al., *FEMS Microbiol. Lett.*, 44: 173 (1987)
Cohen et al., *Proc. Natl. Acad. Sci. USA*, 69: 2110 (1973)
Cohen et al., *Proc. Natl. Acad. Sci. USA*, 77:1078 (1980)
Cregg et al., *Mol. Cell. Biol.*, 5: 3376, (1985)
Das et al., *J. Bacteriol.*, 158: 1165 (1984)
Davidow et al., *Curr. Genet.*, 10:39 (1985)
Davies et al., *Ann. Rev. Microbiol.*, 32: 469, 1978
Dayhoff et al., Atlas of Protein Sequence and Structure, Natl. Biomed. Res. Found., Washington, C.D. (1978)
de Boer et al., *Proc. Natl. Acad. Sci. USA*, 80:21 (1983)
De Louvencourt et al., *J. Bacteriol.*, 154:737 (1983)
Dijkema et al., *EMBO J.*, 4:761 (1985)
Dower et al., *Nuc. Acids Res.*, 16: 6127 (1988)
Dykes et al., *Eur. J. Biochem.*, 174: 411 (1988)
EPO Publ. Nos. 036 259 and 063 953
EPO Publ. Nos. 036 776, 136 829 and 136 907
EPO Publ. No. 121 775
EPO Publ. No. 127 328
EPO Publ. Nos. 127 839 and 155 476
EPO Publ. No. 164 556
EPO Publ. No. 267 851
EPO Publ. No. 329 203
Feigner et al., *Proc. Natl. Acad. Sci.*, 84:7413 (1987)
Feigner et al., *J. Biol. Chem.*, 269:2550 (1994)
Fiedler et al., *Anal. Biochem*, 170: 38 (1988)
Forsberg et al., *Biofactors*, 2: 105-112, (1989)
Forsberg et al., *Int. J. Protein Chem.*, 11: 201-211, (1992)
Franke and Hruby, *J. Gen. Virol.*, 66:2761 (1985)
Fraser et al., *In Vitro Cell. Dev. Biol.*, 25:225 (1989)
Freifelder, Physical Biochemistry: Applications to Biochemistry and Molecular Biology, W.H. Freeman and Co., 2nd edition, New York, N.Y. (1982).
Friesen et al., "The Regulation of Baculovirus Gene Expression", in: The Molecular Biology of Baculoviruses (ed. Walter Doerfler), 1986
Gaillardin et al., *Curr. Genet.*, 10:49 (1985)
Ghrayeb et al., *EMBO J.*, 3: 2437 (1984)
Gleeson et al., *J. Gen. Microbiol.*, 132:3459 (1986)
Gluzman, *Cell*, 23:175 (1981)
Goeddel et al., *Nuc. Acids Res.*, 8:4057 (1980)
Gorman et al., *Proc. Natl. Acad. Sci. USA*, 79:6777 (1982b)
Graham and van der Eb, *Virology*, 52:456 (1973)
Gram et al., *Bio/Technology*, 12: 1017-1023, (1994)
Guan et al., *Gene*, 67:21 (1997)
Harlander, "Transformation of *Streptococcus lactis* by electroporation", in: *Streptococcal Genetics* (ed. J. Ferretti and R. Curtiss III), (1987)
Henikoff et al., *Nature*, 283:835 (1981); Hollenberg et al., *Curr. Topics Microbiol. Immunol.*, 96:119 (1981)

Hinnen et al., *Proc. Natl. Acad. Sci. USA*, 75:1929 (1978)
Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979
Ito et al., *J. Bacteriol.*, 153:163 (1983)
Kaufman et al., *Mol. Cell. Biol.*, 9:946 (1989)
Kawai and Nishizawa, *Mol. Cell. Biol.*, 4:1172 (1984)
Knott et al., *Eur. J. Biochem.*, 174: 405-410, (1988)
Kunkel, *Proc. Natl. Acad. Sci. USA*, 82:488, (1985)
Kunkel et al., *Methods in Enzymol.*, 154:367 (1987)
Kunze et al., *J. Basic Microbiol.*, 25:141 (1985)
Kurtz et al., *Mol. Cell. Biol.*, 6:142 (1986)
Kushner, "An improved method for transformation of *Escherichia coli* with ColE1-derived plasmids", in: Genetic Engineering: Proceedings of the International Symposium on Genetic Engineering (eds. H. W. Boyer and S. Nicosia), (1978)
Labouesses B., *Bull. Soc. Chim. Biol.*, 42: 1293, (1960)
Lebacq-Verheyden et al., *Mol. Cell. Biol.*, 8: 3129 (1988)
Luckow and Summers, *Virology*, 17:31 (1989)
Maeda et al., *Nature*, 315:592 (1985)
Mandel et al., *J. Mol. Biol.*, 53: 159 (1970);
Maniatis et al., *Science*, 236:1237 (1987)
Marcus, *Int. J. Peptide Protein Res.*, 25: 542-546, (1985)
Martin et al., *DNA*, 7: 99 (1988)
Marumoto et al., *J. Gen. Virol.*, 68:2599 (1987)
Masson et al., *FEMS Microbiol. Lett.*, 60: 273 (1989)
Masui et al., in: Experimental Manipulation of Gene Expression, (1983)
McCarroll and King, *Curr. Opin. Biotechnol.*, 8:590 (1997)
Mercerau-Puigalon et al., *Gene*, 11:163 (1980)
Miller et al., *Ann. Rev. Microbiol.*, 42:177 (1988)
Miller et al., *Proc. Natl. Acad. Sci. USA*, 8: 856 (1988)
Miller et al., *Bioessays*, 4:91 (1989)
Mitchell W., *Meth. of Enzymol.*, 47: 165-170 (1977)
Mitchell, W. M, Harrington, W. F., *J. of Biol. Chem.*, 243 (18): 4683-4692 (1968)
Miyajima et al., *Gene*, 58: 273 (1987)
Moks et al., *Bio/Technology*, 5: 379-382, (1987)
Myanohara et al., *Proc. Natl. Acad. Sci. USA*, 80:1 (1983)
Neuman et al., *EMBO J.*, 1:841 (1982)
Oka et al., *Proc. Natl. Acad. Sci. USA*, 82: 7212 (1985)
Orr-Weaver et al., *Methods in Enzymol.*, 101:228 (1983)
Palva et al., *Proc. Natl. Acad. Sci. USA*, 79: 5582 (1982)
Panthier et al., *Curr. Genet.*, 2:109 (1980)
Perry et al., *Infec. Immun.*, 32: 1295 (1981)
PCT Publ. No. WO 84/04541
PCT Pub. No. WO 89/046699
Piers et al., *Gene*, 134: 7, (1993)
Pilon et al., *Biotechnol. Prog.*, 13 374-379 (1997)
Powell et al., *Appl. Environ. Microbiol.*, 54: 655, (1988)
Raibaud et al., *Ann. Rev. Genet.*, 18:173 (1984)
Ray et al., *Bio/Technology*, 11: 64 (1993)
Rine et al., *Proc. Natl. Acad. Sci. USA*, 80:6750 (1983)
Roggenkamp et al., *Mol. Gen. Genet.*, 202:302 (1986)
Sambrook and Russell, Molecular Cloning: A Laboratory Manual, 3rd edition (Jan. 15, 2001) Cold Spring Harbor Laboratory Press, ISBN: 0879695765
Sanford et al., *Methods Enzymol.*, 217:483 (1993)
Sassone-Corsi and Borelli, *Trends Genet.*, 2:215 (1986)
Schellenberger et al., *Int. J. Peptide Protein Res.*, 41: 326 (1993)
Shen, *Proc. Nat'l. Acad. Sci. (USA)*, 281: 4627 (1984)
Shimatake et al., *Nature*, 292:128 (1981)
Shimizu et al., *Mol. Cell. Biol.*, 6:1074 (1986)
Shine et al., *Nature*, 254: 34, (1975)
Smith et al., *Proc. Natl. Acad. Sci. USA*, 82: 8404 (1985)
Smith et al., *Mol. Cell. Biol.*, 3:2156 (1983)
Somkuti et al., *Proc. 4th Eur. Cong. Biotechnology*, 1: 412 (1987)
Steitz et al., "Genetic signals and nucleotide sequences in messenger RNA", in: Biological Regulation and Development: Gene Expression (ed. R. F. Goldberger) (1979)
Studier et al., *J. Mol. Biol.*, 189:113 (1986)
Stinchcomb et al., *J. Mol. Biol.*, 158:157 (1982)
Summers and Smith, Texas Agricultural Experiment Station Bulletin No. 1555, 1987.
Tabor et al., *Proc. Natl. Acad. Sci. USA*, 82:1074 (1985)
Taketo, *Biochim. Biophys. Acta*, 949: 318 (1988)
U.S. Pat. No. 4,336,336
U.S. Pat. No. 4,551,433
U.S. Pat. No. 4,689,406
U.S. Pat. No. 4,738,921
U.S. Pat. No. 4,745,056
U.S. Pat. Nos. 4,837,148 and 4,929,555
U.S. Pat. No. 4,873,192
U.S. Pat. Nos. 4,876,197 and 4,880,734
U.S. Pat. No. 5,595,887 to Coolidge et al.
U.S. Pat. No. 5,707,826 to Wagner et al.
U.S. Pat. No. 6,316,224
Vaheri and Pagano, *Virology*, 27:434 (1965)
Van den Berg et al., *Bio/Technology*, 8:135 (1990)
VanDevanter et al., *Nucleic Acids Res.*, 12:6159 (1984)
Vlak et al., *J. Gen. Virol.*, 69:765 (1988)
Walker and Gaastra, eds., Techniques in Molecular Biology, MacMillan Publishing Company, New York (1983)
Wang et al., *J. Bacteriol.*, 172: 949 (1990)
Watson, Molecular Biology of the Gene, 4th edition, Benjamin/Cummings Publishing Company, Inc., Menlo Park, Calif. (1987)
Weissmann, "The cloning of interferon and other mistakes", in: Interferon 3 (ed. I. Gresser), 1981
Williams et al., *Control of Drosophila wing and haltere development by the nuclear vestigial gene product*, Genes Dev. Dec. 5, (12B):2481-95 (1991)
Wright, *Nature*, 321: 718 (1986)
Yelverton et al., *Nuc. Acids Res.*, 9:731 (1981)
Zimmerman, *Biochem. Biophys. Acta.*, 694:227 (1982)

All publications, patents and patent applications cited herein and priority U.S. patent application Nos. 60/383,359 and 60/383468 are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. An isolated nucleic acid encoding a polypeptide for production of a GLP-2 peptide, the encoded polypeptide comprising:
two or more copies of the GLP-2 peptide; and
a clostripain cleavage recognition sequence;
wherein the clostripain cleavage recognition sequence is comprised of amino acids at the N-terminus and/or the C-terminus of the GLP-2 peptide and/or of an optional linker, the clostripain cleavage recognition sequence positioned to allow cleavage by clostripain between the copies of the GLP-2 peptide;
wherein the clostripain cleavage recognition sequence comprises Formula I:

-$Xaa_1$-$Xaa_2$-$Xaa_3$-     (I);

wherein $Xaa_1$ is aspartic acid, glycine, proline or glutamic acid, $Xaa_2$ is arginine, and $Xaa_3$ is not an acidic amino acid.

2. The nucleic acid of claim 1, wherein the GLP-2 peptide is a native GLP-2 peptide.

3. The nucleic acid of claim 2, wherein the GLP-2 peptide is GLP-2(1-34) (SEQ ID NO:9).

4. The nucleic acid of claim 2, wherein the GLP-2 peptide is GLP-2(1-33) (SEQ ID NO:11).

5. The nucleic acid of claim 1, wherein the GLP-2 peptide is a variant of a native GLP-2 peptide.

6. The nucleic acid of claim 5, wherein the GLP-2 peptide is GLP-2(1-34,A2G) (SEQ ID NO:15).

7. The nucleic acid of claim 5, wherein the GLP-2 peptide is GLP-2(1-33,A2G) (SEQ ID NO:13).

8. The nucleic acid of claim 1, wherein the encoded polypeptide for production of the GLP-2 peptide comprises the following formula:

Tag-Linker-[Peptide]$_q$ wherein,
Tag comprises SEQ ID NO:17 or 18;
Linker comprises at least one of SEQ ID NO: 23, SEQ ID NO: 24, SEQ ID NO: 25, SEQ ID NO: 26, SEQ ID NO: 27, SEQ ID NO: 34, SEQ ID NO: 35 and SEQ ID NO: 36;
Peptide is GLP-2(1-34) (SEQ ID NO: 9) or GLP-2(1-34, A2G) (SEQ ID NO: 15); and
q is an integer of 2 to about 20.

9. The nucleic acid of claim 1, wherein the encoded polypeptide for production of the GLP-2 peptide comprises the following formula:

Tag-Linker-[Peptide-Linker$_2$]$_q$ wherein:
Tag comprises SEQ ID NO:17 or SEQ ID NO: 18;
Linker comprises at least one of SEQ ID NO: 23, SEQ ID NO: 24, SEQ ID NO: 25, SEQ ID NO: 26, SEQ ID NO: 27, SEQ ID NO: 34, SEQ ID NO: 35 and SEQ ID NO: 36;
Linker$_2$ is SEQ ID NO:23;
Peptide is GLP-2(1-34) (SEQ ID NO: 9) or GLP-2(1-34, A2G) (SEQ ID NO: 15); and
q is an integer of 2 to about 20.

10. An isolated nucleic acid encoding a polypeptide for production of a GLP-2 peptide, the encoded polypeptide comprising:
a GLP-2 peptide;
wherein the GLP-2 peptide is selected from GLP-2(1-34) (SEQ ID NO:9), GLP-2(1-33) (SEQ ID NO:11), GLP-2(1-34,A2G) (SEQ ID NO:15) and GLP-2(1-33,A2G) (SEQ ID NO:13); and
a clostripain cleavage recognition sequence;
wherein the clostripain cleavage recognition sequence is comprised of amino acids at the N-terminus of the GLP-2 peptide and/or of an optional linker, the clostripain cleavage recognition sequence positioned to allow cleavage by clostripain at the N-terminus of the GLP-2 peptide;
wherein the clostripain cleavage recognition sequence comprises Formula I:

-$Xaa_1$-$Xaa_2$-$Xaa_3$-     (I);

wherein $Xaa_1$ is aspartic acid, glycine, proline or glutamic acid, $Xaa_2$ is arginine, and $Xaa_3$ is not an acidic amino acid.

11. The nucleic acid of claim 10, wherein the GLP-2 peptide is a native GLP-2 peptide.

12. The nucleic acid of claim 11, wherein the GLP-2 peptide is GLP-2(1-34) (SEQ ID NO:9).

13. The nucleic acid of claim 11, wherein the GLP-2 peptide is GLP-2(1-33) (SEQ ID NO:11).

14. The nucleic acid of claim 10, wherein the GLP-2 peptide is a variant of a native GLP-2 peptide.

15. The nucleic acid of claim 14, wherein the GLP-2 peptide is GLP-2(1-34,A2G) (SEQ ID NO:15).

16. The nucleic acid of claim 14, wherein the GLP-2 peptide is GLP-2(1-33,A2G) (SEQ ID NO:13).

17. The nucleic acid of claim 10, wherein the encoded polypeptide for production of the GLP-2 peptide comprises the following formula:

Tag-Linker-Peptide wherein,
Tag comprises SEQ ID NO:17 or 18;
Linker comprises at least one of SEQ ID NO: 23, SEQ ID NO: 24, SEQ ID NO: 25, SEQ ID NO: 26, SEQ ID NO: 27, SEQ ID NO: 34, SEQ ID NO: 35 and SEQ ID NO: 36; and
Peptide is GLP-2(1-33) (SEQ ID NO:11) or GLP-2(1-33, A2G) (SEQ ID NO:13).

18. An isolated nucleic acid encoding a polypeptide for production of a GLP-2 peptide, the encoded polypeptide comprising the following formula:

$Xaa_1$-$Xaa_2$-Peptide wherein $Xaa_1$ is aspartic acid, glycine, proline or glutamic acid, $Xaa_2$ is arginine, and Peptide is a GLP-2 peptide; and wherein the GLP-2 peptide is selected from GLP-2(1-34) (SEQ ID NO:9, GLP-2(1-33) (SEQ ID NO:11), GLP-2(1-34,A2G) (SEQ ID NO:15) and GLP-2(1-33,A2G) (SEQ ID NO:13).

19. The nucleic acid of claim 18, wherein the GLP-2 peptide is GLP-2(1-33,A2G).

* * * * *